(12) United States Patent
Torres-Gonzalez et al.

(10) Patent No.: US 12,385,102 B2
(45) Date of Patent: Aug. 12, 2025

(54) ASSAYS AND METHODS FOR DETERMINING MICROBIAL RESISTANCE

(71) Applicants: STRECK LLC, La Vista, NE (US); CREIGHTON UNIVERSITY, Omaha, NE (US)

(72) Inventors: Maria Torres-Gonzalez, Omaha, NE (US); Nancy Hanson, Omaha, NE (US); Joel Lechner, Omaha, NE (US); Stephanie Cossette, Omaha, NE (US); Cathy Scheer, Omaha, NE (US); Matthew R. Kreifels, Elkhorn, NE (US); Stacey Morrow, Omaha, NE (US); Christopher Connelly, Gretna, NE (US); Laura R. Porter, Omaha, NE (US); Randy Fowler, Broomfield, CO (US)

(73) Assignees: STRECK, LLC, La Vista, NE (US); CREIGHTON UNIVERSITY, Omaha, NE (US)

( * ) Notice: Subject to any disclaimer, the term of this patent is extended or adjusted under 35 U.S.C. 154(b) by 0 days.

(21) Appl. No.: 18/332,590

(22) Filed: Jun. 9, 2023

(65) Prior Publication Data
US 2024/0150850 A1 May 9, 2024

Related U.S. Application Data

(62) Division of application No. 16/310,074, filed as application No. PCT/US2017/037700 on Jun. 15, 2017, now Pat. No. 11,708,614.

(60) Provisional application No. 62/350,457, filed on Jun. 15, 2016.

(51) Int. Cl.
| | |
|---|---|
| *C12Q 1/689* | (2018.01) |
| *C12Q 1/6809* | (2018.01) |
| *C12Q 1/6837* | (2018.01) |
| *C12Q 1/6851* | (2018.01) |
| *C12Q 1/686* | (2018.01) |

(52) U.S. Cl.
CPC ........... *C12Q 1/689* (2013.01); *C12Q 1/6809* (2013.01); *C12Q 1/6837* (2013.01); *C12Q 1/6851* (2013.01); *C12Q 1/686* (2013.01); *C12Q 2545/101* (2013.01); *C12Q 2600/106* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,539,082 A | 7/1996 | Nielsen et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,242,223 B1 | 6/2001 | Hanson et al. |

(Continued)

FOREIGN PATENT DOCUMENTS

| | | |
|---|---|---|
| CN | 104946764 A | 9/2015 |
| EP | 1072679 A2 | 1/2001 |

(Continued)

OTHER PUBLICATIONS

Streck, Philisa ampC ID Kit Ad—CLP, Identify the threat of antibiotic resistant bacteria faster, 1 page (Sep. 2014).

(Continued)

*Primary Examiner* — Samuel C Woolwine
*Assistant Examiner* — Carolyn L Greene
(74) *Attorney, Agent, or Firm* — MARSHALL, GERSTEIN & BORUN LLP

(57) ABSTRACT

Assays and methods for detecting resistance to beta-lactam antibiotics including detection of multiple β-lactamase family specific gene targets by polymerase chain reaction or microarray. One or more kits including primers and/or probes for identification of β-lactamase genes selected from the group consisting of one or more of the following: MOX-like, FOX-like, ACC-like, ACT/MIR-like, CMY-2-like, DHA-like, CTX-M-14-like, CTX-M-15-like, VIM-like, NDM-like, IMP-like, KPC-like, and OXA-48-like, OXA-51-like, OXA-143-like, OXA-58-like, OXA-23-like, OXA-24/40-like, TEM-like, and SHV-like. A kit may also include one or more primers and/or probes for the identification a non-beta lactamase gene family which confers antibiotic resistance, such as the MCR-1 gene.

10 Claims, 9 Drawing Sheets

Specification includes a Sequence Listing.

(56) References Cited

U.S. PATENT DOCUMENTS

| | | | |
|---|---|---|---|
| 6,893,846 | B2 | 5/2005 | Hanson et al. |
| 6,905,848 | B2 | 6/2005 | Hanson et al. |
| 7,045,291 | B2 | 5/2006 | Hanson et al. |
| 7,476,520 | B2 | 1/2009 | Hanson et al. |
| 7,521,547 | B2 | 4/2009 | Hanson et al. |
| 9,120,840 | B2 | 9/2015 | Janssen et al. |
| 11,708,614 | B2 | 7/2023 | Torres-Gonzalez et al. |
| 2003/0219749 | A1 | 11/2003 | Hanson et al. |
| 2007/0248954 | A1 | 10/2007 | Hanson |
| 2009/0197275 | A1 | 8/2009 | Boonyarantanakornkit et al. |
| 2016/0085912 | A1 | 3/2016 | Jones et al. |
| 2019/0017774 | A1 | 1/2019 | Vanek et al. |

FOREIGN PATENT DOCUMENTS

| | | |
|---|---|---|
| KR | 10-1908870 B1 | 10/2018 |
| WO | 97/12896 A1 | 4/1997 |
| WO | 98/39352 A1 | 9/1998 |
| WO | 99/06594 A1 | 2/1999 |
| WO | 99/14226 A2 | 3/1999 |
| WO | 2010/130882 A1 | 11/2010 |
| WO | 2012/027302 A2 | 3/2012 |
| WO | 2012/027302 A3 | 6/2012 |
| WO | 2015/138991 A2 | 9/2015 |
| WO | 2015/138991 A3 | 11/2015 |
| WO | 2016/067047 A1 | 5/2016 |
| WO | 2017/218789 A1 | 12/2017 |

OTHER PUBLICATIONS

Streck, Philisa ampC ID Kit JMD, Identify the threat of antibiotic resistant bacteria faster with the philisa (Registered) ampC ID kit, 1 page (Nov. 2014).
Streck, Philisa ampC ID Kit Poster Ad—CAP Today, Identify the threat of antibiotic resistant bacteria faster with the philisa (Registered) ampC ID kit, 1 page (Oct. 2014).
Streck, Streck ARM-D Kit, BETA-Lactamase (RUO), Ref. 350670-1 (Nov. 2017).
Streck, Streck ARM-D Kits (RUO) Data Acquisition & Analysis Guide—Bio-Rad CFX96 Touch (Trademark) Real-Time PCR Detection System. Ref. 880107-1 (Dec. 2017).
Torres et al., Detection of ESBLs, MBLs, KPCs, and plasmid-mediated ampC (Beta)-lactamase genes by multiplex real-time PCR, American Society for Microbiology (ASM) Microbe 2016 Conference, 12 pages. (Jun. 18, 2016). Poster presentation.
Torres et al., Rapid detection of OXA (Beta)-lactamases by multiplex real-time PCR, Streck research and development-molecular technology division, La Vista, NE, 1 (2011).
Torres et al., Rapid detection of plasmid-mediated ampC (Beta)-lactamase genes by multiplex real-time PCR, American Society for Microbiology (ASM) Microbe 2015 Conference, 1O pages (May 31, 2015). Poster presentation.
Torres et al., Rapid detection of plasmid-mediated ampC (Beta)-lactamase genes by multiplex real-time PCR, Streck, Research and development, Molecular technology division, 1 (2015).
Vandenbussche et al., A Tale of Tails: Dissecting the Enhancing Effect of Tailed Primers in Real-Time PCR, PLoS One, 11(10):e0164463 (2016).
Vazquez-Ucha et al., Activity of the (Beta)-Lactamase Inhibitor LN-1-255 against Carbapenem-Hydrolyzing Class D (Beta)-Lactamases from Acinetobacter baumannii, Antimicrobial Agents and Chemotherapy, 61(11):e01172-17 (2017).
Vázquez-Ucha et al et al., Activity of the B-Lactamase Inhibitor LN-1-255 against Carbapenem-Hydrolyzing Class D ß-Lactamases from Acinetobacter baumannii, Antimicrobial Agents and Chemotherapy, 61(11):e01172-17 (2017).
Yin et al., Novel Plasmid-Mediated Colistin Resistance Gene mcr-3 in *Escherichia coli*, mBIO, 8(3):e00543-17 (2017).
"Streck Arm-D Kits," Jun. 22, 2017.

Alao et al., Detection of mobilized colistin resistance (mcr) genes by multiplex real-time PCR: improving surveillance of an emerging threat, APHL, 1 (2019).
Alao et al., Improved methodology for detection of antibiotic resistance in gram-negative bacteria, European Congress of Clinical Microbiology and Infectious Diseases (ECCMID) Conference, 14 pages. (Apr. 24, 2018). Poster presentation.
Anandan et al., Structure of a lipid A phosphoethanolamine transferase suggests how conformational changes govern substrate binding, Proc. Nat. Acad. Sci. USA, 114(9):2218-2223 (2017).
Antunes et al., Acquired Class D ß-Lactamases, Antibiotics, 3(3):398-434 (2014).
Beck et al., Digital Droplet PCR for Rapid Quantification of Donor DNA in the Circulation of Transplant Recipients as a Potential Universal Biomarker of Graft Injury, Clinical chemistry, 59(12):1732-41 (2013).
Borowiak et al., Identification of a novel transposon-associated phosphoethanolamine transferase gene, mcr-5, conferring colistin resistance in d-tartrate fermenting *Salmonella enterica* subsp. enterica serovar Paratyphi B, J. Antimicrob Chemother, 72:3317-3324 (2017).
Carattoli et al., Novel plasmid-mediated colistin resistance mcr-4 gene in Salmonella and *Escherichia coli*, Italy 2013, Spain and Belgium 2015 to 2016, Euro Surveill, 22(31):30589 (2017).
Concise encyclopedia of polymer science and engineering, J. I. Kroschwitz Ed., John Wiley & Sons, 858-859 (1990).
Connelly et al., Antiobiotic Resistance Monitoring and Detection (ARM-D™) PCR Kits: ARM-D™ for b-Lactamase ID—Technical Note—Detection of ESBLs, MBLs, KPCs, and plasmid-mediated AmpCs, using the b-Lactamase ID kit to identify antiuobiotic resistance in Gram-negative pathogens, Biotechniques Rapid Dispatches, 57(6):317-318 (2014).
Cook, Medicinal chemistry of antisense oligonucleotides-future opportunities, Anti-Cancer Drug Design, 6(6):585-607 (1991).
Cossette et al., Rapid detection of OXA (Beta)-lactamases by multiplex real-time PCR, American Society for Microbiology (ASM) Microbe 2018 Conference, 8 pages (Jun. 8, 2018). Poster presentation.
Cussac et al., Reduction of the toxicity and mutagenicity of aziridine in mammalian cells harboring the *Escherichia coli* fpg gene, Nucleic Acids Research, 24(9):1742-1746 (1996).
Declaration of Nicole Quackenbush, dated Mar. 8, 2022, filed during the prosecution of U.S. Appl. No. 16/310,074.
Ebili et al., "Squirrel" Primer-Based PCR Assay for Direct and Targeted Sanger Sequencing of Short Genomic Segments, J. Biomol. Tech., 28(3):97-110 (2017).
Englisch et al., Chemically Modified Oligonucleotides as Probes and Inhibitors, Angew. Chem. Int. Ed., 30(6):613-629 (1991).
Evans et al., OXA ß-Lactamases, Clinical Microbiology Reviews, 27(2):241-263 (2014).
Extended European Search Report dated Oct. 21, 2016; Application No. 15196213.1.
Freier et al., The ups and downs of nucleic acid duplex stability: structure-stability studies on chemically-modified DNA:RNA duplexes, Nucl. Acid. Res., 25:4429-4443 (1997).
Geyer et al., Development of a TaqMan multiplex PCR assay for detection of plasmid-mediated ampC ß-lactamase genes, J. Clin. Microbiol., 50(11):3722-5 (2012).
Hanson, One 20-minute multiplex assay for the detection of 10 targets including ampCs, ESBLs, MBLs, and KPCs using rapid PCR amplification, Center for research in anti-infectives and biotechnology creighton university omaha, NE, 19 (2014).
International Application No. PCT/US20/35422, International Preliminary Report on Patentability, mailed Dec. 9, 2021.
International Preliminary Report on Patentability for International Application No. PCT/US2014/047551 dated Dec. 10, 2015.
International Preliminary Report on Patentability from International Application No. PCT/US2012/036304 dated Aug. 16, 2013.
International Preliminary Report on Patentability from International Application No. PCT/US2017/37700, dated Dec. 27, 2018.
International Search Report and Written Opinion from International Application No. PCT/US20/35422 dated Nov. 13, 2020.
International Search Report and Written Opinion from International Application No. PCT/US2012/036304 dated Nov. 21, 2012.

(56) References Cited

OTHER PUBLICATIONS

International Search Report and Written Opinion from International Application No. PCT/US2017/037700 dated Dec. 21, 2017.
International Search Report and Written Opinion from International Application No. PCT/US2017/046537 dated Oct. 23, 2017.
Moland et al., Occurrence of Newer-Lactamases in Klebsiella pneumoniae Isolates from 24 U.S. Hospitals, Ant. Agen. Chem., 46(12):3837-3842 (2002).
Nielsen et al., Sequence-selective recognition of DNA by strand displacement with a thymine-substituted polyamide, Science, 254(5037):1497-1500 (1991).
Perez-Perez et al., Detection of plasmid-mediated AmpC beta-lactamase genes in clinical isolates by using multiplex PCR, J. Clin. Micro., 40(6):2153-2162 (2002).
Pitout et al., Phenotypic and Molecular Detection of CTX-M—Lactamases Produced by *Escherichia coli* and Klebsiella spp, J. Clin. Micro., 42(12):5715-5721 (2004).
Poirel et al., Diversity, epidemiology, and genetics of class D beta-lactamases, Antimicrobial Agents and Chemotherapy, 54(1):24-38 (2010).
Sanghvi, Chapter 15, Antisense research and applications, Ed. S. T. Crooke and B. Lebleu, CRC Press, 289-302 (1993).
Silbert, Evaluation of different tests to screen and identify carbapenemase-production bacteria strains, Microbiology, 43 (2019).
Sobansky et al., Development of Accurate and Reliable Full-Process Controls that Mimic Patient Samples for Molecular Diagnostic Testing, Poster Presentation ASM Microbe (2017).
Streck, Philisa ampC ID Kit Ad—CAP Today, Identify the threat of antibiotic resistant bacteria faster, 1 page (May 2014).
Favaro et al., Multiplex real-time PCR probe-based for identification of strains producing: OXA48, VIM, KPC and NDM, World Journal of Microbiology and Biotechnology, 30(1): 2995-3001(2014).
Kaase et al., Detection of Carbapenemases in Enterobacteriaceae by a Commercial Multiplex PCR, Journal of Clinical Microbiology, 50(9): 3115-3118(2012).
Hernandez et al., Stability study of (Beta)-lactamase detection from gram-negative bacilli directly from positive blood cultures using two commercially available PCR kits, American Society for Microbiology (ASM) Microbe 2018 Conference, 8 pages. (Jun. 8, 2018). Poster presentation.
Quickgene, Series Application Guide, Genomic DNA extraction from Pseudomonas aeruginosa. 37 (Jun. 2023).

The Streck ARM-D (Registered) kits are multiplex real-time PCR kits for the detection of clinically-relevant(Beta)-lactamase genes, Product overview, 27 pages (Jan. 2021).
Database EMBL [Online], Citrobacter freundii strain 90757 class C beta-lactamase CMY-39 gene, complete cds, XP002772843, retrieved from EBI accession No. EM STD:HM565135 Database accession No. HM565135 (2010).
Database EMBL [Online], Citrobacter freundii strain W704 AmpR transcriptional regulator (ampR) and AmpC beta-lactamase CMY-80 (blaCMY-80) genes, complete cds; and outer membrane lipoprotein Blc (blc) gene, partial cds, XP002772846, retrieved from EBI accession No. EM STD:JQ733577 Database accession No. JQ733577 (2012).
Database EMBL [Online], Citrobacter freundii strain W811 transcriptional regulator AmpR (ampR) gene, partial cds; beta-lactamase AmpC (blaCMY-86) gene, complete cds; and outer membrane lipoprotein Blc (blc) gene, partial cds, XP002772845, retrieved from EBI accession No. EM STD: KJ207204 Database accession No. KJ207204 (2014).
Database EMBL [Online], *Escherichia coli* strain 2011/34/01 AmpC beta-lactamase (blaCMY-108) gene, complete cds, XP002772844, retrieved from EBI accession No. EM STD: KF564648 Database accession No. KF564648 (2014).
Database Geneseq [online] Apr. 12, 2012 (Apr. 12, 2012) "Antibiotic resistance gene sequence, Seq ID 227", Apr. 12, 2012, Accessin No. AZT75073.
Database Geneseq [Online], Antibiotic resistance gene CFE-1 forward PCR primer Seq ID 120, XP002772841 retrieved from EBI accession No. GSN:BCE41068 Database accession No. BCE41068 (2015).
Database Geneseq [Online], *Escherichia coli* beta-lactamase gene fragment, Seq ID 7, XP002772847, retrieved from EBI accession No. GSN:BCM28931 Database accession No. BCM28931 (2016).
Integrated DNA Technologies, Better PCR probes: A second quencher lowers backrgound, increasing signal detection, 2021. (Year: 2021).
Alao et al., Detection of mobilized colistin resistance (mer) genes by multiplex real-time PCR: improving surveillance of an emerging threat, Association of Public Health Laboratories (APHL) Conference, 6 pages (Jun. 4, 2019). Poster presentation.
Alao et al., Improved methodology for detection of antibiotic resistance in gram-negative bacteria, Streck research and development-molecular technology division, La Vista, NE, 1 page (2018).
Torres et al., Detection of ESBLs, MBLs, KPCs, and plasmid-mediated ampC (Beta)-lactamase genes by multiplex real-time PCR, Streck research and development, molecular technology division, Omaha, NE, 1 page (2016).

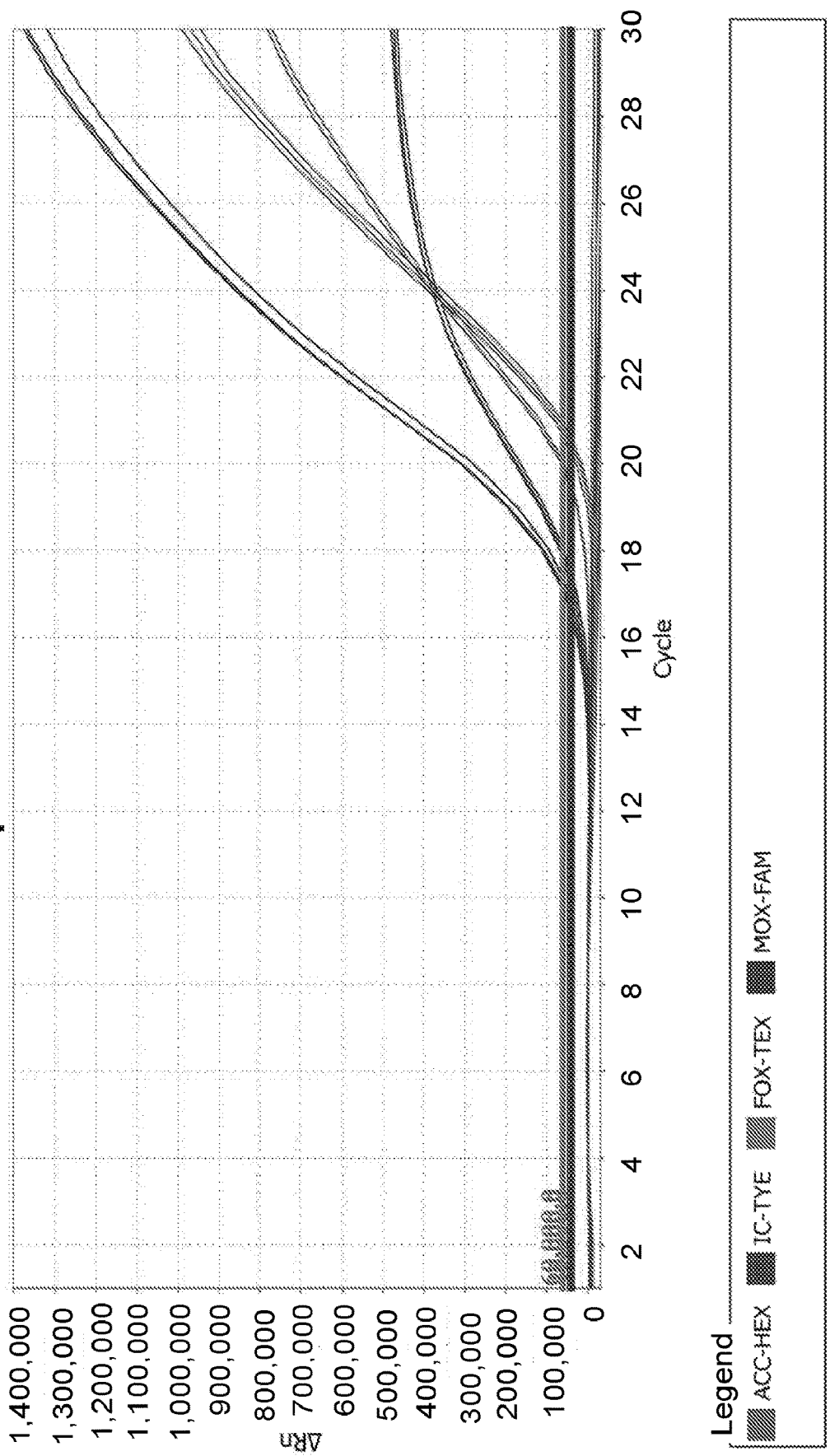

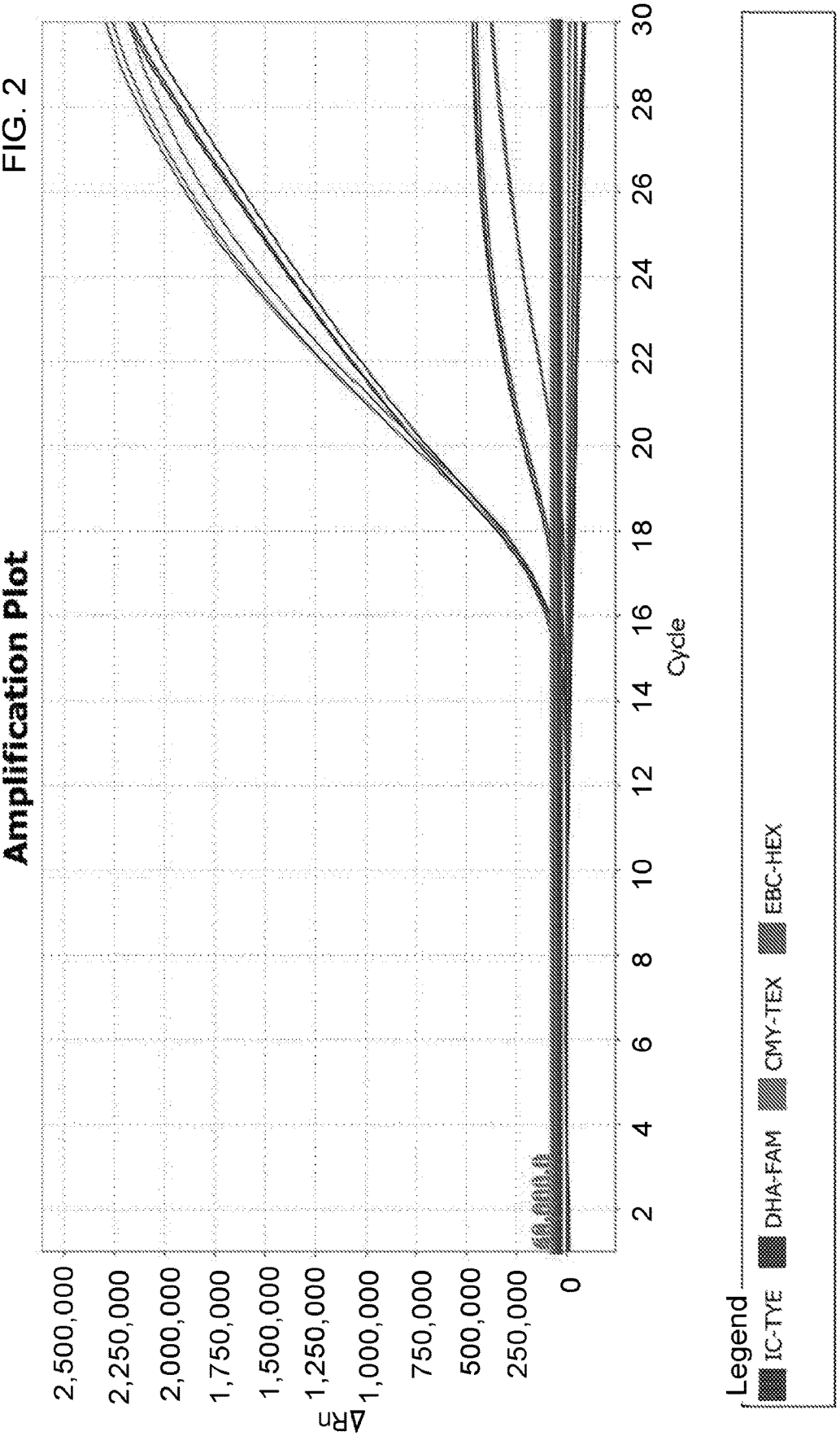

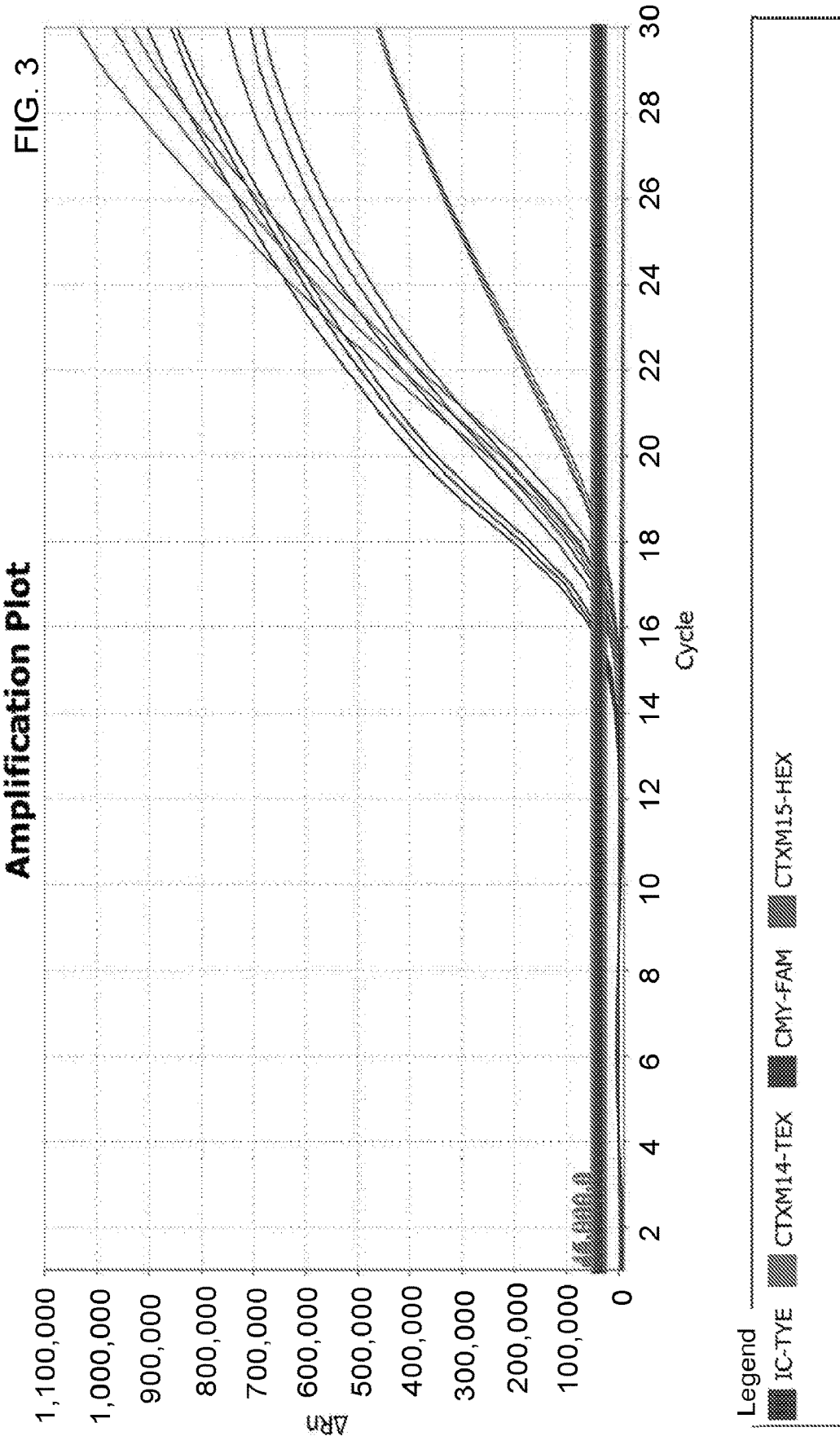

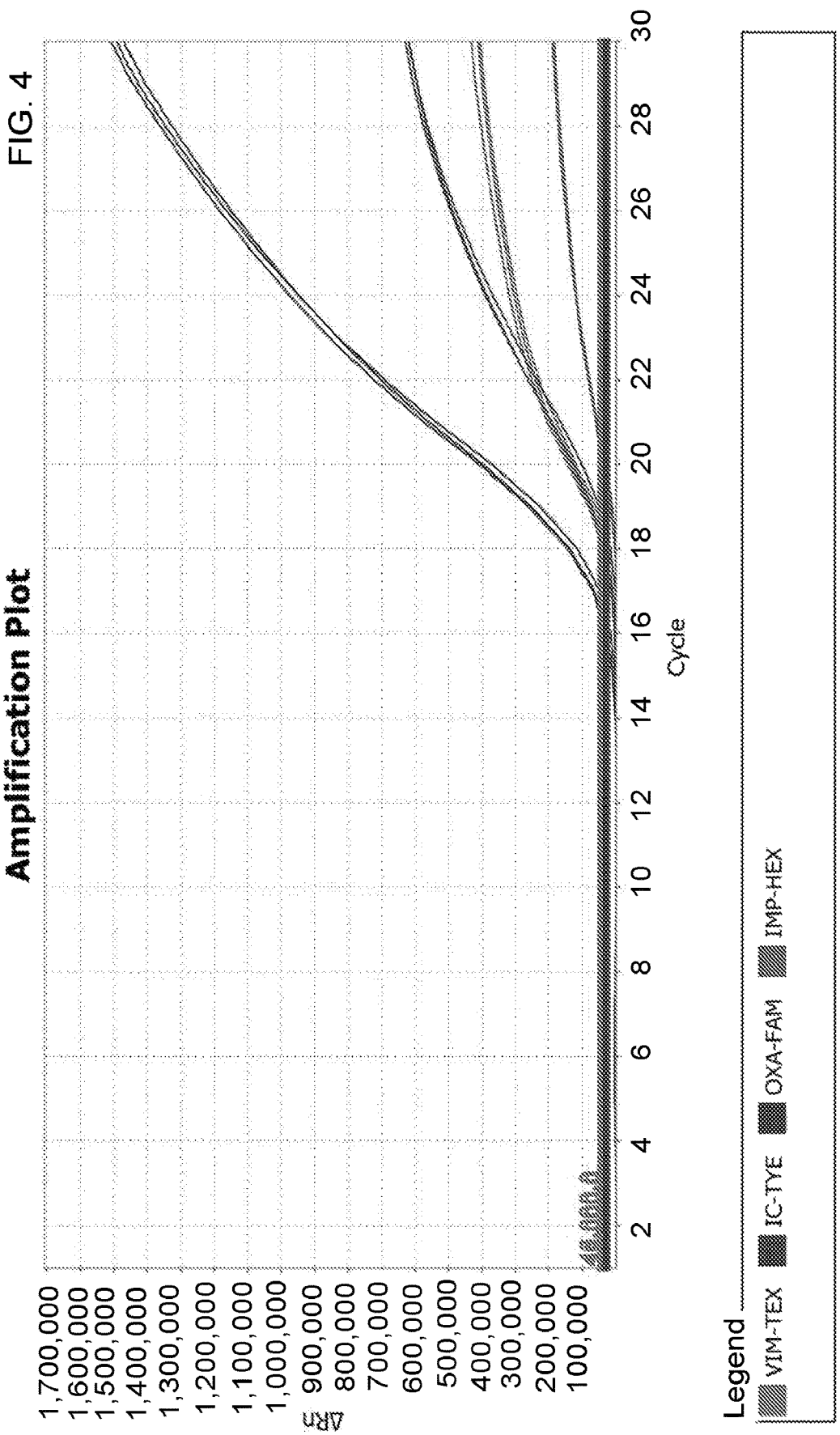

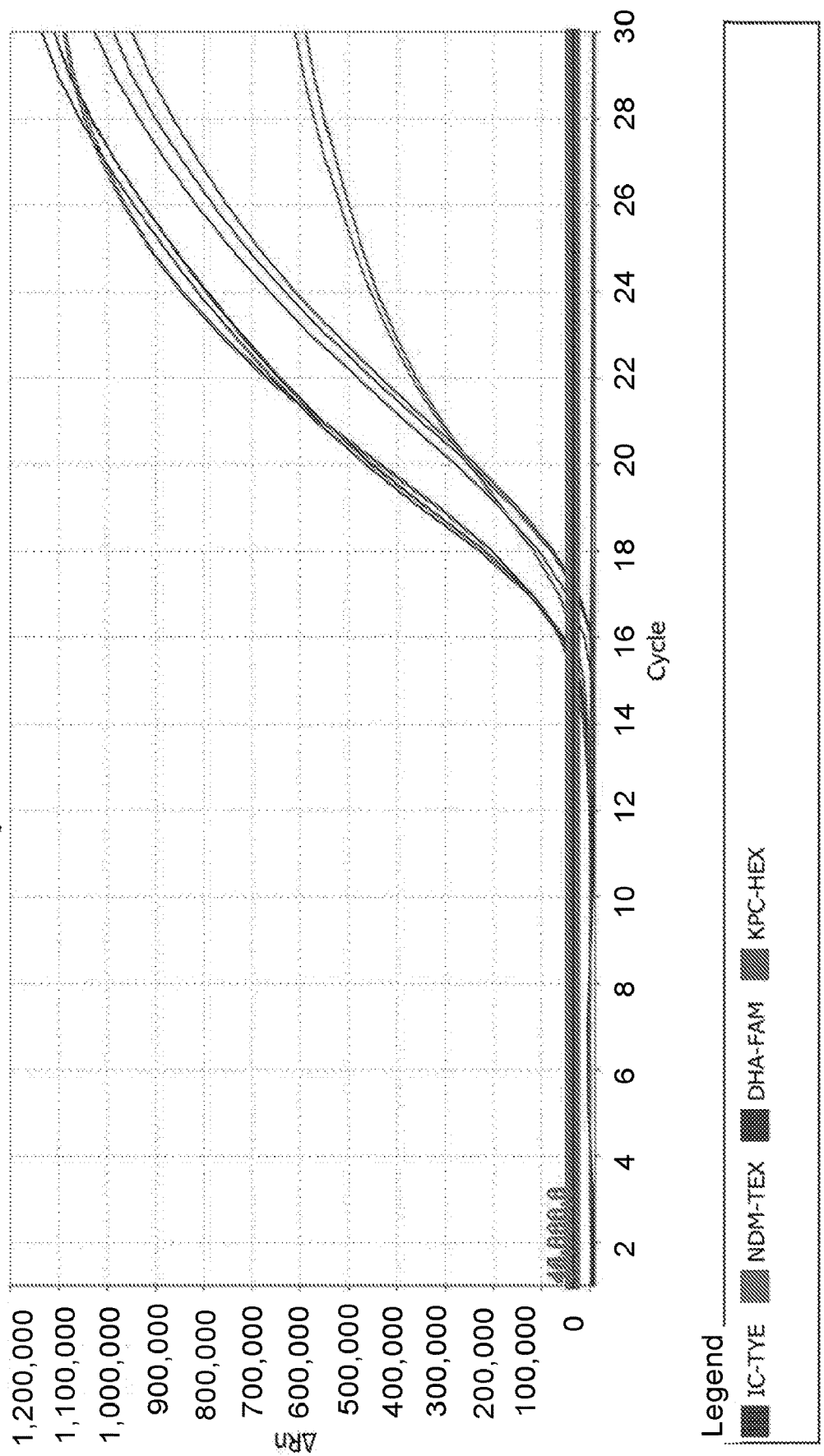

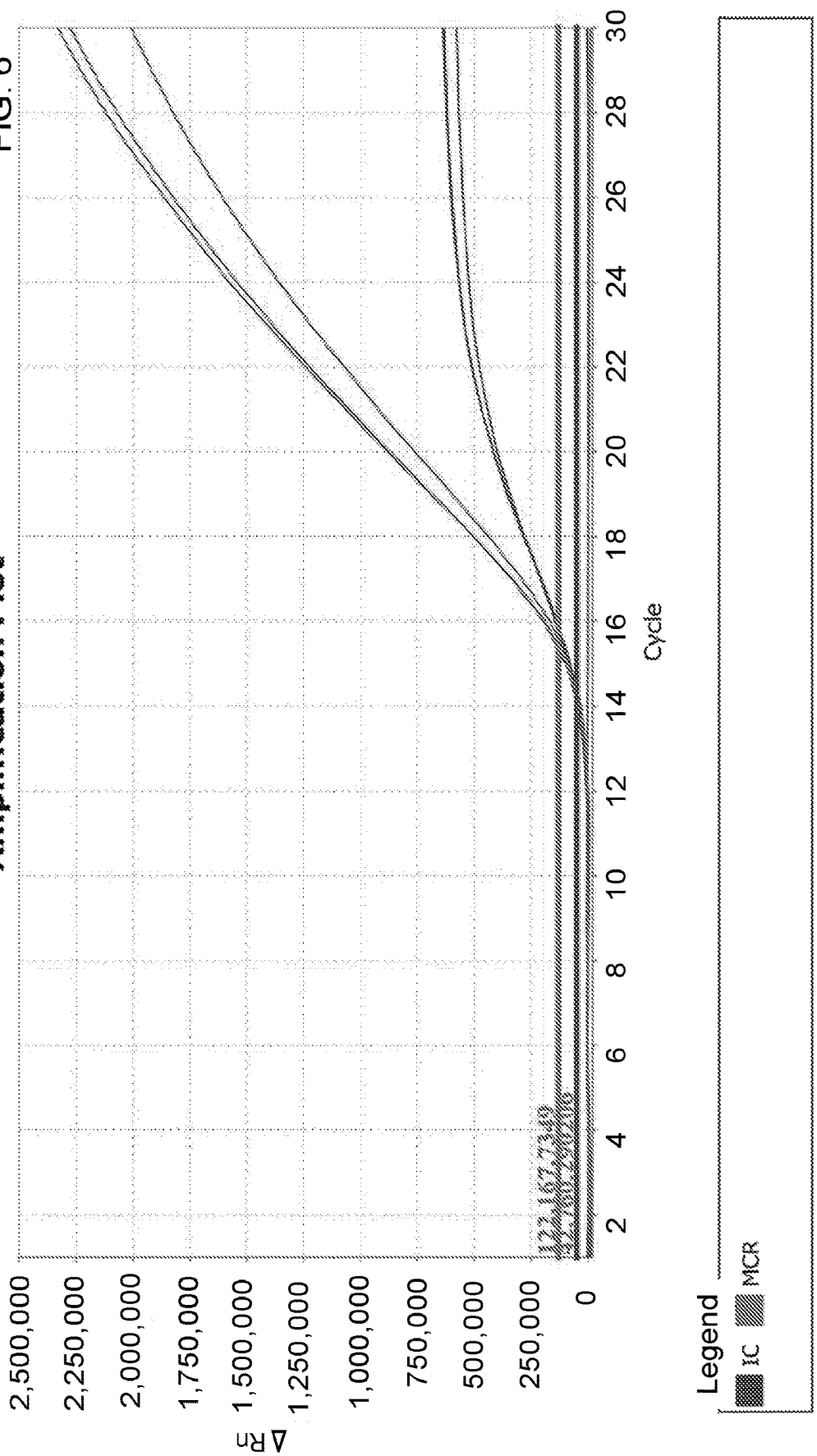

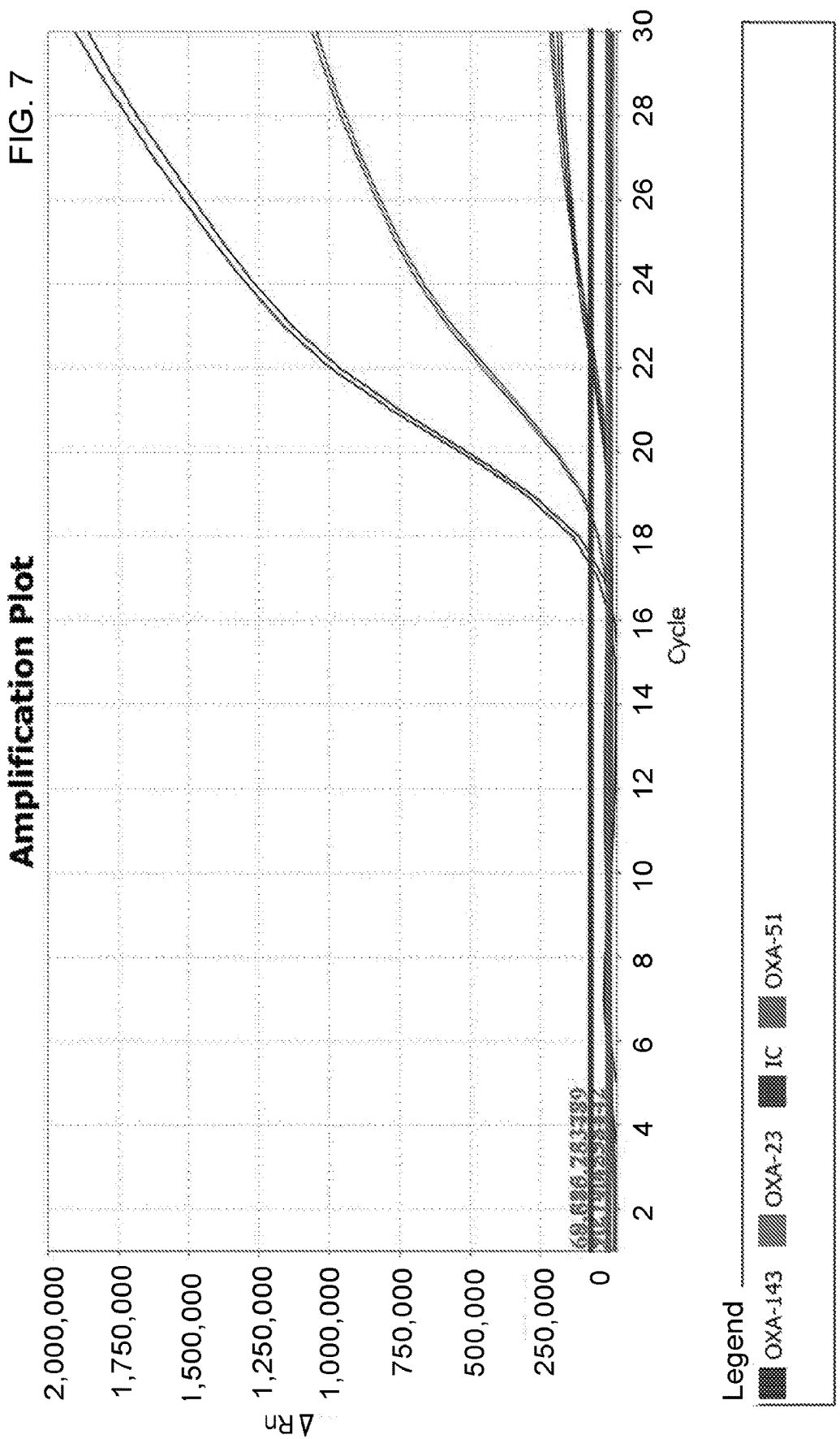

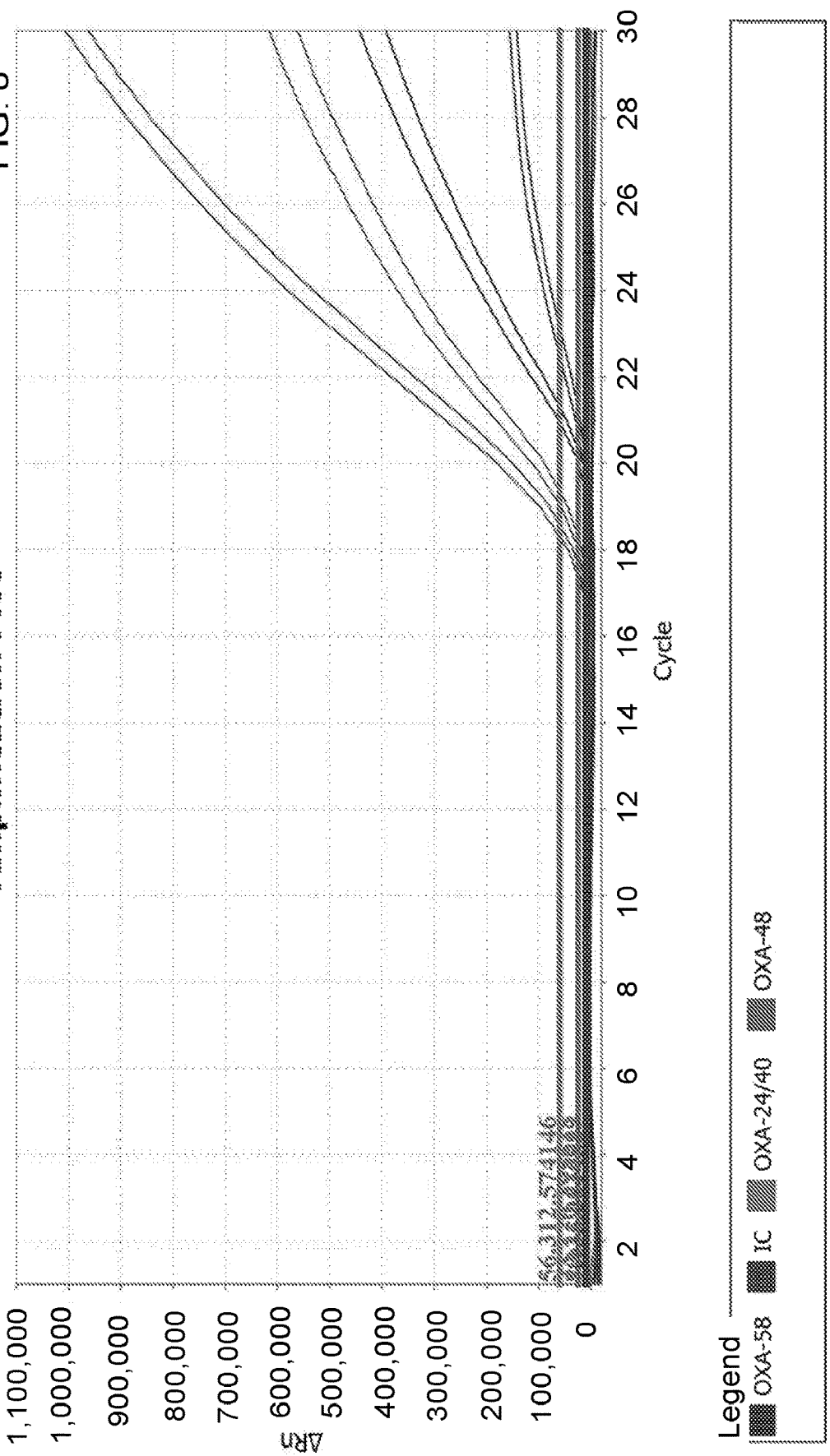

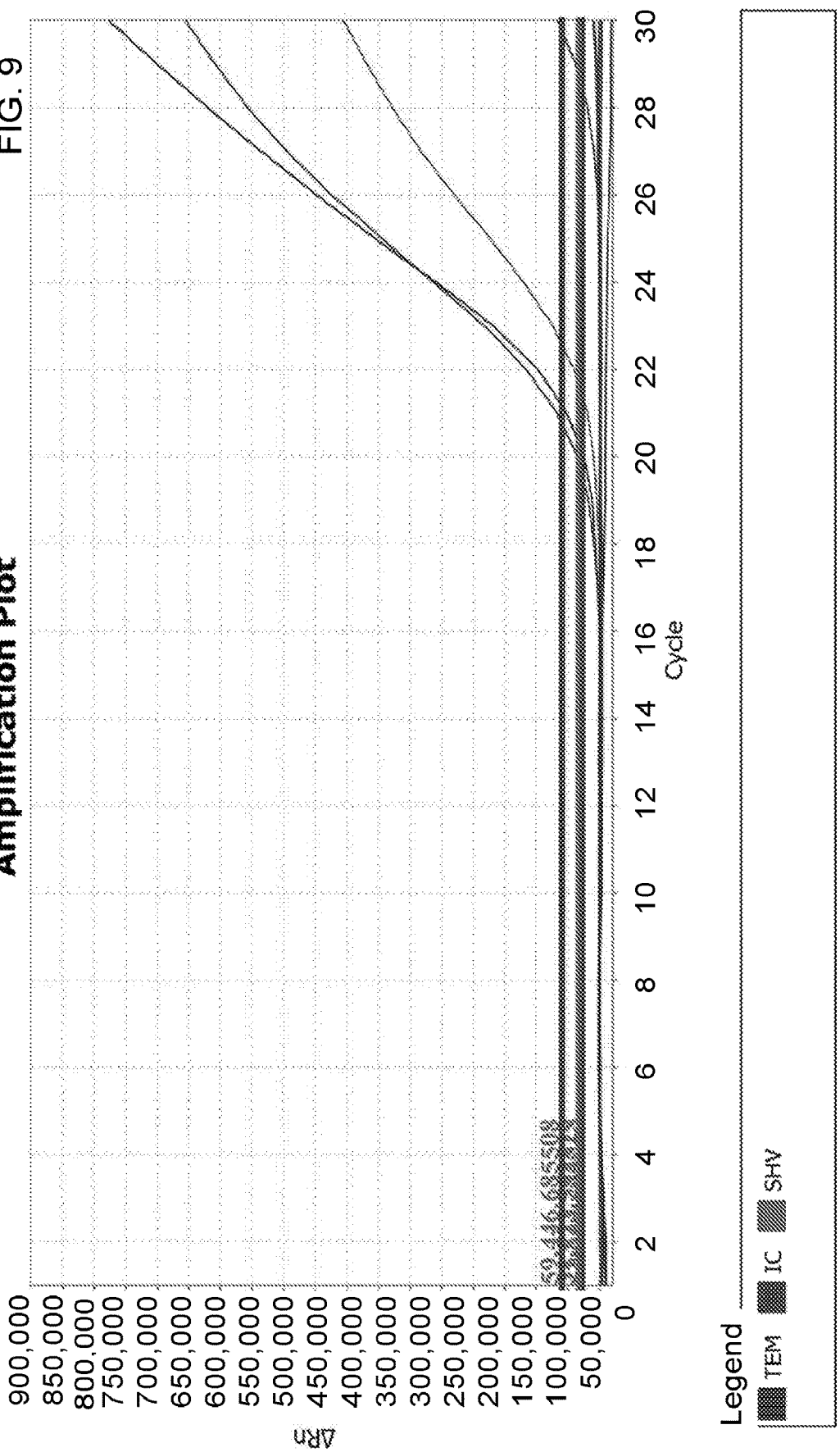

ASSAYS AND METHODS FOR DETERMINING MICROBIAL RESISTANCE

CROSS-REFERENCE TO RELATED APPLICATIONS

This application is a Divisional of U.S. application Ser. No. 16/310,074, filed Dec. 14, 2018, now U.S. Pat. No. 11,708,614, issued Jul. 25, 2023, which is a U.S. National Phase of PCT/US17/37700, filed Jun. 15, 2017, which claims the priority benefit under 35 U.S.C. § 119(e) of U.S. Provisional Patent Application No. 62/350,457, filed Jun. 15, 2016, which are incorporated herein by reference in their entirety.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "50035A_SubSeqListing.xml", which was created on Jun. 8, 2023 and is 403,656 bytes in size. The subject matter of the Sequence Listing is incorporated herein in its entirety by reference.

FIELD

The present teachings relate to assays and methods for detecting resistance to antibiotics. The present teachings provide for the detection of family specific gene targets including AmpC β-lactamases, metallo-β-lactamases, carbapenemases, and extended-spectrum β-Lactamases by multiplex real-time polymerase chain reaction.

BACKGROUND

Bacterial resistance to antibiotics is a major public health issue. This resistance not only presents severe limitations to the ability to control and treat infection, but it also is difficult to identify and characterize in the laboratory. The significant increase in the resistance of pathogenic bacteria over the last 20 years, leads to extended periods of hospitalization, high morbidity and high mortality rates.

Enzymatic inactivation is the most common cause of resistance in terms of number of species and of antibiotics involved. As an example, β-lactamases are enzymes expressed by some bacteria. Such enzymes are capable of hydrolyzing the C—N bond of the β-lactam ring structure of a β-lactam antibiotic, effectively inactivating the antibiotic. Despite the existence of several β-lactamase inhibitors, the constant exposure of strains to antibiotics results in constant evolution of β-lactamases.

As a result, it becomes essential to be able to identify such resistant microorganisms and their resistance mechanisms as quickly as possible. Typically, biological samples can be tested for antibiotic resistance, but many test protocols are time consuming and/or limited in the types of resistance they are able to identify. It would therefore be beneficial to provide a test protocol for the simplified identification of resistance for all major β-lactamases.

One approach to the identification of β-lactamases has been to employ oligonucleotide primers specific for nucleic acid characteristic of certain β-lactamases with polymerase chain reaction to identify nucleic acid characteristics of family specific β-lactamase enzymes in samples. See for example, U.S. Pat. Nos. 6,893,846 and 7,476,520, incorporated by reference herein. Another approach has been to employ oligonucleotide primers specific for nucleic acid characteristic of certain AmpC β-lactamases with multiplex polymerase chain reaction to detect the presence or absence of an AmpC β-lactamase gene and to identify nucleic acid characteristic of AmpC β-lactamase genes in samples. Multiplex polymerase chain reaction refers to the use of polymerase chain reaction to amplify several different DNA sequences simultaneously in single or multiple reactions. See for example, U.S. Pat. Nos. 7,045,291 and 7,521,547 incorporated by reference herein.

However, such primers have been limited with regards to the number of β-lactamase gene families or the number of gene targets that may be identified. Furthermore, such primers have been employed mainly with conventional polymerase chain reaction, which typically requires agarose gels to detect and analyze the PCR product(s). The use of agarose gel detection methods based on size discrimination may lead to poor resolution and difficulty in interpreting the data. Conventional polymerase chain reaction also lacks the sensitivity to detect endpoint variability from sample to sample and may not be automated. Real-time polymerase chain reaction allows for monitoring of reaction products as they are formed.

Detection of β-lactamases using real-time polymerase chain reaction and a single primer set may be limited to detection of a single β-lactamase gene family. See for example, United States Patent Application 2007/0248954 incorporated by reference herein. Multiplex real-time polymerase chain reaction has been designed for the identification of many AmpC β-lactamases simultaneously. See Geyer C N, Reisbig M D, Hanson N D. Development of a TaqMan® Multiplex PCR Assay for Detection of Plasmid-Mediated AmpC β-lactamase Genes. *Journal of clinical microbiology*. 2012 Aug. 15:JCM-02038. The primer/probe combinations in this study, however, have been directed only to AmpC β-lactamases and are limited in the number of gene targets that may be identified.

Multiple factors such as primer and probe design, reaction conditions, and enzyme selection must all be considered when designing a working polymerase chain reaction. This complexity is compounded in multiplex PCR, in which multiple targets are detected simultaneously in the same tube. Balancing the concentrations of primers, probes, and control vectors provided as composite "multiplex PCR" mixes for an assay is a challenging aspect. It is extremely difficult to balance these ratios, as a change of concentration for any of these reagents, corresponding to just one of the genetic targets, may adversely affect detection of any other multiplex target in the reaction mix. If these concentrations are not balanced, one could expect a reduction in efficiency, sensitivity, and specificity. This would reduce confidence in the effectiveness of the assay to correctly identify the gene families identified with the described kits.

Therefore, there is a significant amount of time and technical know-how required to develop these assays into a reliable method. For example, the PCR master mixture, with DNA polymerase, is a customized formulation that permits the final assay to work. Concentrations of DNA polymerase and magnesium may have to be adjusted. The specific concentrations and ranges surrounding DNA polymerase and magnesium are required for the assay to work successfully. In addition to determining concentrations for all reagents, a PCR cycling protocol must be identified that is compatible with all reaction conditions and facilitates real-time multiplex polymerase chain reaction.

Accurate and rapid detection of antibiotic resistance is essential for surveillance, epidemiologic tracking, patient therapy, and infection control. Thus, a multiplex PCR based diagnostic assay should provide comprehensive genotypic characterization of β-lactamases and be versatile as well as providing rapid results. The present teachings make it possible to test a sample for the presence of antibiotic resistant microorganisms by identifying any of the major β-lactamases in one test. The present teachings provide for the detection of multiple family-specific β-lactamase gene targets, including but not limited to metallo-β-lactamases, carbapenemases, extended-spectrum β-Lactamases, ampC chromosomal and/or plasmid-mediated AmpC β-lactamases, by multiplex real-time polymerase chain reaction.

The present teachings provide for a kit or kits including one or more primers and/or probes for identification of β-lactamase genes selected from the group consisting of one or more of the following: MOX-like, FOX-like, ACC-like, ACT/MIR-like, CMY-2-like, DHA-like, CTX-M-14-like, CTX-M-15-like, VIM-like, NDM-like, IMP-like, KPC-like, and OXA-48-like, OXA-51-like, OXA-143-like, OXA-58-like, OXA-23-like, OXA-24/40-like, TEM-like, and SHV-like. The kits or kits of the present teachings may provide control material for the aforementioned β-lactamase genes. The present teachings provide one or more of the following: primers, probes, controls, assay process and detection strategy for one or more of the following β-lactamases: extended-spectrum β-lactamases (ESBLs), metallo-β-lactamases (MBLs), carbapenem-resistant enterobacteriaceaes (CREs), and serine-dependent carbapenemases and plasmid-mediated ampC β-lactamases. A kit may also include one or more primers and/or probes for the identification of mobilized colistin-resistant (MCR) genes, a non-beta lactamase gene family that confers antibiotic resistance. The present teachings provide multiplex PCR assays which may test for any combination of these or are directed towards identification of a specific group. The present teachings provide assays with improved clinical sensitivity and analytical specificity of detection. The primer, probes, and control DNA sequences of the present teachings provide both an analytical and commercial advantage as they permit enhanced screening capabilities for detection of a larger number of genetic variants associated with genes conferring resistance to antibiotics in Gram-negative bacteria.

SUMMARY

The present teachings provide a kit including one or more primers and/or probes for the identification by polymerase chain reaction, microarray, NGS-based target enrichment, and/or mass spectrometric characterization of one or more β-lactamase genes selected from the group consisting of: CMY, CTX-M, OXA, IMP, VIM, DHA, KPC, MOX, ACC, FOX, EBC, NDM, TEM, and SHV. The present teachings provide for one or more kits including primers and/or probes for identification of β-lactamase genes selected from the group consisting of one or more of the following: MOX-like, FOX-like, ACC-like, EBC-like, CMY-2-like, DHA-like, CTX-M-14-like, CTX-M-15-like, VIM-like, NDM-like, IMP-like, KPC-like, and OXA-48-like, OXA-51-like, OXA-143-like, OXA-58-like, OXA-23-like, OXA-24/40-like, TEM-like, and SHV-like. A kit may also include one or more primers and/or probes for the identification of a non-beta lactamase gene family which confers antibiotic resistance. A kit may include one or more primers and/or probes for the identification by polymerase chain reaction or microarray of MCR gene variants. Primers and probes may also be made compatible with next-generation sequencing and mass spectrometry.

BRIEF DESCRIPTION OF DRAWINGS

FIG. 1 depicts an amplification plot of an exemplary mix 1 of a kit including ampC gene targets.

FIG. 2 depicts an amplification plot of an exemplary mix 2 of a kit including ampC gene targets.

FIG. 3 depicts an amplification plot of an exemplary mix 1 of a kit including β-lactamase gene targets.

FIG. 4 depicts an amplification plot of an exemplary mix 2 of a kit including β-lactamase gene targets.

FIG. 5 depicts an amplification plot of an exemplary mix 3 of a kit including β-lactamase gene targets.

FIG. 6 depicts an amplification plot of an exemplary internal control mix of a kit including MCR gene targets.

FIG. 7 depicts an amplification plot of an exemplary mix 1 of a kit including OXA gene targets.

FIG. 8 depicts an amplification plot of an exemplary mix 2 of a kit including OXA gene targets.

FIG. 9 depicts an amplification plot of an exemplary internal control mix of a kit including SHV-TEM gene targets.

DETAILED DESCRIPTION

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Bacterial resistance to antibiotics poses a global threat to public health and in recent years has shown an increase in mortality rates and the potential to spread through the population. Of these resistance mechanisms, β-Lactamases are enzymes that cleave β-Lactam rings rendering the β-Lactam family of antibiotics ineffective for treatment of clinically-important Gram-negative bacterial infections. Specifically, β-Lactamases confer resistance to penicillins, cephamycins, and, in some cases, carbapenems. β-Lactam-resistant Gram-negative organisms, producing multiple or plasmid-mediated β-lactamases, are difficult to identify phenotypically and necessitate more specific detection methods to identify clinically important β-lactamases. Genetic identification of these resistance mechanisms is critical for active surveillance and infection control. Because these antibiotics are often selected for the management and prevention of infectious disease, the presence and characteristics of specific β-Lactamases play a critical role in selecting the appropriate antibiotic therapy.

AmpC β-lactamases are clinically important cephalosporinases that are resistant to most β-lactam antibiotics. AmpC enzymes are chromosomally encoded in many bacterial species and can be inducible and overexpressed as a consequence of mutation. Overexpression can lead to resistance to most β-lactam antibiotics. The occurrence of transmissible plasmids with acquired genes for AmpC β-lactamases often result in increased β-lactamase production, compared to chromosomally-expressed ampC genes. Additionally, plasmid-mediated AmpC β-lactamases can appear in organisms lacking or having low-level expression of a chromosomal ampC gene. Resistance due to plasmid-mediated AmpC enzymes can be broad in spectrum and often hard to detect. As such, it is clinically useful to detect and discriminate between plasmid-mediated and chromosomally expressed AmpC β-lactamases.

The present teachings relate to assays and methods for detecting Gram-negative bacteria resistant to beta-lactam antibiotics from a biological sample. β-lactam antibiotics are all antibiotic agents that contain a β-lactam ring in their molecular structures. β-lactam antibiotics include penicillins, cephalosporins, carbapenems and monobactams. Antibiotic resistant organisms may produce one or more enzymes known as β-lactamases that provide resistance to β-lactam antibiotics. β-lactamases may confer resistance by the bacteria to antibiotics, which is plasmid-mediated and/or chromosomally expressed making detection difficult.

β-lactamases may be classified based on molecular structure. The four major classes include A to D. Class A, C and D β-lactamases are serine based. Class B β-lactamases, also known as metallo-beta-lactamases, are zinc based.

Extended spectrum β-lactamases (ESBLs) are enzymes that confer bacterial resistance to certain categories of antibiotics, such as third-generation cephalosporins and monobactams. The presence of an ESBL-producing organism in a clinical infection can cause treatment failure if one of the above classes of drugs is used. Detection of ESBLs can be difficult because they have different levels of activity against various cephalosporins. Thus genetic identification of the exact enzyme can facilitate selection of the optimal antimicrobial agent, which is critical to determine the most effective treatment response.

First-generation cephalosporins include cefalexin, cefaloridine, cefalotin, cefazolin, cefadroxil, cefazedone, cefatrizine, cefapirin, cefradine, cefacetrile, cefrodaxine, ceftezole. Second-generation cephalosporins include cefoxitin, cefuroxime, cefamandole, cefaclor, cefotetan, cefonicide, cefotiam, loracarbef, cefmetazole, cefprozil, ceforanide. Third-generation cephalosporins include cefotaxime, ceftazidime, cefsulodine, ceftriaxone, cefmenoxime, latamoxef, ceftizoxime, cefixime, cefodizime, cefetamet, cefpiramide, cefoperazone, cefpodoxime, ceftibuten, cefdinir, cefditoren, ceftriaxone, cefoperazone, cefbuperazone. Fourth-generation cephalosporins include cefepime and cefpirome.

β-lactamase producing bacteria may include Gram-negative bacteria such as those found in the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella, Aeromonas, Moraxella, Pasteurella, Providencia* and *Legionella*.

Antibiotic resistance is intended to mean any type of mechanism which allows a microorganism to render a treatment partially or completely ineffective on the microorganism, guaranteeing its survival. β-lactam antibiotic resistance is intended to mean any type of β-lactamase-based mechanism which allows a microorganism to render a treatment partially or completely ineffective on the microorganism, guaranteeing its survival. For example, wherein the mechanism is related to the expression of an enzyme belonging to the β-lactamase group including extended-spectrum β-lactamase or of an enzyme belonging to the group of class C cephalosporinases.

Biological sample is intended to mean a clinical sample, derived from a specimen of biological fluid, or a food sample, derived from any type of food or drink, or from an agricultural source, such as animals, soil, water, or air, or from a surface such as with a biofilm. This sample may thus be liquid or solid. For example the biological sample may be a clinical sample of blood, plasma, urine or feces, or of rectal, nose, throat, skin, wound or cerebrospinal fluid specimens.

The present teachings relate to assays and methods for detecting resistance to beta-lactam antibiotics. The present teachings may detect β-lactamase gene targets which are chromosomally encoded and/or plasmid mediated. The present teachings provide for the detection of family specific gene targets relating to β-lactamase genes including AmpC β-lactamases. The β-lactamase genes detected with the present teachings may include those classified into molecular groups A through D. The β-lactamase genes detected with the present teachings may include those classified into functional groups 1 through 3.

The present teachings relate to assays and methods for detecting resistance of one or more gene beta lactamase gene families including like genes. A like gene may be a beta-lactamase that has one or more of the following: similar amino acid sequence, similar function and similar antibiotic susceptibility profiles. A like gene may be considered as like the target gene detected with the present teachings. For example, OXA-48-like enzymes may include: OXA-48, OXA-48b, OXA-162, OXA-163, OXA-181, OXA-199, OXA-204, OXA-232, OXA-244, OXA-245 and OXA-24.

The present teachings provide one or more primers and/or probes for the identification of one or more β-lactamase genes selected from the group consisting of: CMY, CTX-M, OXA, IMP, VIM, DHA, KPC, MOX, ACC, FOX, EBC, NDM, TEM, and SHV. The present teachings provide one or more primers and/or probes for the identification of β-lactamase genes selected from the group consisting of one or more of the following: MOX-like, FOX-like, ACC-like, EBC-like, CMY-2-like, DHA-like, CTX-M-14-like, CTX-M-15-like, VIM-like, NDM-like, IMP-like, KPC-like, and OXA-48-like, OXA-51-like, OXA-143-like, OXA-58-like, OXA-23-like, OXA-24/40-like, TEM-like, and SHV-like. The present teachings provide one or more primers and/or probes for the identification of a non-beta lactamase gene family which confers antibiotic resistance. For example, one or more primers and/or probes for the identification of MCR gene variants. The primers and/or probes of the present teachings may be included in one or more kits. The one or more kits may be used for identification with any of the following: polymerase chain reaction, microarray, NGS-based target enrichment, and/or mass spectrometric characterization.

Exemplary sequences for primers and probes for of the present teachings are depicted in Table 1. [SEQ. ID NOS 67-260] Primers and/or probes may be degenerate at any nucleotide position. Primers and/or probes may not be degenerate at any nucleotide position. Any suitable fluorophore and/or quencher and nucleic acid sequence combination may be used. For example, a probe may be labeled with a fluorescent tag at one end and a fluorescent quencher at the other end. For example, a probe may be labeled with a fluorescent tag at one end and a fluorescent quencher at the other end. For example, two fluorescent quenchers may be included at one end or within the probe sequence. It is contemplated that the probe sequences of the present teachings may be labeled with any suitable fluorophore and quencher combinations. For example, any fluorophore of the present teachings may be attached to any probe DNA sequence of the present teachings.

TABLE 1

| | Primer/Probe Sequence |
|---|---|
| SEQ ID NO. 67 | TGGCCAGAACTGACAGGCAAA |
| SEQ ID NO. 68 | TTTCTCCTGAACGTGGCTGGC |
| SEQ ID NO. 69 | 56-FAM/ACGCTAACT/ZEN/CCAGCATTGGTCTGT/3IABkFQ/ |
| SEQ ID NO. 70 | CCGTCACGCTGTTGTTAGG |
| SEQ ID NO. 71 | GCTGTGTTAATCAATGCCACAC |
| SEQ ID NO. 72 | 5HEX/AACTTGCCG/ZEN/AATTAGAGCRGCAGT/3IABkFQ |
| SEQ ID NO. 73 | CGTTTCGTCTGGATCGCAC |
| SEQ ID NO. 74 | GCTGGGTAAAATAGGTCACC |
| SEQ ID NO. 75 | 5TEX615/TATCATTGGTGGTGCCGTAGTCGC/3IAbRQSp |
| SEQ ID NO. 76 | GAGAGGATGAYCAGCCACAC |
| SEQ ID NO. 77 | CGCCCATTGTSCAATATTCC |
| SEQ ID NO. 78 | 5TYE665/TGAGACACGGTCCAGACTCCTACG/3IAbRQSp |
| SEQ ID NO. 79 | AATCACAGGGCGTAGTTGTG |
| SEQ ID NO. 80 | ACCCACCAGCCAATCTTAGG |
| SEQ ID NO. 81 | 56-FAM/TAGCTTGAT/ZEN/CGCCCTCGATTTGGG/3IABkFQ/ |
| SEQ ID NO. 82 | GCGGAGTTAACTATTGGCTAG |
| SEQ ID NO. 83 | GGCCAAGCTTCTATATTTGCG |
| SEQ ID NO. 84 | 5HEX/TTRTTYGGT/ZEN/GGTTGYTTTRTTAA/3IABkFQ |
| SEQ ID NO. 85 | GCGGAGTTARYTATTGGCTAG |
| SEQ ID NO. 86 | GGCCAAGCYTCTAWATTTGCG |
| SEQ ID NO. 87 | /5HEX/CCGGACGGT/ZEN/CTTGGTAATTTGGGT/3IABkFQ/ |
| SEQ ID NO. 88 | /5HEX/CCGTACGGT/ZEN/TTAGGCAATTTGGGT/3IABkFQ/ |
| SEQ ID NO. 89 | GGCGGCGTTGATGTCCTTCG |
| SEQ ID NO. 90 | CCATTCAGCCAGATCGGCATC |
| SEQ ID NO. 91 | 5TEX615/AGCTCTTCTATCCTGGTGCTGCG/3IAbRQSp |
| SEQ ID NO. 92 | AACTTTCACAGGTGTGCTGGGT |
| SEQ ID NO. 93 | CCGTACGCATACTGGCTTTGC |
| SEQ ID NO. 94 | 56-FAM/AAACCGGGC/ZEN/GATATGCGTCTGTAT/3IABkFQ/ |
| SEQ ID NO. 95 | GTATCGCCGTCTAGTTCTGC |
| SEQ ID NO. 96 | CCTTGAATGAGCTGCACAGTGG |
| SEQ ID NO. 97 | 5HEX/TCGTCGCGG/ZEN/AACCATTCGCTAAA/3IABkFQ/ |
| SEQ ID NO. 98 | GTTTGATCGTCAGGGATGGC |
| SEQ ID NO. 99 | GGCGAAAGTCAGGCTGTG |
| SEQ ID NO. 100 | 5TEX615/CATCAGGACAAGATGGGCGGTATG/3IAbRQSp |
| SEQ ID NO. 101 | GCTGCTCAAGGAGCACAGGAT |
| SEQ ID NO. 102 | CACATTGACATAGGTGTGGTGC |

TABLE 1-continued

| | Primer/Probe Sequence |
|---|---|
| SEQ ID NO. 103 | 56-FAM/AGGATGGCA/ZEN/AGGCCCACTATTTCA/3IABkFQ |
| SEQ ID NO. 104 | AACAGCCTCAGCAGCCGGTTA |
| SEQ ID NO. 105 | TTCGCCGCAATCATCCCTAGC |
| SEQ ID NO. 106 | 5HEX/AGCCATTAC/ZEN/GTTCCAGAGTTGCGT/3IABkFQ |
| SEQ ID NO. 107 | GCCGAGGCTTACGGGATCAAG |
| SEQ ID NO. 108 | CAAAGCGCGTAACCGGATTGG |
| SEQ ID NO. 109 | 5TEX615/TCTGCTGAAGTTTRYCGAGGCMAA/3IAbRQSp |
| SEQ ID NO. 110 | AACTTTCACAGGTGTGCTGGGT |
| SEQ ID NO. 111 | CCGTACGCATACTGGCTTTGC |
| SEQ ID NO. 112 | 56-FAM/AAACCGGGC/ZEN/GATATGCGTCTGTAT/3IABkFQ/ |
| SEQ ID NO. 113 | CTGGGTTCTATAAGTAAAACCTTCACCGG |
| SEQ ID NO. 114 | CTTCCACTGCGGCTGCCAGTT |
| SEQ ID NO. 115 | 5HEX/GATGCCATT/ZEN/GCYCGSGGTGAAAT/3IABkFQ |
| SEQ ID NO. 116 | CCGAAGCCTATGGCGTGAAATCC |
| SEQ ID NO. 117 | GCAATGCCCTGCTGGAGCG |
| SEQ ID NO. 118 | 5TEX615/ATGTTGGCCTGAACCCAGCG/3IAbRQSp |
| SEQ ID NO. 119 | AGCACATACAGAATATGTCCCTGC |
| SEQ ID NO. 120 | ACCTGTTAACCAACCTACTTGAGGG |
| SEQ ID NO. 121 | /56-FAM/TTGCAAGACGGACTGGCTTAGACC/3BHQ_1/ |
| SEQ ID NO. 122 | CCTGATCGGATTGGAGAACC |
| SEQ ID NO. 123 | CTACCTCTTGAATAGGCGTAACC |
| SEQ ID NO. 124 | /5TEX615/ACGTCGCGCAAGTTCCTGATAGAC/3IAbRQSp/ |
| SEQ ID NO. 125 | TAGTGACTGCTAATCCAAATCACAG |
| SEQ ID NO. 126 | GCACGAGCAAGATCATTACCATAGC |
| SEQ ID NO. 127 | /5HEX/AGTTATCCAACAAGGCCAAACTCAACA/3BHQ_1/ |
| SEQ ID NO. 128 | AATCACAGGGCGTAGTTGTG |
| SEQ ID NO. 129 | ACCCACCAGCCAATCTTAGG |
| SEQ ID NO. 130 | /5HEX/TAGCTTGATCGCCCTCGATTTGGG/3BHQ_1/ |
| SEQ ID NO. 131 | GTGGGATGGAAAGCCACG |
| SEQ ID NO. 132 | CACTTGCGGGTCTACAGC |
| SEQ ID NO. 133 | /56-FAM/TTACTTTGGGCGAAGCCATGCAAG/3BHQ_1/ |
| SEQ ID NO. 134 | CACCTATGGTAATGCTCTTGC |
| SEQ ID NO. 135 | CTGGAACTGCTGACAATGCC |
| SEQ ID NO. 136 | /5TEX615/TGGGAGAAAGATATGACTTTAGGTGAGGCA/3IAbRQSp/ |
| SEQ ID NO. 137 | CCGTGTATGTTCAGCTAT |
| SEQ ID NO. 138 | CTTATCCATCACGCCTTT |
| SEQ ID NO. 139 | /5TEX615/TATGATGTCGATACCGCCAAATACCA/3IAbRQSp/ |
| SEQ ID NO. 140 | CTGTATGTCAGCGATCAT |
| SEQ ID NO. 141 | GATGCCAGTTTGCTTATCC |

TABLE 1-continued

| | Primer/Probe Sequence |
|---|---|
| SEQ ID NO. 142 | /56FAM/AAGTCTGGG/ZEN/TGAGAACGGTGTCTAT/3IABkFQ |
| SEQ ID NO. 143 | CAGTCAGTATGCGAGTTTC |
| SEQ ID NO. 144 | AAAATTCGCCAAGCCATC, |
| SEQ ID NO. 145 | /5HEX/TGCATAAGC/ZEN/CAGTGCGTTTTTATAT/3IABkFQ |
| SEQ ID NO. 146 | AGATCAGTTGGGTGCACG |
| SEQ ID NO. 147 | TGCTTAATCAGTGAGGCACC |
| SEQ ID NO. 148 | /56-FAM/ATGAAGCCA/ZEN/TACCAAACGACGAGC/3IABkFQ/ |
| SEQ ID NO. 149 | CTGGAGCGAAAGATCCACTA |
| SEQ ID NO. 150 | ATCGTCCACCATCCACTG |
| SEQ ID NO. 151 | /5HEX/CCAGATCGG/ZEN/CGACAACGTCACC/3IABkFQ/ |
| SEQ ID NO. 152 | TGGCCAGAACTGACAGGCAAA |
| SEQ ID NO. 153 | TTTCTCCTGAACGTGGCTGGC |
| SEQ ID NO. 154 | 56-FAM/ACGCTAACT/ZEN/CCAGCATTGGTCTGT/3IABkFQ/ |
| SEQ ID NO. 155 | CCGTCACGCTGTTGTTAGG |
| SEQ ID NO. 156 | GCTGTGTTAATCAATGCCACAC |
| SEQ ID NO. 157 | 5HEX/AACTTGCCG/ZEN/AATTAGAGCRGCAGT/3IABkFQ |
| SEQ ID NO. 158 | CGTTTCGTCTGGATCGCAC |
| SEQ ID NO. 159 | GCTGGGTAAAATAGGTCACC |
| SEQ ID NO. 160 | 5TEX615/TATCATTGGTGGTGCCGTAGTCGC/3IAbRQSp |
| SEQ ID NO. 161 | GAGAGGATGAYCAGCCACAC |
| SEQ ID NO. 162 | CGCCCATTGTSCAATATTCC |
| SEQ ID NO. 163 | 5TYE665/TGAGACACGGTCCAGACTCCTACG/3IAbRQSp |
| SEQ ID NO. 164 | AATCACAGGGCGTAGTTGTG |
| SEQ ID NO. 165 | ACCCACCAGCCAATCTTAGG |
| SEQ ID NO. 166 | 56-FAM/TAGCTTGAT/ZEN/CGCCCTCGATTTGGG/13IABkFQ/ |
| SEQ ID NO. 167 | GCGGAGTTAACTATTGGCTAG |
| SEQ ID NO. 168 | GGCCAAGCTTCTATATTTGCG |
| SEQ ID NO. 169 | 5HEX/TTRTTYGGT/ZEN/GGTTGYTTTRTTAA/3IABkFQ |
| SEQ ID NO. 170 | GCGGAGTTARYTATTGGCTAG |
| SEQ ID NO. 171 | GGCCAAGCYTCTAWATTTGCG |
| SEQ ID NO. 172 | /5HEX/CCGGACGGT/ZEN/CTTGGTAATTTGGGT/3IABkFQ/ |
| SEQ ID NO. 173 | /5HEX/CCGTACGGT/ZEN/TTAGGCAATTTGGGT/3IABkFQ |
| SEQ ID NO. 174 | GGCGGCGTTGATGTCCTTCG |
| SEQ ID NO. 175 | CCATTCAGCCAGATCGGCATC |
| SEQ ID NO. 176 | 5TEX615/AGCTCTTCTATCCTGGTGCTGCG/3IAbRQSp |
| SEQ ID NO. 177 | GAGAGGATGAYCAGCCACAC |
| SEQ ID NO. 178 | CGCCCATTGTSCAATATTCC |
| SEQ ID NO. 179 | 5TYE665/TGAGACACGGTCCAGACTCCTACG/3IAbRQSp |
| SEQ ID NO. 180 | AACTTTCACAGGTGTGCTGGGT |

TABLE 1-continued

| | Primer/Probe Sequence |
|---|---|
| SEQ ID NO. 181 | CCGTACGCATACTGGCTTTGC |
| SEQ ID NO. 182 | 56-FAM/AAACCGGGC/ZEN/GATATGCGTCTGTAT/3IABkFQ/ |
| SEQ ID NO. 183 | GTATCGCCGTCTAGTTCTGC |
| SEQ ID NO. 184 | CCTTGAATGAGCTGCACAGTGG |
| SEQ ID NO. 185 | 5HEX/TCGTCGCGG/ZEN/AACCATTCGCTAAA/3IABkFQ/ |
| SEQ ID NO. 186 | GTTTGATCGTCAGGGATGGC |
| SEQ ID NO. 187 | GGCGAAAGTCAGGCTGTG |
| SEQ ID NO. 188 | 5TEX615/CATCAGGACAAGATGGGCGGTATG/3IAbRQSp |
| SEQ ID NO. 189 | GAGAGGATGAYCAGCCACAC |
| SEQ ID NO. 190 | CGCCCATTGTSCAATATTCC |
| SEQ ID NO. 191 | 5TYE665/TGAGACACGGTCCAGACTCCTACG/3IAbRQSp |
| SEQ ID NO. 192 | GCTGCTCAAGGAGCACAGGAT |
| SEQ ID NO. 193 | CACATTGACATAGGTGTGGTGC |
| SEQ ID NO. 194 | 56-FAM/AGGATGGCA/ZEN/AGGCCCACTATTTCA/3IABkFQ |
| SEQ ID NO. 195 | AACAGCCTCAGCAGCCGGTTA |
| SEQ ID NO. 196 | TTCGCCGCAATCATCCCTAGC |
| SEQ ID NO. 197 | 5H EX/AGCCATTAC/ZEN/GTTCCAGAGTTGCGT/3IABkFQ |
| SEQ ID NO. 198 | GCCGAGGCTTACGGGATCAAG |
| SEQ ID NO. 199 | CAAAGCGCGTAACCGGATTGG |
| SEQ ID NO. 200 | 5TEX615/TCTGCTGAAGTTTRYCGAGGCMAA/3IAbRQSp |
| SEQ ID NO. 201 | GAGAGGATGAYCAGCCACAC |
| SEQ ID NO. 202 | CGCCCATTGTSCAATATTCC |
| SEQ ID NO. 203 | 5TYE665/TGAGACACGGTCCAGACTCCTACG/3IAbRQSp |
| SEQ ID NO. 204 | AACTTTCACAGGTGTGCTGGGT |
| SEQ ID NO. 205 | CCGTACGCATACTGGCTTTGC |
| SEQ ID NO. 206 | 56-FAM/AAACCGGGC/ZEN/GATATGCGTCTGTAT/3IABkFQ |
| SEQ ID NO. 207 | CTGGGTTCTATAAGTAAAACCTTCACCGG |
| SEQ ID NO. 208 | CTTCCACTGCGGCTGCCAGTT |
| SEQ ID NO. 209 | 5HEX/GATGCCATT/ZEN/GCYCGSGGTGAAAT/3IABkFQ |
| SEQ ID NO. 210 | CCGAAGCCTATGGCGTGAAATCC |
| SEQ ID NO. 211 | GCAATGCCCTGCTGGAGCG |
| SEQ ID NO. 212 | 5TEX615/ATGTTGGCCTGAACCCAGCG/3IAbRQSp |
| SEQ ID NO. 213 | GAGAGGATGAYCAGCCACAC |
| SEQ ID NO. 214 | CGCCCATTGTSCAATATTCC |
| SEQ ID NO. 215 | 5TYE665/TGAGACACGGTCCAGACTCCTACG/3IAbRQSp |
| SEQ ID NO. 216 | AGCACATACAGAATATGTCCCTGC |
| SEQ ID NO. 217 | ACCTGTTAACCAACCTACTTGAGGG |
| SEQ ID NO. 218 | /56-FAM/TTGCAAGACGGACTGGCTTAGACC/3BHQ_1/ |
| SEQ ID NO. 219 | CCTGATCGGATTGGAGAACC |

TABLE 1-continued

| | Primer/Probe Sequence |
|---|---|
| SEQ ID NO. 220 | CTACCTCTTGAATAGGCGTAACC |
| SEQ ID NO. 221 | /5TEX615/ACGTCGCGCAAGTTCCTGATAGAC/3IAbRQSp/ |
| SEQ ID NO. 222 | TAGTGACTGCTAATCCAAATCACAG |
| SEQ ID NO. 223 | GCACGAGCAAGATCATTACCATAGC |
| SEQ ID NO. 224 | /5HEX/AGTTATCCAACAAGGCCAAACTCAACA/3BHQ_1/ |
| SEQ ID NO. 225 | GAGAGGATGAYCAGCCACAC |
| SEQ ID NO. 226 | CGCCCATTGTSCAATATTCC |
| SEQ ID NO. 227 | 5TYE665/TGAGACACGGTCCAGACTCCTACG/3IAbRQSp |
| SEQ ID NO. 228 | AATCACAGGGCGTAGTTGTG |
| SEQ ID NO. 229 | ACCCACCAGCCAATCTTAGG |
| SEQ ID NO. 230 | /5HEX/TAGCTTGATCGCCCTCGATTTGGG/3BHQ_1/ |
| SEQ ID NO. 231 | GTGGGATGGAAAGCCACG |
| SEQ ID NO. 232 | CACTTGCGGGTCTACAGC |
| SEQ ID NO. 233 | /56-FAM/TTACTTTGGGCGAAGCCATGCAAG/3BHQ_1/ |
| SEQ ID NO. 234 | CACCTATGGTAATGCTCTTGC, |
| SEQ ID NO. 235 | CTGGAACTGCTGACAATGCC |
| SEQ ID NO. 236 | /5TEX615/TGGGAGAAAGATATGACTTTAGGTGAGGCA/3IAbRQSp/ |
| SEQ ID NO. 237 | GAGAGGATGAYCAGCCACAC |
| SEQ ID NO. 238 | CGCCCATTGTSCAATATTCC |
| SEQ ID NO. 239 | 5TYE665/TGAGACACGGTCCAGACTCCTACG/3IAbRQSp |
| SEQ ID NO. 240 | AGATCAGTTGGGTGCACG |
| SEQ ID NO. 241 | TGCTTAATCAGTGAGGCACC |
| SEQ ID NO. 242 | /56-FAM/ATGAAGCCA/ZEN/TACCAAACGACGAGC/3IABkFQ/ |
| SEQ ID NO. 243 | CTGGAGCGAAAGATCCACTA |
| SEQ ID NO. 244 | ATCGTCCACCATCCACTG |
| SEQ ID NO. 245 | /5HEX/CCAGATCGG/ZEN/CGACAACGTCACC/3IABkFQ/ |
| SEQ ID NO. 246 | GAGAGGATGAYCAGCCACAC |
| SEQ ID NO. 247 | CGCCCATTGTSCAATATTCC |
| SEQ ID NO. 248 | 5TYE665/TGAGACACGGTCCAGACTCCTACG/3IAbRQSp |
| SEQ ID NO. 249 | CCGTGTATGTTCAGCTAT |
| SEQ ID NO. 250 | CTTATCCATCACGCCTTT |
| SEQ ID NO. 251 | /5TEX615/TATGATGTCGATACCGCCAAATACCA/3IAbRQSp/ |
| SEQ ID NO. 252 | CTGTATGTCAGCGATCAT |
| SEQ ID NO. 253 | GATGCCAGTTTGCTTATCC |
| SEQ ID NO. 254 | /56FAM/AAGTCTGGG/ZEN/TGAGAACGGTGTCTAT/3IABkFQ/ |
| SEQ ID NO. 255 | CAGTCAGTATGCGAGTTTC |
| SEQ ID NO. 256 | AAAATTCGCCAAGCCATC |
| SEQ ID NO. 257 | /5HEX/TGCATAAGC/ZEN/CAGTGCGTTTTTATAT/3IABkFQ/ |
| SEQ ID NO. 258 | GAGAGGATGAYCAGCCACAC |

TABLE 1-continued

| | Primer/Probe Sequence |
|---|---|
| SEQ ID NO. 259 | CGCCCATTGTSCAATATTCC |
| SEQ ID NO. 260 | 5TYE665/TGAGACACGGTCCAGACTCCTACG/3IAbRQSp |

The present teachings provide a molecular assay. The present teachings may provide a qualitative (i.e. end point) molecular assay for the detection of family-specific KPC, ESBL, MBL, and ampC gene targets. The present teachings may provide a qualitative (i.e. end point) molecular assay for the detection of family-specific plasmid-mediated ampC β-lactamase genes. The present teachings may provide a qualitative (i.e. end point) molecular assay for the detection of OXA gene targets. Fluorescently-labeled DNA probes may be used for detection. The assay of the present teachings may provide for differentiation between a plasmid-mediated ampC β-lactamase gene from a chromosomal ampC β-lactamase gene; provided the two genes are not from the same chromosomal origin. The assay may involve extraction of DNA from bacterial cells. The assay may include subsequent PCR amplification. The assay may include gel-based detection.

In contrast, to traditional phenotypic methods which require 24-48 hours for data, the present teachings may provide for data generation in just hours or one hour. The total time required for DNA extraction, PCR set-up, amplification, and analysis may be around about 2 hours to about 3 hours. The sensitivity of the assay may be about 100%. The specificity of the assay may be about 100%. Therefore, the present teachings provide for fast and reliable detection. Implementation of such rapid assays have a positive impact for infection control and patient care.

The present teachings allow for the detection of multiple β-lactamase gene families. The β-lactamases may include all major β-lactamases including ampC types. For example, the present teachings may allow for identification of up to six to nine β-lactamase gene families. The β-lactamase gene families may include CMY, CTX-Ms, DHA, IMP, KPC, NDM, OXA and VIM. The AmpC β-lactamases gene families may include MOX, ACC, FOX, DHA, CMY and EBC.

The present teachings provide for a kit which allows for identification of at least nine β-lactamase gene families. The gene families may include: IMP-1-like, NDM-like, OXA-48-like, CTX-M-14-like, CTX-M-15-like, CMY-2-like, DHA-like, VIM-like, and KPC-like. The kit may also include an endogenous internal control (IC) that targets a conserved region common in gram-negative bacteria to reduce false negatives due to PCR inhibition, DNA degradation, or poor extraction. It is contemplated that the endogenous internal control discriminates false negative samples from true negative samples due to but not limited to one or more of PCR inhibition, DNA degradation, and/or poor extraction. The kit may utilize sequence-specific primer pairs for the PCR amplification of each target group. The kit may utilize fluorescently-labeled, target-specific DNA probes for detection by real-time PCR.

The kit may include one or more multiplex primer-probe mixes containing one or more primers and one or more probes. The multiplex primer-probe mix may be a 10×PCR mix. In one example, the kit includes three multiplex primers-probes mix vials. The mix vials may provide for simultaneous real-time PCR amplification of all targets between three reaction tubes. PCR Mix 1 may amplify a first set of three gene families. For example, CMY-2, CTX-M-14, and CTX-M-15. PCR Mix 2 may amplify a second set of three gene families. For example, OXA-48, IMP, and VIM. PCR mix 3 may amplify a third set of gene families. For example, DHA, KPC, and NDM. The multiplex mix may also include an internal control (IC) in each mix. The kit may include three external DNA control vials or first control mix vial, a second control mix vial and a third control mix vial. The DNA control mix vial may contain synthetic DNA templates of the corresponding multiplex targets. The DNA control mixes may serve as a positive control for each multiplex reaction. The DNA control mix may contain stabilized bacteria with chromosomal or transmissible genetic elements in a sample matrix similar to a patient sample.

The present teachings provide for a kit which allows for identification of at least six plasmid-mediated ampC gene families. The gene families may include: MOX-like, DHA-like, ACC-like, EBC-like, FOX-like, and CMY-2-like. The kit may also include an endogenous internal control (IC) that targets a conserved region common in gram-negative bacteria to reduce false negatives due to PCR inhibition, DNA degradation, or poor extraction. It is contemplated that the endogenous internal control discriminates false negative samples from true negative samples due to but not limited to one or more of PCR inhibition, DNA degradation, and/or poor extraction. The kit may utilize sequence-specific primer pairs for the PCR amplification of each family. The kit may utilize fluorescently-labeled, target-specific DNA probes for detection by real-time PCR.

The kit may include one or more multiplex primer-probe mixes containing one or more primers and one or more probes. The multiplex primer-probe mix may be a 10×PCR mix. In one example, the kit includes two multiplex primers-probes mix vials. The mix vials may provide for simultaneous real-time PCR amplification of all targets between two reaction tubes. PCR Mix 1 may amplify a first set of three gene families. For example, MOX, ACC and FOX. PCR Mix 2 may amplify a second set of three gene families. For example, DHA, EBC and CMY-2. The multiplex mix may also include an internal control (IC) in each mix. The kit may include two external DNA control vials or first control mix vial and a second control mix vial. The DNA control mix vial may contain synthetic DNA templates of the corresponding multiplex targets. The DNA control mixes may serve as a positive control for each multiplex reaction.

The present teachings provide for a kit which allows for identification of at least six OXA carbapenemase gene families. The gene families may include: OXA-23, OXA-24/40, OXA-48, OXA-51, OXA-58, and OXA-143. The gene families may include like gene families. The kit may also include an endogenous internal control (IC) that targets a conserved region common in gram-negative bacteria to reduce false negatives due to PCR inhibition, DNA degradation, or poor extraction. It is contemplated that the endogenous internal control discriminates false negative samples from true negative samples due to but not limited to one or more of PCR inhibition, DNA degradation, and/or poor extraction. The kit may utilize sequence-specific primer pairs for the PCR amplification of each family. The kit may utilize fluorescently-labeled, target-specific DNA probes for detection by real-time PCR.

The kit may include one or more multiplex primer-probe mixes containing one or more primers and one or more probes. The multiplex primer-probe mix may be a 10×PCR mix. In one example, the kit includes two multiplex primers-probes mix vials. The mix vials may provide for simultaneous real-time PCR amplification of all targets between two reaction tubes. PCR Mix 1 may amplify a first set of three gene families. For example, OXA 143, OXA 23 and OXA 51. PCR Mix 2 may amplify a second set of three gene families. For example, OXA 24/40, OXA-48 and OXA-58. The multiplex mix may also include an internal control (IC) in each mix. The kit may include two external DNA control vials or first control mix vial and a second control mix vial. The DNA control mix vial may contain synthetic DNA templates of the corresponding multiplex targets. The DNA control mixes may serve as a positive control for each multiplex reaction.

In addition, the present teachings contemplate that the kit or kits of the present teachings may provide for the detection of a non-beta lactamase gene family. The kit or kits may provide for detection of plasmid-mediated mechanisms of antibiotic resistance for one more types/categories of antibiotics. For example, the kit may also provide for the detection of the MCR-1 gene which confers polymixin resistance. The kit or kits may include primer sequences, probe sequences, and a control sequence for detection of one or more non-beta lactamase gene family in addition to beta-lactamase genes. For example, a kit may provide for the detection of ampC genes families and a MCR-1 gene family.

Furthermore, the present teachings allow for the expansion of the detection of other β-lactamase gene families including TEM and SHV. The gene families may include like gene families. The kit may also include an endogenous internal control (IC) that targets a conserved region common in gram-negative bacteria to reduce false negatives due to PCR inhibition, DNA degradation, or poor extraction. It is contemplated that the endogenous internal control discriminates false negative samples from true negative samples due to but not limited to one or more of PCR inhibition, DNA degradation, and/or poor extraction. The kit may utilize sequence-specific primer pairs for the PCR amplification of each family. The kit may utilize fluorescently-labeled, target-specific DNA probes for detection by real-time PCR.

The kit or kits of the present teachings may include synthetic DNA oligonucleotide primers, target-specific DNA probes and DNA controls for the specified gene targets suspended in TE buffer, pH 8.0. The contents of the kit may be enclosed in vials. For example, the one or more 10×PCR mixes may be comprised of 275 μL. For example, the one or more control mixes may be comprised of 14 μL. For example, the contents of the kit may be sufficient for about 100 reactions total and about 12 reactions of the control DNA mix.

Detection of each target is based on the optical fluorescence of the fluorophore conjugated to each target-specific DNA probe. Any suitable fluorophore and nucleic acid sequence combination may be used. For example, the fluorophores may be selected from the group consisting of: FAM (6-Carboxyfluorescein), HEX (Hexachlorofluorescein), TEX615 and TYE665.

The present teachings provide assays for the detection of β-lactamase gene families from a biological sample. The assays may be included in a kit or kits. The kit may provide for the detection of β-lactamase by various molecular biology technologies and platforms. The kit may include one or more primers and/or probes for the identification by polymerase chain reaction or microarray of one or more β-lactamase genes selected from the group consisting of: CMY, CTX-M, OXA, IMP, VIM, DHA, KPC, MOX, ACC, FOX, EBC, NDM, TEM, and SHV.

The kit may include one or more primers and/or probes for the identification by polymerase chain reaction or microarray of a non-beta lactamase gene family which confers antibiotic resistance. The kit may include one or more primers and/or probes for the identification by polymerase chain reaction or microarray of one or more MCR genes. The kit may include one or more primers and/or probes for the identification by polymerase chain reaction or microarray of a MCR-1 gene.

The kit may provide for detection of specified targets from crude biological samples such as blood, urine, plasma, feces, sputum, etc. The kit may provide for detection of specified targets directly from or extracted directly from crude biological samples including but not limited to blood, blood cultures, urine, plasma, feces, fecal swabs, peri-rectal/peri-anal swabs, sputum, and bacterial cultures.

The kit may be used for detection of specified targets from purified nucleic acid samples. The kit may be used for any nucleic acid amplification methodology. The kit may be used with conventional polymerase chain reaction. The kit may be used with real-time polymerase chain reaction. The kit may be used with digital droplet polymerase chain reaction. The kit may be used with detection by microarray technology. The kit may be used with fluorescence and/or infra-red probe-based detection chemistries. The kit may be used with intercalating dye-based detection chemistries. The kit may be used for detection of nucleic acid polymerase chain reaction amplicons ranging from 25 base pairs to 2000 base pairs.

The kit may include various reagents. The various reagents may be contained in various vials. The kit may include a primer set or primer sets. The primer set or primer sets may be labeled or unlabeled with a tracking dye or fluorophore. The kit may include probes. The kit may include a primer-probe mix. The kit may include controls. The kit may include magnesium chloride. The kit may include dNTPs. The kit may include DNA polymerase. The kit may include a tracking dye. The kit may include a composition containing a tracking dye. The kit may include a written protocol. The kit may include a customized master mix in a single tube, two tubes, three tubes, or four tubes containing all chemicals and enzymes necessary to run the PCR assay described herein. The kit may include freeze-dried or lyophilized reagents in a single assay tube or multiple assay tubes. The kit may provide for detection of nucleic acid and the kit reagents may be provided in any liquid form, pooled reaction mix, or lyophilized, freeze dried, or cryo-preserved format.

The kit may include a primer set. The primer set may include at least one primer pair. A primer pair may include a forward primer and a reverse primer. The primer set may include one pair of primers. The primer set may include more than one pair of primers. The primer set may include two pairs of primers. The primer set may include three pairs of primers. The primer set may include one to six pairs of primers. The primer set may include one to ten pairs of primers. The primer set may include up to 30 pairs of primers. The primer set may include up to 50 pairs of primers. The primer set may include up to 100 pairs of primers.

The kit may include a primer-probe mix. The primer-probe mix may include a primer set. The primer-probe mix may include one or more probes. Each pair of primers of the primer set may include a probe or set of probes. The primer-probe mix may include a pair of internal control primers. The pair of internal control primers may include a forward primer and a reverse primer. The primer-probe mix may include an internal control probe.

For example, a primer-probe mix may include one or more pairs of primers, one associated probe per primer pair and internal controls including a pair of primers and a probe. Preferably, the primer-probe mix is a multiplex mix including more than one pair of primers, a probe for each primer pair and internal controls. The multiplex mix may be used for the identification of more than one β-lactamase gene family. Each primer pair and probe may detect a different β-lactamase gene family. For example, three primer pairs and their associated three probes may be used for detection of three different β-lactamase gene families.

The DNA concentration range of each primer set in a PCR may be about 1 nM to about 10 μM (10,000 nM). One or more primers may be labeled with a florescent marker as a probe. The DNA concentration of each probe in a PCR may be about 1 nM to about 10,000 nM. The DNA concentration of each probe in a PCR may be about 10 to about 500 nM.

The kit may include at least one control. The kit may include one, two, three or four controls. The kit may include one or more negative controls. The negative control may include nucleic acid known to express a resistance gene other than the target gene of interest. The kit may include one or more positive controls. The one or more positive controls may be internal controls. The positive control may include nucleic acid known to express or contain the resistance gene. The kit may include an endogenous internal control to reduce false negatives due to PCR inhibition, DNA degradation, and/or poor extraction. It is contemplated that the endogenous internal control discriminates false negative samples from true negative samples due to but not limited to one or more of PCR inhibition, DNA degradation, and/or poor extraction. The endogenous internal control may target a conserved nucleotide sequence or sequences common to the Gram-negative bacteria genome. For example, the internal control may detect the 16S rRNA and/or 23S rRNA gene(s). The internal control may detect the 16S and/or 23S rRNA gene for *E. coli, Pseudomonas, Acinetobacter, Klebsiella* and *Salmonella*.

The kit may include control vector in the control vial. One or more μls of the vector control may be added to a 25 μl reaction to get the working concentration. The DNA concentrations for each control vector may be equivalent to 0.1 copy to 2000 copies or 0.0000243 pg/uL to 0.0455 pg/uL. The DNA concentrations for each control vector may be equivalent to 10 copies to 5000 copies or 0.001 pg/uL to 0.5 pg/uL. Control vector concentrations may be as high as $1 \times 10(9)$ copies and any dilution thereof.

The assays of the present teachings may include the use of magnesium chloride. The kit may include magnesium chloride. The assay may be utilized with a concentration of about 2 mM to about 7 mM $MgCl_2$. Preferably, the concentration is about 3.0 mM to about 5.5 mM $MgCl_2$. More preferably, the concentration is 5.0 mM $MgCl_2$ for an assay for the detection of β-lactamase genes. More preferably the concentration is 5.0 mM $MgCl_2$ for an assay for the detection of ampC β-lactamase genes. More, preferably, the concentration is 5 mM $MgCl_2$ for an assay for the detection of OXA genes.

The assays of the present teachings may include the use of DNA polymerase. The kit may include DNA polymerase. The assay may be utilized with a concentration of about 0.25 U/25 ul reaction to about 3 U/25 ul reaction of DNA polymerase. Preferably, the concentration is 1.25 U/25 μl reaction DNA polymerase for an assay for the detection of β-lactamase genes. Preferably the concentration is 1.25 U/25 μl DNA polymerase for an assay for the detection of β-lactamase ampC genes. For example, the present teachings may utilize the PhilisaFAST® DNA polymerase.

The assays and methods of the present teachings may include a PCR cycling protocol. In one example, the cycling protocol comprises (1) 95° C. for 30 s; (2) 95° C. for 1 s; (3) 55° C. for 10 s; (4) 68° C. for 20 s; and repeating steps (2) to (4) for 40 cycles. In one example, the cycling protocol comprises (1) 95° C. for 30 s; (2) 95° C. for 6 s; (3) 66° C. for 10 s; and repeating steps (2) to (3) for 40 cycles. In one example, the cycling protocol includes a hot start of 98° C. for 30 s and 30 cycles of: 98° C. for 5 s, 60° C. for 10 s and 72° C. for 20 s. In one example, the cycling protocol includes using 98° C. for 30 s, followed by 30 cycles of 98° C. for 5 s, 60° C. for 10 s., and 72° C. for 25 s. In one example, the PCR protocols include a detection step where fluorescent signal is measured.

The kit may include one or more of the following: primer, probe and control. A mix of one or more of the following: primer, probe and internal control, may be enclosed in one container. A mix of one or more of the following: primer, probe and internal control, may be enclosed in more than one container. The container may be a vial. In one example, the kit includes 3 DNA control vials and 3 10× primer/probe mix vials. Nine antibiotic resistance gene families and one internal control may be identified with the vials. In one example, the kit includes 2 DNA control vials and 2 10× primer/probe mix vials. Six antibiotic resistance gene families and one internal control may be identified with the vials.

The present teachings allow for detection of the β-lactamase CMY-2 gene family from a biological sample. The present teachings provide for a kit including one or more primers and/or probes for the identification by multiplex real-time polymerase chain reaction of β-lactamase genes including the CMY-2-like gene family. The biological sample may include Gram-negative bacteria such as *Escherichia coli, Proteus mirabilis, Klebsiella pneumoniae, Klebsiella oxytoca, Serratia marcescens, Citrobacter freundii* and other *Citrobacter* species. The CMY-2-like genes detected may include CMY-2, CMY-4, CMY-6, CMY-7, CMY-12, CMY-14, CMY-15, CMY-16, CMY-18, CMY-21, CMY-22, CMY-23, CMY-24, CMY-25, CMY-26, CMY-27, CMY-28, CMY-29, CMY-30, CMY-31, CMY-32, CMY-33, CMY-34, CMY-35, CMY-37, CMY-38, CMY-39, CMY-40, CMY-41, CMY-42, CMY-43, CMY-44, CMY-45, CMY-46, CMY-47, CMY-48, CMY-49, CMY-50, CMY-51, CMY-53, CMY-54, CMY-55, CMY-56, CMY-57, CMY-58, CMY-59, CMY-60, CMY-61, CMY-62, CMY-63, CMY-64, CMY-65, CMY-66, CMY-67, CMY-68, CMY-69, CMY-71, CMY-72, CMY-73, CMY-75, CMY-76, CMY-77, CMY-78, CMY-79, CMY-80, CMY-81, CMY-84, CMY-85, CMY-86, CMY-87, CMY-89, CMY-90, CMY-96, CMY-97, CMY-99, CMY-102, CMY-103, CMY-104, CMY-105, CMY-107, CMY-108, CMY-110, CMY-111, CMY-112, CMY-113, CMY-114, CMY-115, CMY-116, CMY-117, CMY-118, CMY-119, CMY-121, CMY-122, CMY-124, CMY-125, CMY-126, CMY-127, CMY-128, CMY-129, CMY-130, CMY-131, CMY-132, CMY-133 and CMY-135.

The present teachings allow for the detection of the β-lactamase CTX-M gene family from a biological sample.

The present teachings provide for a kit including one or more primers and/or probes for the identification by multiplex real-time polymerase chain reaction of β-lactamase genes including the CTX-M-14-like gene family. The biological sample may include Gram-negative bacteria such as *Klebsiella pneumoniae, Enterobacter cloacae, Escherichia coli, Salmonella enterica, Proteus mirabilis* and *Shigella* species. The CTX-M-14-like genes detected may include CTX-M-9, CTX-M-13, CTX-M-14, CTX-M-16, CTX-M-17, CTX-M-19, CTX-M-21, CTX-M-24, CTX-M-27, CTX-M-38, CTX-M-51, CTX-M-64, CTX-M-65, CTX-M-67, CTX-M-82, CTX-M-83, CTX-M-84, CTX-M-85, CTX-M-86, CTX-M-90, CTX-M-93, CTX-M-98, CTX-M-99, CTX-M-102, CTX-M-104, CTX-M-105, CTX-M-110, CTX-M-111, CTX-M-112, CTX-M-113, CTX-M-121, CTX-M-122, CTX-M-123, CTX-M-125, CTX-M-129, CTX-M-130, CTX-M-132, CTX-M-134, CTX-M-147, CTX-M-148 and CTX-M-159.

The present teachings allow for the detection of the β-lactamase CTX-M gene family from a biological sample. The present teachings provide for a kit including one or more primers and/or probes for the identification by multiplex real-time polymerase chain reaction of β-lactamase genes including the CTX-M-15-like gene family. The biological sample may include Gram-negative bacteria such as *Escherichia coli, Klebsiella pneumoniae, Citrobacter freundii, Shigella* species and *Proteus mirabilis*. The CTX-M-15-like genes detected may include CTX-M-1, CTX-M-3, CTX-M-10, CTX-M-15, CTX-M-22, CTX-M-28, CTX-M-29, CTX-M-30, CTX-M-32, CTX-M-37, CTX-M-55, CTX-M-64, CTX-M-71, CTX-M-103, CTX-M-117, CTX-M-123, CTX-M-132, CTX-M-136, CTX-M-138, CTX-M-142, CTX-M-144, CTX-M-155, CTX-M-156, CTX-M-157, CTX-M-158, CTX-M-163, CTX-M-164, CTX-M-166 and CTX-M-172.

The present teachings allow for the detection of the β-lactamase DHA gene family from a biological sample. The present teachings provide for a kit including one or more primers and/or probes for the identification by multiplex real-time polymerase chain reaction of β-lactamase genes including the DHA-like family. The biological sample may include Gram-negative bacteria such as *Klebsiella pneumoniae, Morganella morganii, Escherichia coli, Enterobacter cloacae, Proteus mirabilis* and *Citrobacter koseri*. The DHA-like genes detected may include DHA-1, DHA-2, DHA-5, DHA-6, DHA-7, DHA-9, DHA-10, DHA-12, DHA-13, DHA-14, DHA-15, DHA-16, DHA-17, DHA-18, DHA-19, DHA-20, DHA-21 and DHA-22.

The present teachings allow for the detection of the β-lactamase IMP gene family from a biological sample. The present teachings provide for a kit including one or more primers and/or probes for the identification by multiplex real-time polymerase chain reaction of β-lactamase genes including the IMP-like family. The biological sample may include Gram-negative bacteria such as *Serratia marcescens, Escherichia coli* and *Pseudomonas aeruginosa*. The IMP-like genes detected may include IMP-1, IMP-2, IMP-3, IMP-4, IMP-5, IMP-6, IMP-7, IMP-8, IMP-9, IMP-10, IMP-13, IMP-14, IMP-15, IMP-16, IMP-18, IMP-19, IMP-20, IMP-22, IMP-24, IMP-25, IMP-26, IMP-27, IMP-28, IMP-30, IMP-32, IMP-33, IMP-34, IMP-37, IMP-38, IMP-40, IMP-42, IMP-45, IMP-48, IMP-49, IMP-51 and IMP-52.

The present teachings allow for the detection of the β-lactamase KPC gene family from a biological sample. The present teachings provide for a kit including one or more primers and/or probes for the identification by multiplex real-time polymerase chain reaction of β-lactamase genes including the KPC-like family. The biological sample may include Gram-negative bacteria such as *Klebsiella pneumoniae, Escherichia coli, Enterobacter cloacae* and other *Enterobacter* species, *Pseudomonas aeruginosa* and *Acinetobacter baumannii*. The KPC-like genes detected may include KPC-1, KPC-2, KPC-3, KPC-4, KPC-5, KPC-6 KPC-7, KPC-8, KPC-9, KPC-10, KPC-11, KPC-13, KPC-14, KPC-15, KPC-16, KPC-17 KPC-18, KPC-19, KPC-21, KPC-22, KPC-47, KPC-56, KPC-63, KPC-272, KPC-484, KPC-629, KPC-727, and KPC-860.

The present teachings allow for the detection of the β-lactamase NDM gene family from a biological sample. The present teachings provide for a kit including one or more primers and/or probes for the identification by multiplex real-time polymerase chain reaction of β-lactamase genes including the NDM-like family. The biological sample may include Gram-negative bacteria such as *Escherichia coli, Acinetobacter baumannii, Enterobacter cloacae* and *Klebsiella pneumoniae*. The NDM-like genes detected may include NDM-1, NDM-2, NDM-3, NDM-4, NDM-5, NDM-6, NDM-7, NDM-8, NDM-9, NDM-10, NDM-11, NDM-12, NDM-13, NDM-15, NDM-16 and NDM-32.

The present teachings allow for the detection of the β-lactamase OXA gene family from a biological sample. The present teachings provide for a kit including one or more primers and/or probes for the identification by multiplex real-time polymerase chain reaction of β-lactamase genes including the OXA-48-like family. The biological sample may include Gram-negative bacteria such as *Klebsiella pneumoniae, Enterobacter cloacae, Shewanella xiamenensis, Escherichia coli* and *Serratia marcescens*. The OXA-48-like genes detected may include OXA-48, OXA-162, OXA-163, OXA-181, OXA-199, OXA-204, OXA-232, OXA-244, OXA-245, OXA-247, OXA-370, OXA-405, OXA-416, OXA-438 and OXA-439.

The present teachings provide for a kit including one or more primers and/or probes for the identification by multiplex real-time polymerase chain reaction of β-lactamase genes including one or more of the following: OXA-143-like, OXA-23-like, OXA-51-like, OXA-48-like, OXA-58-like and OXA24/40-like. The OXA-143-like genes detected may include the following: OXA-143, OXA-182, OXA-231, OXA-253, and OXA-255. The OXA-23-like genes detected may include the following: OXA-23, OXA-27, OXA-49, OXA-73, OXA-102, OXA-103, OXA-105, OXA-133, OXA-134, OXA-146, OXA-165, OXA-166, OXA-167, OXA-168, OXA-169, OXA-170, OXA-171, OXA-225 and OXA-239. The OXA-51-like genes detected may include the following: OXA-51, OXA-64, OXA-65, OXA-66, OXA-67, OXA-68, OXA-69, OXA-70, OXA-71, OXA-75, OXA-76, OXA-77, OXA-78, OXA-79, OXA-80, OXA-82, OXA-83, OXA-84, OXA-86, OXA-87, OXA-88, OXA-89, OXA-90, OXA-91, OXA-92, OXA-93, OXA-94 OXA-95, OXA-98, OXA-99, OXA-100, OXA-104, OXA-106, OXA-107, OXA-108, OXA-109, OXA-110, OXA-111, OXA-112, OXA-113, OXA-115, OXA-116, OXA-117, OXA-120, OXA-121, OXA-122, OXA-123, OXA-124, OXA-125, OXA-126, OXA-127, OXA-128, OXA-130, OXA-131, OXA-132, OXA-138, OXA-144, OXA-148, OXA-149, OXA-150, OXA-172, OXA-173, OXA-174, OXA-175, OXA-176, OXA-177, OXA-178, OXA-179, OXA-180, OXA-194, OXA-195, OXA-196, OXA-197, OXA-200, OXA-201, OXA-202, OXA-203, OXA-206, OXA-208, OXA-216, OXA-217, OXA-219, OXA-223, OXA-241, OXA-242, OXA-248, OXA-249, OXA-250 and OXA-254. The OXA-48-like genes detected may include the following:

OXA-48, OXA-48b, OXA-162, OXA-163, OXA-181, OXA-199, OXA-204, OXA-232, OXA-244, OXA-245 and OXA-247. The OXA-58-like genes may include the following: OXA-58, OXA-96, OXA-97 and OXA-164. The OXA-40-like genes may include the following: OXA-40, OXA-25, OXA-26, OXA-72, OXA-139, OXA-160 and OXA-207.

The present teachings allow for the detection of the β-lactamase VIM gene family from a biological sample. The present teachings provide for a kit including one or more primers and/or probes for the identification by multiplex real-time polymerase chain reaction of β-lactamase genes including the VIM-like family. The biological sample may include Gram-negative bacteria such as *Klebsiella oxytoca, Citrobacter freundii, Klebsiella pneumoniae, Pseudomonas aeruginosa, Escherichia coli* and *Enterobacter cloacae*. The VIM-like genes detected may include VIM-1, VIM-2, VIM-3, VIM-4, VIM-5, VIM-6, VIM-8, VIM-9, VIM-10, VIM-11, VIM-12, VIM-13, VIM-14, VIM-15, VIM-16, VIM-17, VIM-18, VIM-19, VIM-20, VIM-23, VIM-24, VIM-25, VIM-26, VIM-27, VIM-28, VIM-31, VIM-33, VIM-34, VIM-35, VIM-36, VIM-37, VIM-38, VIM-39, VIM-40, VIM-41, VIM-42, VIM-43, VIM-44, VIM-45 and VIM-46.

The present teachings allow for the detection of the AmpC β-lactamase MOX gene family from a biological sample. The present teachings provide for a kit including one or more primers and/or probes for the identification by multiplex real-time polymerase chain reaction of β-lactamase genes including the MOX-like family. The biological sample may include Gram-negative bacteria such as *Klebsiella pneumoniae, Aeromonas punctata/Aeromonas caviae* and other *Aeromonas* species and *Escherichia coli*. The MOX-like genes detected may include MOX-1, MOX-2, MOX-3, MOX-4, MOX-5, MOX-6, MOX-7, MOX-8, MOX-10, CMY-1, CMY-8, CMY-9, CMY-10, CMY-11 and CMY-19.

The present teachings allow for the detection of the AmpC β-lactamase ACC gene family from a biological sample. The present teachings provide for a kit including one or more primers and/or probes for the identification by multiplex real-time polymerase chain reaction of β-lactamase genes including the ACC-like family. The biological sample may include Gram-negative bacteria such as *Salmonella enterica, Escherichia coli, Hafnia alvei* and *Proteus mirabilis*. The ACC-like genes detected may include ACC-1, ACC-2, ACC-4, ACC-5 and ACC-6.

The present teachings allow for the detection of the AmpC β-lactamase FOX gene family from a biological sample. The present teachings provide for a kit including one or more primers and/or probes for the identification by multiplex real-time polymerase chain reaction of β-lactamase genes including the FOX-like family. The biological sample may include Gram-negative bacteria such as *Klebsiella pneumoniae* and *Aeromonas punctata*. The FOX-like genes detected may include FOX-1, FOX-2, FOX-3, FOX-4, FOX-5, FOX-6, FOX-7, FOX-8, FOX-9, FOX-10 and FOX-12.

The present teachings allow for the detection of the AmpC β-lactamase DHA gene family from a biological sample. The present teachings provide for a kit including one or more primers and/or probes for the identification by multiplex real-time polymerase chain reaction of β-lactamase genes including the DHA-like family. The biological sample may include Gram-negative bacteria such as *Klebsiella pneumoniae, Morganella morganii, Escherichia coli* and *Enterobacter cloacae*. The DHA-like genes detected may include DHA-1, DHA-2, DHA-5, DHA-6, DHA-7, DHA-9, DHA-10, DHA-12, DHA-13, DHA-14, DHA-15, DHA-16, DHA-17, DHA-18, DHA-19, DHA-20, DHA-21 and DHA-22.

The present teachings allow for the detection of the AmpC β-lactamase CMY-2 gene family from a biological sample. The present teachings provide for a kit including one or more primers and/or probes for the identification by multiplex real-time polymerase chain reaction of β-lactamase genes including the CMY-2-like family. The biological sample may include Gram-negative bacteria such as *Klebsiella pneumoniae, Morganella morganii, Escherichia coli* and *Enterobacter cloacae*. The CMY-2-like genes detected include CMY-2, CMY-4, CMY-6, CMY-7, CMY-12, CMY-14, CMY-15, CMY-16, CMY-18, CMY-21, CMY-22, CMY-23, CMY-24, CMY-25, CMY-26, CMY-27, CMY-28, CMY-29, CMY-30, CMY-31, CMY-32, CMY-33, CMY-34, CMY-35, CMY-37, CMY-38, CMY-39, CMY-40, CMY-41, CMY-42, CMY-43, CMY-44, CMY-45, CMY-46 CMY-47, CMY-48, CMY-49, CMY-50, CMY-51, CMY-53, CMY-54, CMY-55, CMY-56, CMY-57, CMY-58, CMY-59, CMY-60, CMY-61, CMY-62, CMY-63, CMY-64, CMY-65, CMY-66, CMY-67, CMY-68, CMY-69, CMY-71, CMY-72, CMY-73, CMY-75, CMY-76, CMY-77, CMY-78, CMY-79, CMY-80, CMY-81, CMY-84, CMY-85 CMY-86, CMY-87, CMY-89, CMY-90, CMY-96, CMY-97, CMY-99, CMY-102, CMY-103, CMY-104 CMY-105, CMY-107, CMY-108, CMY-110, CMY-111, CMY-112, CMY-113, CMY-114, CMY-115 CMY-116, CMY-117, CMY-118, CMY-119, CMY-121, CMY-122, CMY-124, CMY-125, CMY-126, CMY-127, CMY-128, CMY-129, CMY-130, CMY-131 CMY-132, CMY-133 and CMY-135.

The present teachings allow for the detection of the AmpC β-lactamase EBC gene family from a biological sample. The present teachings provide for a kit including one or more primers and/or probes for the identification by multiplex real-time polymerase chain reaction of β-lactamase genes including the EBC-like family such as ACT and MIR. The biological sample may include Gram-negative bacteria such as *Enterobacter cloacae, Klebsiella pneumoniae, Enterobacter asburiae, Enterobacter kobei*, and other *Enterobacter* species. The EBC-like genes detected may include ACT-1, ACT-2, ACT-5, ACT-8, ACT-13, ACT-14, ACT-15, ACT-16, ACT-17, ACT-18, ACT-20, ACT-21, ACT-23, ACT-24, ACT-25, ACT-27, ACT-29, ACT-30, ACT-31, ACT-32, ACT-33, ACT-34, ACT-35, ACT-36, ACT-37, ACT-38, MIR-1, MIR-2, MIR-3, MIR-4, MIR-6, MIR-7, MIR-8, MIR-9, MIR-10, MIR-11, MIR-12, MIR-13, MIR-14, MIR-15, MIR-16, MIR-17 and MIR-18.

The present teachings may allow for the detection of the β-lactamase TEM gene family from a biological sample. The present teachings provide for a kit including one or more primers and/or probes for the identification by multiplex real-time polymerase chain reaction of β-lactamase genes including the TEM-like family. The biological sample may include Gram-negative bacteria such as *Klebsiella pneumoniae, Enterobacter cloacae, Shewanella xiamenensis, Escherichia coli* and *Serratia marcescens*. The TEM-like genes detected may include TEM-1, TEM-2, TEM-3, TEM-15, TEM-20, TEM-32, TEM-40, TEM-52, TEM-88, TEM-91, TEM-97, TEM-98, TEM-106, TEM-107, TEM-112, TEM-120, TEM-126, TEM-135, TEM-141, TEM-150, TEM-153, TEM-163, TEM-168, TEM-170, TEM-171, TEM-206, TEM-214, and TEM-220.

The present teachings may allow for the detection of the β-lactamase SHV gene family from a biological sample. The present teachings provide for a kit including one or more primers and/or probes for the identification by multiplex real-time polymerase chain reaction of β-lactamase genes including the SHV-like family. The biological sample may include Gram-negative bacteria such as *Klebsiella pneumoniae, *Enterobacter cloacae, Shewanella xiamenensis, Escherichia coli* and *Serratia marcescens*. The SHV-like genes detected may include SHV-1, SHV-2, SHV-3, SHV-5, SHV-7, SHV-8, SHV-9, SHV-11, SHV-12, SHV-13, SHV-14, SHV-15, SHV-16, SHV-18, SHV-24, SHV-25, SHV-26, SHV-27, SHV-28, SHV-29, SHV-30, SHV-31, SHV-32, SHV-33, SHV-34, SHV-35, SHV-36, SHV-37, SHV-38, SHV-40, SHV-41, SHV-42, SHV-43, SHV-44, SHV-45, SHV-46, SHV-48, SHV-49, SHV-50, SHV-51, SHV-52, SHV-53, SHV-55, SHV-56, SHV-57, SHV-59, SHV-60, SHV-61, SHV-62, SHV-63, SHV-64, SHV-65, SHV-66, SHV-67, SHV-69, SHV-70, SHV-71, SHV-72, SHV-73, SHV-74, SHV-75, SHV-76, SHV-77, SHV-78, SHV-79, SHV-80, SHV-81, SHV-82, SHV-85, SHV-86, SHV-89, SHV-92, SHV-93, SHV-94, SHV-95, SHV-96, SHV-97, SHV-98, SHV-99, SHV-100, SHV-101, SHV-102, SHV-103, SHV-104, SHV-105, SHV-106, SHV-107, SHV-109, SHV-110, SHV-111, SHV-119, SHV-120, SHV-121, SHV-122, SHV-123, SHV-124, SHV-125, SHV-126, SHV-127, SHV-128, SHV-129, SHV-132, SHV-133, SHV-134, SHV-135, SHV-136, SHV-137, SHV-140, SHV-141, SHV-142, SHV-143, SHV-144, SHV-145, SHV-146, SHV-147, SHV-148, SHV-149, SHV-150, SHV-151, SHV-152, SHV-153, SHV-154, SHV-155, SHV-156, SHV-157, SHV-158, SHV-159, SHV-160, SHV-161, SHV-162, SHV-163, SHV-164, SHV-165, SHV-168, SHV-172, SHV-173, SHV-178, SHV-179, SHV-180, SHV-182, SHV-183, SHV-185, SHV-186, SHV-187, SHV-188, SHV-189, SHV-190, SHV-191, SHV-193, SHV-194, SHV-195, SHV-196, and SHV-197.

The present teachings may allow for the detection of the MCR gene family from a biological sample. The present teachings provide for a kit including one or more primers and/or probes for the identification by multiplex real-time polymerase chain reaction of MCR genes including the MCR-like family. The MCR-like genes detected may include MCR-1, MCR-1.2, MCR-1.3, MCR-1.4, MCR-1.5, MCR-1.6, MCR-1.7, MCR-1.8, MCR-1.9 and MCR-2.

The kit of the present teachings may include a mix of at least one primer and/or at least one probe. Primers and/or probes may be degenerate at any nucleotide position. Primers and/or probes may not be degenerate at any nucleotide position. A hydrolysis and/or hybridization probe may be designed for the detection of a specific nucleic acid sequence. Multiple probes may be labeled with a different colored fluorophore. The probe may be labeled with a fluorescent tag at one end and a fluorescent quencher at the other end. Two fluorescent quenchers may be included at one end or within the probe sequence. For example, the fluorophores may be selected from the group consisting of fluorescein, hexachlorofluorescein, TEX 615, and TYE™ 665. The fluorophores may excite between 450 nm and 763 nm and emit between 500 nm and 800 nm. For example, the quenchers may be selected from the group consisting of Iowa Black® quenchers and Black Hole Quenchers®. Peak absorbance of each quencher may be at 531 nm, 534 nm, 578 nm, or 656 nm.

Multiple hydrolysis and/or hybridization probes can be added to the same nucleic acid amplification reaction. The selection of the fluorescent labels may depend on the type of hydrolysis and/or hybridization probe used, the number of targets to be detected and the type of thermal cycler used. Preferable combinations of fluorophores and quenchers for multiplex reactions require appropriate excitation wavelengths and little to no overlap in their emission spectra as well as reduction of background fluorescence. It is contemplated that the probe sequences of the present teachings may be labeled with any suitable fluorophore and quencher combinations. For example, any fluorophore of the present teachings may be attached to any probe DNA sequence of the present teachings.

The one or more primers and/or probes maybe selected from the group consisting of: TGGCCAGAACTGACAGGCAAA, TTTCTCCTGAACGTGGCTGGC, 56-FAM/ACGCTAACT/ZEN/CCAGCATTGGTCTGT/3IABkFQ/, CCGTCACGCTGTTGTTAGG, GCTGTGTTAATCAATGCCACAC, 5HEX/AACTTGCCG/ZEN/AATTAGAGCRGCAGT/3IABkFQ, CGTTTCGTCTGGATCGCAC, GCTGGGTAAAATAGGTCACC, 5TEX615/TATCATTGGTGGTGCCGTAGTCGC/3IAbRQSp, GAGAGGATGAYCAGCCACAC, CGCCCATTGTSCAATATTCC, 5TYE665/TGAGACACGGTCCAGACTCCTACG/3IAbRQSp, AATCACAGGGCGTAGTTGTG, ACCCACCAGCCAATCTTAGG, 56-FAM/TAGCTTGAT/ZEN/CGCCCTCGATTTGGG/3IABkFQ/, GCGGAGTTAACTATTGGCTAG, GGCCAAGCTTCTATATTTGCG, 5HEX/TTRTTYGGT/ZEN/GGTTGYTTTRTTAA/3IABkFQ, GCGGAGTTARYTATTGGCTAG, GGCCAAGCYTCTAWATTTGCG, /5HEX/CCGGACGGT/ZEN/CTTGGTAATTTGGGT/3IABkFQ/, /5HEX/CCGTACGGT/ZEN/TTAGGCAATTTGGGT/3IABkFQ/, GGCGGCGTTGATGTCCTTCG, CCATTCAGCCAGATCGGCATC, 5TEX615/AGCTCTTCTATCCTGGTGCTGCG/3IAbRQSp, AACTTTCACAGGTGTGCTGGGT, CCGTACGCATACTGGCTTTGC, 56-FAM/AAACCGGGC/ZEN/GATATGCGTCTGTAT/3IABkFQ/, GTATCGCCGTCTAGTTCTGC, CCTTGAATGAGCTGCACAGTGG, 5HEX/TCGTCGCGG/ZEN/AACCATTCGCTAAA/3IABkFQ/, GTTTGATCGTCAGGGATGGC, GGCGAAAGTCAGGCTGTG, 5TEX615/CATCAGGACAAGATGGGCGGTATG/3IAbRQSp, GCTGCTCAAGGAGCACAGGAT, CACATTGACATAGGTGTGGTGC, 56-FAM/AGGATGGCA/ZEN/AGGCCCACTATTTCA/3IABkFQ, AACAGCCTCAGCAGCCGGTTA, TTCGCCGCAATCATCCCTAGC, 5HEX/AGCCATTAC/ZEN/GTTCCAGATTGCGT/3IABkFQ, GCCGAGGCTTACGGGATCAAG, CAAAGCGCGTAACCGGATTGG, 5TEX615/TCTGCTGAAGTTTRYCGAGGCMAA/3IAbRQSp, AACTTTCACAGGTGTGCTGGGT, CCGTACGCATACTGGCTTTGC, 56-FAM/AAACCGGGC/ZEN/GATATGCGTCTGTAT/3IABkFQ/, CTGGGTTCTATAAGTAAAACCTTCACCGG, CTTCCACTGCGGCTGCCAGTT, 5HEX/GATGCCATT/ZEN/GCYCGSGGTGAAAT/3IABkFQ, CCGAAGCCTATGGCGTGAAATCC, GCAATGCCCTGCTGGAGCG, 5TEX615/ATGTTGGCCTGAACCCAGCG/3IAbRQSp.

Primers and/or probes included in this group may or may not be degenerate at any nucleotide position. [SEQ. ID NOS 67-118]

The kit may include one or more primer-probe multiplex mixes. The primer-probe multiplex mix may include one or more internal controls. The primer-probe multiplex mix and one or more internal controls may be enclosed in one container, such as a vial. The primer-probe multiplex mix and one or more internal controls may be enclosed in more than one container, such as vials.

A primer-probe mix may include sequences for detecting any combination of the following genes: CMY-2-like, CTX-M-14-like, CTX-M-15-like, IMP-like, VIM-like, DHA-like, KPC-like, NDM-like, MOX-like, ACC-like, FOX-like, DHA-like, EBC-like, OXA-143-like, OXA-23-like, OXA-51-like, OXA-48-like, OXA-58-like and OXA-24/40-like.

For example, the kit may include a first primer-probe mix and one or more internal controls in a first vial and a second primer-probe mix and one or more internal controls in a second vial. For example, the kit may include a first primer-probe mix and one or more internal controls in a first vial, a second primer-probe mix and one or more internal controls in a second vial and a third primer-probe mix and one or more internal controls in a third vial. Each vial may contain different mixtures. Each vial may contain the same mixture.

The kit may include at least one control DNA mix. The kit may include one or more DNA control mixes. The kit may include exactly two control DNA mixes. The kit may include exactly three control DNA mixes. The DNA control mix may include at least one DNA sequence corresponding to at least one gene family and at least one internal control DNA sequence. The DNA control mix may be enclosed in one container, such as a vial. The DNA control mix may be enclosed in more than one container, such as vials.

For example, the kit may include a first DNA control mix in a first vial and a second DNA control mix in a second vial. For example, the kit may include a first DNA control mix in a first vial, a second DNA control mix in a second vial and a third DNA control mix in a third vial. Each vial may contain different mixtures. Each vial may contain the same mixture.

In one example, the kit includes three primer-probe multiplex mix vials including internal controls and three DNA control mix vials. The three primer-probe multiplex mixes may provide for identification of up to nine antibiotic resistance genes and internal controls. A first primer-probe mix may include sequences for detecting gene families which are CMY-2-like, CTX-M-14-like, CTX-M-15-like and internal controls. A second primer-probe mix may include sequences for detecting gene families which are OXA-48-like, IMP-like, VIM-like and internal controls. A third primer-probe mix may include sequences for detecting gene families which are DHA-like, KPC-like, NDM-like and internal controls. The one or more DNA control mixes may be plasmid or vector controls. A first DNA control mix may include DNA sequences for CMY-2, CTX-M-14, CTX-M-15 and an internal control DNA sequence. A second DNA control mix may include DNA sequences for OXA-48, IMP, VIM and an internal control DNA sequence. A third DNA control mix may include DNA sequences for DHA, KPC, NDM and an internal control DNA sequence.

It is contemplated that the combination of gene families may vary. For example, a primer-probe mix may include sequences for detecting any combination of the following genes: CMY-2-like, CTX-M-14-like, CTX-M-15-like, and OXA-48-like, IMP-like, VIM-like, DHA-like, KPC-like and NDM-like. It is further contemplated that additional β-lactamase gene targets may be included in the primer-probe mix or mixes.

The first primer-probe mix may include one or more primers and/or probes selected from the group consisting of: TGGCCAGAACTGACAGGCAAA, TTTCTCCTGAACGTGGCTGGC, 56FAM/ACGCTAACT/ZEN/CCAGCATTGGTCTGT/3IABkFQ/, CCGTCACGCTGTTGTTAGG, GCTGTGTTAATCAATGCCACAC, 5HEX/AACTTGCCG/ZEN/AATTAGAGCRGCAGT/3IABkFQ, CGTTTCGTCTGGATCGCAC, GCTGGGTAAAATAGGTCACC and 5TEX615/TATCATTGGTGGTGCCGTAGTCGC/3IAbRQSp. The first primer-probe mix may include one or more internal controls selected from the group consisting of: GAGAGGATGAYCAGCCACAC, CGCCCATTGTSCAATATTCC and 5TYE665/TGAGACACGGTCCAGACTCCTACG/3IAbRQSp. A primer-probe mix may include a combination of the one or more said group of primers and/or probes and the one or more said group of internal controls. The primer-probe mix including internal controls may be a multiplex mix. [SEQ. ID NOS 152-163]

The kit may include a first, second and third primer and/or probe mix, the first primer and/or probe mix including one or more primers and/or probes selected from the group consisting of: TGGCCAGAACTGACAGGCAAA, TTTCTCCTGAACGTGGCTGGC, 56-FAM/ACGCTAACT/ZEN/CCAGCATTGGTCTGT/3IABkFQ/, CCGTCACGCTGTTGTTAGG, GCTGTGTTAATCAATGCCACAC, 5HEX/AACTTGCCG/ZEN/AATTAGAGCRGCAGT/3IABkFQ, CGTTTCGTCTGGATCGCAC, GCTGGGTAAAATAGGTCACC, 5TEX615/TATCATTGGTGGTGCCGTAGTCGC/3IAbRQSp, GAGAGGATGAYCAGCCACAC, CGCCCATTGTSCAATATTCC, and 5TYE665/TGAGACACGGTCCAGACTCCTACG/3IAbRQSp. Primers and/or probes included in this group may or may not be degenerate at any nucleotide position. [SEQ. ID NOS 152-163]

The second primer-probe mix may include one or more primers and/or probes selected from the group consisting of: AATCACAGGGCGTAGTTGTG, ACCCACCAGCCAATCTTAGG, 56-FAM/TAGCTTGAT/ZEN/CGCCCTCGATTTGGG/3IABkFQ/, GCGGAGTTAACTATTGGCTAG, GGCCAAGCTTCTATATTTGCG, 5HEX/TTRTTYGGT/ZEN/GGTTGYTTTRTTAA/3IABkFQ, GCGGAGTTARYTATTGGCTAG, GGCCAAGCYTCTAWATTTGCG, /5HEX/CCGGACGGT/ZEN/CTTGGTAATTTGGGT/3IABkFQ/, /5HEX/CCGTACGGT/ZEN/TTAGGCAATTTGGGT/3IABkFQ, GGCGGCGTTGATGTCCTTCG, CCATTCAGCCAGATCGGCATC and 5TEX615/AGCTCTTCTATCCTGGTGCTGCG/3IAbRQSp. The second primer-probe mix may include one or more internal controls selected from the group consisting of: GAGAGGATGAYCAGCCACAC, CGCCCATTGTSCAATATTCC, and 5TYE665/TGAGACACGGTCCAGACTCCTACG/3IAbRQSp. A primer-probe mix may include a combination of the one or more said group of primers and/or probes and the one or more said group of internal controls. The primer-probe mix including internal controls may be a multiplex mix. [SEQ. ID NOS 164-179]

The kit may include a first, second, and third primer and/or probe mix, the second primer and/or probe mix including one or more primers and/or probes selected from the group consisting of: AATCACAGGGCGTAGTTGTG, ACCCACCAGCCAATCTTAGG, 56-FAM/TAGCTTGAT/ZEN/CGCCCTCGATTTGGG/13IABkFQ/, GCGGAGTTAACTATTGGCTAG, GGCCAAGCTTCTATATTTGCG, 5HEX/TTRTTYGGT/ZEN/GGTTGYTTTRTTAA/3IABkFQ, GCGGAGTTARYTATTGGCTAG, GGCCAAGCYTCTAWATTTGCG, /5HEX/CCGGACGGT/ZEN/CTTGGTAATTTGGGT/3IABkFQ/, /5HEX/CCGTACGGT/ZEN/TTAGGCAATTTGGGT/3IABkFQ, GGCGGCGTTGATGTCCTTCG, CCATTCAGCCAGATCGGCATC, 5TEX615/AGCTCTTCTATCCTGGTGCTGCG/3IAbRQSp, GAGAGGATGAYCAGCCACAC, CGCCCATTGTSCAATATTCC, and 5TYE665/TGAGACACGGTCCAGACTCCTACG/

3IAbRQSp. Primers and/or probes included in this group may or may not be degenerate at any nucleotide position. [SEQ. ID NOS 164-179]

The third primer-probe mix may include one or more primers and/or probes selected from the group consisting of: AACTTTCACAGGTGTGCTGGGT, CCGTACGCATACTGGCTTTGC, 56-FAM/AAACCGGGC/ZEN/GATATGCGTCTGTAT/3IABkFQ/, GTATCGCCGTCTAGTTCTGC, CCTTGAATGAGCTGCACAGTGG, 5HEX/TCGTCGCGG/ZEN/AACCATTCGCTAAA/3IABkFQ/, GTTTGATCGTCAGGGATGGC, GGCGAAAGTCAGGCTGTG and 5TEX615/CATCAGGACAAGATGGGCGGTATG/3IAbRQSp. The third primer-probe mix may include one or more internal controls selected from the group consisting of: GAGAGGATGAYCAGCCACAC, CGCCCATTGTSCAATATTCC and 5TYE665/TGAGACACGGTCCAGACTCCTACG/3IAbRQSp. A primer-probe mix may include a combination of the one or more said group of primers and/or probes and the one or more said group of internal controls. The primer-probe mix including internal controls may be a multiplex mix. [SEQ. ID NOS 180-191]

The kit may include a first, second and third primer and/or probe mix, the third primer and/or probe mix including one or more primers and/or probes selected from the group consisting of: AACTTTCACAGGTGTGCTGGGT, CCGTACGCATACTGGCTTTGC, 56-FAM/AAACCGGGC/ZEN/GATATGCGTCTGTAT/3IABkFQ/, GTATCGCCGTCTAGTTCTGC, CCTTGAATGAGCTGCACAGTGG, 5HEX/TCGTCGCGG/ZEN/AACCATTCGCTAAA/3IABkFQ/, GTTTGATCGTCAGGGATGGC, GGCGAAAGTCAGGCTGTG, 5TEX615/CATCAGGACAAGATGGGCGGTATG/3IAbRQSp, GAGAGGATGAYCAGCCACAC, CGCCCATTGTSCAATATTCC, and 5TYE665/TGAGACACGGTCCAGACTCCTACG/3IAbRQSp. Primers and/or probes included in this group may or may not be degenerate at any nucleotide position. [SEQ. ID NOS 180-191]

A first DNA control mix may include one or more sequences selected from the group consisting of: TGGCCAGAACTGACAGGCAAACAGTGGCAGGGTATCCGCCTGCTGCACTTAGCCA CCTATACGGCAGGCGGCCTACCGCTGCAGATCCCCGATGACGTTAGGGATAAAGC CGCATTACTGCATTTTAT- CAAAACTGGCAGCCGCAATGGACTCCGGGCGCTA AGC GACTTTACGCTAACTCCAGCATTGGTCTGTTTGGCGCGCTGGCGGTGAAACCCTC AGGAATGAGTTACGAAGAGGCAATGACCAGACGCGTCCTGCAACCATTAAAACTG GCGCATACCTGGATTACGGTTCCGCAGAACGAACAAAAAGATTATGCCTGGGGCT ATCGCGAAGGGAAGCCCGTACACGTTTCTCCGGGACAACTTGACGCCGAAGCCTA TGGCGTGAAATCCAGCGTTATTGATATGGCCCGCTGGGTTCAGGCCAACATGGAT GCCAGCCACGTTCAGGAGAAA, CCGTCACGCTGTTGTTAGGAAGTGTGCCGCTGTATGCGCAAACGGCGGACGTACA GCAAAAACTTGCCGAATTAGAGCGGCAGTCGGGAGGCAGACTGGGTGTGGCATT GATTAACACAGC, and CGTTTCGTCTGGATCGCACTGAACCTACGCTGAATACCGCCATTCCCGGCGACCC GAGAGACACCACCACGCCGCGGGCGATGGCGCAGACGTTGCGTCAGCTTACGCT GGGTCATGCGCTGGGCGAAACCCAGCGGGCGCAGTTGGTGACGTGGCTCAAAGG CAATACGACCGGCGCAGCCAGCATTCGGGCCGGCTTACCGACGTCGTGGACTGT GGGTGATAAGACCGGCAGCGGCGACTACGGCACCACCAATGATATTGCGGTGATC TGGCCGCAGGGTCGTGCGCCGCTGGTTCTGGTGACCTATTTTACCCAGC. The first DNA control mix may include the following internal control sequence: GAGAGGATGACCAGCCACACTGGAACTGAGACACGGTCCAGACTCCTACGGGAG GCAGCAGTGGGGAATATTGCACAATGGGCG. A DNA control mix may include a combination of the one or more said group of sequences and the said internal control sequence. A DNA control mix may include any combination of sequences from the first control mix, the second control mix, the third control mix and the internal control sequence. [SEQ. ID NOS 261-264]

A second DNA control mix may include one or more sequences selected from the group consisting of: AATCACAGGGCGTAGTTGTGCTCTGGAATGAGAATAAGCAGCAAGGATTTACCAAT AATCTTAAACGGGCGAACCAAGCATTTTTACCCGCATCTA CCTTTAAAATTCCCAAT AGCTTGATCGCCCTCGATTTGGGCGTGGTTAAGGATGAACACCAAGTCTTTAAGTG GGATGGACAGACGCGCGATATCGCCACTTGGAATCGCGATCATAATCTAATCACC GCGATGAAATATTCAGTTGTGCCTGTTTATCAAGAATTTGCCCGCCAAATTGGCGA GGCACGTATGAGCAAGATGCTACATGCTTTCGATTATGGTAATGAGGACATTTCGG GCAATGTAGACAGTTTCTGGCTCGACGGTGGTATTCGAATTTCGGCCACGGAGCA AATCAGCTTTTTAAGAAAGCTGTATCACAATAAGTTACACGTATCGGAGCGCAGCC AGCGTATTGTCAAACAAGCCATGCTGACCGAAGCCAATGGTGACTATATTATTCGG GCTAAAACTGGATACTCGACTAGAATCGAACCTAAGATTGGCTGGTGGGT, GCGGAGTTAGTTATTGGCTAGTTAAAAATAAAATTGAAGTTTTTTATCCCGGCCCGG GGCACACTCAAGATAACGTAGTGGTTTGGTTACCTGAAAAGAAAATTTTATTCGGT GGTTGTTTTGTTAAACCGGACGGTCTTGGTAATTTGGGTGACGCAAATTTAGAAGC TTGGCC and GGCGGCGTTGATGTCCTTCGGGCGGCTGGGGTGGCAACGTACGCATCACCGTCG ACACGCCGGCTAGCCGAGGTAGAGGGGAACGAGATTCCCACGCACTCTCTAGAA GGACTCTCATCGAGCGGGGACGCAGTGCGCTTCGGTCCAGTA GAACTCTTCTATC CTGGTGCTGCGCATTCGACCGACAACTTAGTTGTGTACGTCCCGTCTGCGAGTGT GCTCTATGGTGGTTGTGCGATTCATGAGTTGTCACGCAC GTCTGCGGGGAACGTG GCCGATGCCGATCTGGCTGAATGG. The second DNA control mix may include the following internal control sequence: GAGAGGATGACCAGCCACACTGGAACTGAGACACGGTCCAGACTCCTACGGGAG GCAGCAGTGGGGAATATTGCACAATGGGCG. A DNA control mix may include a combination of the one or more said group of sequences and the said internal control sequence. A DNA control mix may include any combination of sequences from the first control mix, the second control mix, the third control mix and the internal control sequence. [SEQ. ID NOS 265-268]

A third DNA control mix may include one or more sequences selected from the group consisting of: AACTTTCACAGGTGTGCTGGGTGCGGTTTCTGTGGCGAAAA AAGAGATGGCGCTG AATGATCCGGCGGCAAAATACCAGCCGGAGCTGGCTCTGCCGCAGTGGAAGGGG ATCACATTGCTGGATCTGGCTACCTATACCGCAGGCGGACTG CCGTTACAGGTGC CGGATGCGGTAAAAAGCCGTGCGGATCTGCTGAATTTCTATCAGCAGTGGCAGCC GTCCCGGAAACCGGGCGATATGCGTCTGTATGCAAACAGCAGTATCGGCCTGTTT GGTGCTCTGACCGCAAACGCGGCGGGGATGCCGTATGAGCAGTTGCTGACTGCA CGGATCCTGGCACCGCTGGGGTTATCTCACACCTTTATTACTGTGCCGGAAAGTG CGCAAAGCCAGTATGCGTACGG, GTATCGCCGTCTAGTTCTGCTGTCTTGTCTCTCATGGCCGCTGGCTGGCTTTTCTG CCACCGCGCTGACCAACCTCGTCGCGGAACCATTCGCTAAACTCGAACAGGACTT TGGCGGCTCCATCGGTGTGTACGCGATGGATACCGGCTCAGGCGCAACTGTAAGT TACCGCGCTGAGGAGCGCTTCCCACTGTGCAGCTCATTCAAGG and GTTTGATCGTCAGGGATGGCGGCCGCGTGCTGGTGGTCGATACCGCCTGGACCG ATGACCAGACCGCCCAGATCCTCAACTGGATCAAGCAGGAGATCAACCTGCCGGT CGCGCTGGCGGTGGTGACTCACGCGCATCAGGACAAGATGGGCGGTATGGACGC GCTGCATGCGGCGGGGATTGCGACTTATGCCAATGCGTTGTCGAACCAGCTTGCC CCGCAAGAGGGGATGGTTGCGGCGCAACACAGCCTGACTTTCGCC. The third DNA control mix may include the following internal control sequence: GAGAGGATGACCAGCCACACTGGAACTGAGACACGGTCCAGACTCCTACGGGAG GCAGCAGTGGGGAATATTGCACAATGGGCG. A DNA control mix may include a combination of the one or more said group of sequences and the said internal control sequence. A DNA control mix may include any combination of sequences from the first control mix, the second control mix, the third control mix and the internal control sequence. [SEQ. ID NOS 269-272]

In one example, the kit includes two primer-probe multiplex mix vials including internal controls and two DNA control mix vials. The two primer-probe multiplex mixes may provide for identification of up to six antibiotic resistance genes and internal controls. A first primer-probe mix may include sequences for detecting gene families which are MOX-like, ACC-like, FOX-like and internal controls. A second primer-probe mix may include sequences for detecting gene families which are DHA-like, ACT/MIR-like, CMY-2-like and internal controls. A first DNA control mix may include DNA sequences for MOX, ACC, FOX and an internal control DNA sequence. A second DNA control mix may include DNA sequences for DHA, ACT/MIR, CMY-2 and an internal control DNA sequence.

It is contemplated that the combination of gene families may vary. For example, a primer-probe mix may include sequences for detecting any combination of the following genes: MOX-like, ACC-like, FOX-like, DHA-like, ACT/MIR-like and CMY-2-like. It is further contemplated that additional β-lactamase gene targets may be included in the primer-probe mix or mixes.

The first primer-probe mix may include one or more primers and/or probes selected from the group consisting of: GCTGCTCAAGGAGCACAGGAT, CACATTGACATAGGTGTGGTGC, 56-FAM/AGGATGGCA/ZEN/AGGCCCACTATTTCA/3IABkFQ, AACAGCCTCAGCAGCCGGTTA, TTCGCCGCAATCATCCCTAGC, 5HEX/AGCCATTAC/ZEN/GTTCCAGAGTTGCGT/3IABkFQ, GCCGAGGCTTACGGGATCAAG, CAAAGCGCGTAACCGGATTGG and 5TEX615/TCTGCTGAAGTTTRYCGAGGCMAA/3IAbRQSp. The first primer-probe mix may include one or more internal controls selected from the group consisting of: GAGAGGATGAYCAGCCACAC, CGCCCATTGTSCAATATTCC and 5TYE665/TGAGACACGGTCCAGACTCCTACG/3IAbRQSp. A primer-probe mix may include a combination of the one or more said group of primers and/or probes and the one or more said group of internal controls. The primer-probe mix including internal controls may be a multiplex mix. [SEQ. ID NOS 192-203]

The second primer-probe mix may include one or more primers and/or probes selected from the group consisting of: AACTTTCACAGGTGTGCTGGGT, CCGTACGCATACTGGCTTTGC, 56-FAM/AAACCGGGC/ZEN/GATATGCGTCTGTAT/3IABkFQ, CTGGGTTCTATAAGTAAAACCTTCACCGG, CTTCCACTGCGGCTGCCAGTT, 5HEX/GATGCCATT/ZEN/GCYCGSGGTGAAAT/3IABkFQ, CCGAAGCCTATGGCGTGAAATCC, GCAATGCCCTGCTGGAGCG, and 5TEX615/ATGTTGGCCTGAACCCAGCG/3IAbRQSp. The second primer-probe mix may include one or more internal controls selected from the group consisting of: GAGAGGATGAYCAGCCACAC, CGCCCATTGTSCAATATTCC and 5TYE665/TGAGACACGGTCCAGACTCCTACG/3IAbRQSp. A primer-probe mix may include a combination of the one or more said group of primers and/or probes and the one or more said group of internal controls. The primer-probe mix including internal controls may be a multiplex mix. [SEQ. ID NOS 204-215]

The kit may include exactly two primer and/or probe mixes, a first primer and/or probe mix including one or more primers and/or probes selected from the group consisting of: GCTGCTCAAGGAGCACAGGAT, CACATTGACATAGGTGTGGTGC, 56-FAM/AGGATGGCA/ZEN/AGGCCCACTATTTCA/3IABkFQ, AACAGCCTCAGCAGCCGGTTA, TTCGCCGCAATCATCCCTAGC, 5HEX/AGCCATTAC/ZEN/GTTCCAGAGTTGCGT/3IABkFQ, GCCGAGGCTTACGGGATCAAG, CAAAGCGCGTAACCGGATTGG, 5TEX615/TCTGCTGAAGTTTRYCGAGGCMAA/3IAbRQSp, GAGAGGATGAYCAGCCACAC, CGCCATTGTSCAATATTCC, and 5TYE665/TGAGACACGGTCCAGACTCCTACG/3IAbRQSp; and a second primer and/or probe mix including one or more primers and/or probes selected from the group consisting of: AACTTTCACAGGTGTGCTGGGT, CCGTACGCATACTGGCTTTGC, 56-FAM/AAACCGGGC/ZEN/GATATGCGTCTGTAT/3IABkFQ, CTGGGTTCTATAAGTAAAACCTTCACCGG, CTTCCACTGCGGCTGCCAGTT, 5HEX/GATGCCATT/ZEN/GCYCGSGGTGAAAT/3IABkFQ, CCGAAGCCTATGGCGTGAAATCC, GCAATGCCCTGCTGGAGCG, 5TEX615/ATGTTGGCCTGAACCCAGCG/3IAbRQSp, GAGAGGATGAYCAGCCACAC, CGCCCATTGTSCAATATTCC, and 5TYE665/TGAGACACGGTCCAGACTCCTACG/3IAbRQSp. Primers and/or probes included in this group may or may not be degenerate at any nucleotide position. [SEQ. ID NOS 192-215]

A first DNA control mix may include one or more sequences selected from the group consisting of: GCTGCT- CAAGGAGCACAGGATCCGGG-CATGGCGGTGGCCGTGCTCAAGGATGG CAAGGCC-CACTATTTCAATTACGGGGTGGCCAACCGGGAGAG CGGGGCCAGCGT CAGCGAGCA-GACCCTGTTCGAGATAGGATCCGTGAGCAA-GACCCTGACTGCGACC CTGGGGGCC-TATGCGGTGGTCAAGGGAGCGATGCAGCTGGATG ACAAGGCGAGC CGGCACGCGCCCTGGCTCAAGG-GATCCGTCTTTGACAGCATCACCATGGGGGAG CTTGCCACCTACAGCGCCGGAGGCCTGC-CACTGCAATTCCCCGAGGAGGTGGATT CATCCGAGAAGATGCGCGCCTAC-TACCGCCAGTGGGCCCCTGTCTATTCGCCGGG CTCCCATCGCCAGTACTCCAACCCCAGCAT-AGGGCTGTTCGGCCACCTGGCGGCG AGCAGCCT-GAAGCAGCCATTTGCCCAGTTGATGGAGCA-GACCCTGCTGCCCGGG CTCGGCATGCACCACACCTATGTCAATGTG, AACAGCCTCAGCAGCCGGTTACGGAAAATACGTT-ATTTGAAGTGGGTTCGCTGAGT AAAACGTTTGCTGCCACCTTGGCGTCC-TATGCGCAGGTGAGCGGTAAGCTGTCTTT GGAT-CAAAGCGTTAGCCAT-TACGTTCCAGAGTTGCGTGGCAGCAGCTTTGACCA C GTTAGCGTACTCAATGTGGGCACGCAT-ACCTCAGGCCTACAGCTATTTATGCCGGA AGATAT-TAAAAATACCACACAGCTGATGGCT-TATCTAAAAGCATGGAAACCTGCCG ATGCGGCTGGAACCCATCGCGTTTATTC-CAATATCGGTACTGGTTTGCTAGGGATG ATTGCGGCGAA and GCCGAGGCTTACGGGATCAA-GACCGGCTCGGCGGATCTGCTGAAGTTTACCGAG GCCAACATGGGGTATCAGG-GAGATGCCGCGCTAAAAACGCGGATCGCGCTGACC CATACCGGTTTCTACTCGGTGGGAGA-CATGACTCAGGGGCTGGGTTGGGAGAGCT ACGCC-TATCCGTTGACCGAGCAGGCGCTGCTGGCGGGCAA CTCCCCGGCGGTGA GCTTCCAGGCCAATCCGGT-TACGCGCTTTG. The first DNA control mix may include the following internal control sequence: GAGAG-GATGACCAGCCACACTGGAACTGA-GACACGGTCCAGACTCCTACGGGAG GCAGCAGTGGGGAATATTGCACAATGGGCG. A DNA control mix may include a combination of the one or more said group of sequences and the said internal control sequence. A DNA control mix may include any combination of sequences from the first control mix, the second control mix and the internal control sequence. [SEQ. ID NOS 273-276]

A second DNA control mix may include one or more sequences selected from the group consisting of: AACTTT-CACAGGTGTGCTGGGTGCGGTTTCTGTGGCGAAA AAAGAGATGGCGCTG AAT-GATCCGGCGGCAAAATACCAGCCG-GAGCTGGCTCTGCCGCAGTGGAAGGGG ATCACAT-TGCTGGATCTGGCTACCTATACCGCAGGCGGACTG CCGTTACAGGTGC CGGATGCGGTAAAAAGCCGTGCGGATCTGCTGAAT-TTCTATCAGCAGTGGCAGCC GTCCCG-GAAACCGGGCGA-TATGCGTCTGTATGCAAACAGCAGTATCGGCCTGTT T GGTGCTCTGACCGCAAACGCGGCGGG-GATGCCGTATGAGCAGTTGCTGACTGCA CGGATCCTGGCACCGCTGGGGTTATCTCACACCTT-TATTACTGTGCCGGAAAGTG CGCAAAGCCAGTATGCGTACGG, TCGGTAAAGCC-GATGTTGCGGCGAACAAACCCGT-CACCCCGCAAACCCTGTTTGA GCTGGGCTC-TATAAGTAAAACCTTCACCGGCGTACTGGGCGGCG ATGCCATTGCC CGGGGTGAAATAGCGCTGGGC-GATCCGGTAGCAAAATACTGGCCTGAGCTCACG GGCAAGCAGTGGCAGGGCATTCGCATGCTG-GATCTGGCAACCTATACCGCAGGC GGTCTGCCGT-TACAGGTGCCGGATGAGGTCACGGA-TACCGCCTCTCTGCTGCGCT TTTATCAAAACTGGCAGCCGCAGTGGAAG and CCGAAGCCTATGGCGTGAAATCCAGCGTTATTGA-TATGGCCCGCTGGGTTCAGGC CAACATG-GATGCCAGCCACGTTCAG-GAGAAAACGCTCCAGCAGGGCATTGC. The second DNA control mix may include the following internal control sequence: GAGAGGATGACCAGCCACACTGGAACT-GAGACACGGTCCAGACTCCTACGGGAG GCAGCAGTGGGGAATATTGCACAATGGGCG. A DNA control mix may include a combination of the one or more said group of sequences and the said internal control sequence. A DNA control mix may include any combination of sequences from the first control mix, the second control mix and the internal control sequence. [SEQ. ID NOS 277-280]

In one example, the kit includes two primer-probe multiplex mix vials including internal controls and two DNA control mix vials. The two primer-probe multiplex mixes may provide for identification of up to six antibiotic resistance genes and internal controls. A first primer-probe mix may include sequences for detecting gene families which are OXA-143-like, OXA-23-like, OXA-51-like and internal controls. A second primer-probe mix may include sequences for detecting gene families which are OXA-48-like, OXA-58-like, OXA-24/40-like and internal controls. A first DNA control mix may include DNA sequences for OXA-143, OXA-23, OXA-51 and an internal control DNA sequence. A second DNA control mix may include DNA sequences for OXA-48, OXA-58 and OXA 24/40 and an internal control DNA sequence.

It is contemplated that the combination of gene families may vary. For example, a primer-probe mix may include sequences for detecting any combination of the following genes: OXA-143-like, OXA-23-like, OXA-51-like, OXA-48-like, OXA-58-like and OXA-24/40-like. It is further contemplated that additional β-lactamase gene targets may be included in the primer-probe mix or mixes.

The first primer-probe mix may include one or more primers and/or probes selected from the group consisting of: AGCACATACAGAATATGTCCCTGC, ACCTGTTAAC-CAACCTACTTGAGGG, /56-FAM/TTGCAA-GACGGACTGGCTTAGACC/3BHQ_1/, CCTGATCG-GATTGGAGAACC, CTACCTCTTGAATAGGCGTAACC, /5TEX615/ ACGTCGCGCAAGTTCCTGATAGAC/3IAbRQSp/, TAGTGACTGCTAATCCAAATCACAG, GCACGAGCAAGATCATTACCATAGC, /5HEX/AGT-TATCCAACAAGGCCAAACTCAACA/3BHQ_1/. [SEQ. ID NOS 119-127] The first primer-probe mix may include one or more internal controls selected from the group consisting of: GAGAGGATGAYCAGCCACAC (SEQ ID NO: 201), CGCCCATTGTSCAATATTCC (SEQ ID NO: 202) and 5TYE665/TGAGACACGGTCCAGACTCC-TACG/3IAbRQSp (SEQ ID NO: 203). A primer-probe mix may include a combination of the one or more said group of primers and/or probes and the one or more said group of internal controls. The primer-probe mix including internal controls may be a multiplex mix.

The second primer-probe mix may include one or more primers and/or probes selected from the group consisting of:

AATCACAGGGCGTAGTTGTG, ACCCACCAGCCAATCTTAGG, /5HEX/TAGCTTGATCGCCCTCGATTTGGG/3BHQ_1/, GTGGGATGGAAAGCCACG, CACTTGCGGGTCTACAGC, /56-FAM/TTACTTTGGGCGAAGCCATGCAAG/3BHQ_1/, CACCTATGGTAATGCTCTTGC, CTGGAACTGCTGACAATGCC, /5TEX615/TGGGAGAAAGATATGACTTTAGGTGAGGCA/3IAbRQSp/. [SEQ. ID NOS 128-136] The second primer-probe mix may include one or more internal controls selected from the group consisting of: GAGAGGATGAYCAGCCACAC (SEQ ID NO: 201), CGCCCATTGTSCAATATTCC (SEQ ID NO: 202) and 5TYE665/TGAGACACGGTCCAGACTCCTACG/3IAbRQSp (SEQ ID NO: 203). A primer-probe mix may include a combination of the one or more said group of primers and/or probes and the one or more said group of internal controls. The primer-probe mix including internal controls may be a multiplex mix.

The kit may include exactly two primer and/or probe mixes, a first primer and/or probe mix including one or more primers and/or probes selected from the group consisting of: AGCACATACAGAATATGTCCCTGC, ACCTGTTAACCAACCTACTTGAGGG, /56-FAM/TTGCAAGACGGACTGGCTTAGACC/3BHQ_1/, CCTGATCGGATTGGAGAACC, CTACCTCTTGAATAGGCGTAACC, /5TEX615/ACGTCGCGCAAGTTCCTGATAGAC/3IAbRQSp/, TAGTGACTGCTAATCCAAATCACAG, GCACGAGCAAGATCATTACCATAGC, /5HEX/AGTTATCCAACAAGGCCAAACTCAACA/3BHQ_1/, GAGAGGATGAYCAGCCACAC, CGCCCATTGTSCAATATTCC and 5TYE665/TGAGACACGGTCCAGACTCCTACG/3IAbRQSp; and a second primer and/or probe mix including one or more primers and/or probes selected from the group consisting of: AATCACAGGGCGTAGTTGTG, ACCCACCAGCCAATCTTAGG, /5HEX/TAGCTTGATCGCCCTCGATTTGGG/3BHQ_1/, GTGGGATGGAAAGCCACG, CACTTGCGGGTCTACAGC, /56-FAM/TTACTTTGGGCGAAGCCATGCAAG/3BHQ_1/, CACCTATGGTAATGCTCTTGC, CTGGAACTGCTGACAATGCC, /5TEX615/TGGGAGAAAGATATGACTTTAGGTGAGGCA/3IAbRQSp/, GAGAGGATGAYCAGCCACAC, CGCCCATTGTSCAATATTCC and 5TYE665/TGAGACACGGTCCAGACTCCTACG/3IAbRQSp. Primers and/or probes included in this group may or may not be degenerate at any nucleotide position. [SEQ. ID NOS 216-239]

A first DNA control mix may include one or more sequences selected from the group consisting of: AGCACATACAGAATATGTCCCTGCATCAACATTTAAGATGCTAAATGCCTTAATTGG ACTAGAAAATCATAAAGCTACAACAACTGAGATTTTCAAATGGGACGG TAAAAAGA GATCTTATCCATGTGGGAAAAAGATATGACTTTAGGTGATGCCATGGCACTTTCA GCAGTTCCTGTATATCAAGAACTTGCAAGACGGACTGGCTTAGACCTAATGCAAAA AGAAGTTAAACGGGTTGGTTTTGGTAATATGAACATTGGAACACAAGTTGATAACTT CTGGTTGGTTGGCCCCCTCAAGATTACACCAATACAAGAGGTTAATTTTGCCGATG ATTTTGCAAATAATCGATTACCCTTTAAATTAGAGACTCAAGAAGAAGTTAAAAAAAT GCTTCTGATTAAAGAATTCAATGGTAGTAAAATTTATGCAAAAAGCGGCTGGGGAA TGGATGTAACCCCTCAAGTAGGTTGGTTAACAGGT, CCTGATCGGATTGGAGAACCAGAAAACGGATATTAATGAAATATTTAAATGGAAGG GCGAGAAAAGGTCATTTACCGCTTGGGAAAAAGACATGACACTAGGAGAAGCCAT GAAGCTTTCTGCAGTCCCAGTCTATCAGGAACTTGCGCGACGTATCGGTCTTGATC TCATGCAAAAAGAAGTAAAACGTATTGGTTTCGGTAATGCTGAAATTGGACAGCAG GTTGATAATTTCTGGTTGGTAGGACCATTAAAGGTTACGCCTATTCAAGAGGTAG and TAGTGACTGCTAATCCAAATCACAGCGCTTCAAAATCTGATGAAAAAGCAGAGAAA ATTAAAAATTTATTTAACGAAGTACACACTACGGGTGTTTTAGTTATCCAACAAGGC CAAACTCAACAAAGCTATGGTAATGATCTTGCTCGTGC. The first DNA control mix may include the following internal control sequence: GAGAGGATGACCAGCCACACTGGAACTGAGACACGGTCCAGACTCCTACGGGAG GCAGCAGTGGGGAATATTGCACAATGGGCG. A DNA control mix may include a combination of the one or more said group of sequences and the said internal control sequence. A DNA control mix may include any combination of sequences from the first control mix, the second control mix and the internal control sequence. [SEQ. ID NOS 281-284]

A second DNA control mix may include one or more sequences selected from the group consisting of: AATCACAGGGCGTAGTTGTGCTCTGGAATGAGAATAAGCAGCAAGGATTTACCAAT AATCTTAAACGGGCGAACCAAGCATTTTTACCCGCATCTACCTTTAAAAATTCCCAAT AGCTTGATCGCCCTCGATTTGGGCGTGGTTAAGGATGAACACCAAGTCTTTAAGTG GGATGGACAGACGCGCGATATCGCCACTTGGAATCGCGATCATAATCTAATCACC GCGATGAAATATTCAGTTGTGCCTGTTTATCAAGAATTTGCCCGCCAAATTGGCGA GGCACGTATGAGCAAGATGCTACATGCTTTCGATTATGGTAATGAGGACATTTCGG GCAATGTAGACAGTTTCTGGCTCGACGGTGGTATTCGAATTTCGGCCACGGAGCA AATCAGCTTTTAAGAAAGCTGTATCACAATAAGTTACACGTATCGGAGCGCAGCC AGCGTATTGTCAAACAAGCCATGCTGACCGAAGCCAATGGTGACTATATTATTCGG GCTAAAACTGGATACTCGACTAGAATCGAACCTAAGATTGGCTGGTGGGT, GTGGGATGGAAAGCCACGTTTTTTTAAAGCATGGGACAAAGATTTTACTTTGGGCG AAGCCATGCAAGCATCTACAGTGCCTGTATATCAAGAATTGGCACGTCGTATTGGT CCAAGCTTAATGCAAAGTGAATTGCAACGTATTGGTTATGGCAATATGCAAATAGG CACGGAAGTTGATCAATTTTGGTTGAAAGGGCCTTTGACAATTACACCTATACAAG AAGTAAAGTTTGTGTATGATTTAGCCCAAGGGCAATTGCCTTTTAAACCTGAAGTTC AGCAACAAGTGAAAGAGATGTTGTATGTAGAGCGCAGAGGGGAGAATCGTCTATA TGCTAAAAGTGGCTGGGGAATGGCTGTAGACCCGCAAGTG, CACTTGCGGGTCTACAGCCATTCCCCAGCCACTTTTAGCATATAGACGATTCTCCC CTCTGCGCTCTACATACAACATCTCTTTCACTTGTTGCTGAACTTCAGGTTTAAAAG GCAATTGCCCTTGGGCTAAATCATACACAAACTT-
TACTTCTTGTATAGGTGTAATTG TCAAAGGCCCTTT-
CAACCAAAATTGATCAACTTCCGTGCCTATTTGCAT-
ATTGCCAT
AACCAATACGTTGCAATTCACTTTGCAT-
TAAGCTTGGACCAATACGACGTGCCAATT CTTGA-
TATACAGGCACTGTAGATGCTTGCATGGCTTCGCC-
CAAAGTAAAATCTTTGT
CCCATGCTTTAAAAAAACGTGGCTTTCCATCCCAC,
and CACC-
TATGGTAATGCTCTTGCACGAGCAAATAAAGAATAT
GTCCCTGCATCAACATT TAAGATGCTAAATGCTT-
TAATCGGGCTAGAAAATCATAAAGCAACAACAAAT-
GAGAT TTTCAAATGGGATGGTAAAAAAAGAACT-
TATCCTATGTGGGAGAAAGATATGACTTT
AGGTGAGGCAATGGCATTGTCAGCAGTTCCAG. The second DNA control mix may include the following internal control sequence: GAGAGGATGACCAGCCACACTG-GAACTGAGACACGGTCCAGACTCCTACGGGAG GCAGCAGTGGGGAATATTGCACAATGGGCG. A DNA control mix may include a combination of the one or more said group of sequences and the said internal control sequence additional β-lactamase. A DNA control mix may include any combination of sequences from the first control mix, the second control mix and the internal control sequence. [SEQ. ID NOS 285-289]

In one example, the kit includes one primer-probe multiplex mix vials including internal control and one DNA control mix vial. A primer-probe mix may include sequences for detecting MCR gene families and internal control.

The primer-probe mix may include primers and/or probes selected from the group consisting of: CCGTGTATGTTCAGCTAT, CTTATCCATCACGCCTTT, /5TEX615/TATGATGTCGATACCGCCAAATACCA/3IAbRQSp/, CTGTATGTCAGCGATCAT, GATGCCAGTTTGCTTATCC, /56-FAM/AAGTCTGGG/ZEN/TGAGAACGGTGTCTAT/3IABkFQ/, CAGTCAGTATGCGAGTTTC, AAAATTCGCCAAGC-CATC, and /5HEX/TGCATAAGC/ZEN/CAGTGCGTTTT-TATAT/3IABkFQ/. The primer-probe mix may include one or more internal controls selected from the group consisting of: GAGAGGATGAYCAGCCACAC, CGCCCATTGTS-CAATATTCC and 5TYE665/TGAGACACGGTCCA-GACTCCTACG/3IAbRQSp. The primer-probe mix may include a combination of the one or more said group of primers and/or probes and the one or more said group of internal controls. The primer-probe mix including internal controls may be a multiplex mix. [SEQ. ID NOS 137-145]

A DNA control mix may include one or more sequences selected from the group consisting of

ATGATGCAGCATACTTCTGTGTGGTACCGACGCTCGGTCAGTCCGTTTGT

TCTTGTGGGAGTGTTGCCGTTTTCTTGACCGCGACCGCCAATCTTACCTT

TTTTGATAAAATCAGCCAAACCTATCCCATCGCGGACAATCTCGGCTTTG

TGCTGACGATCGCTGTCGTGCTCTTTGGCGCGATGCTACTGATCACCACG

CTGTTATCATCGTATCGCTATGTGCTAAAGCCTGTGTTGATTTTGCTATT

AATCATGGGCGCGGTGACCAGTTATTTTACTGACACTTATGGCACGGTCT

ATGATACGACCATGCTCCAAAATGCCCTACAGACCGACCAAGCCGAGACC

AAGGATCTATTAAACGCAGCGTTTATCATGCGTATCATTGGTTTGGGTGT

GCTACCAAGTTTGCTTGTGGCTTTTGTTAAGGTGGATTATCCGACTTGGG

GCAAGGGTTTGATGCGCCGATTGGGCTTGATCGTGGCAAGTCTTGCGCTG

ATTTTACTGCCTGTGGTGGCGTTCAGCAGTCATTATGCCAGTTTCTTTCG

CGTGCATAAGCCGCTGCGTAGCTATGTCAATCCGATCATGCCAATCTACT

CGGTGGGTAAGCTTGCCAGTATTGAGTATAAAAAAGCCAGTGCGCCAAAA

GATACCATTTATCACGCCAAAGACGCGGTACAAGCAACCAAGCCTGATAT

GCGTAAGCCACGCCTAGTGGTGTTCGTCGTCGGTGAGACGGCACGCGCCG

ATCATGTCAGCTTCAATGGCTATGAGCGCGATACTTTCCCACAGCTTGCC

AAGATCGATGGCGTGACCAATTTTAGCAATGTCACATCGTGCGGCACATC

GACGGCGTATTCTGTGCCGTGTATGTTCAGCTATCTGGGCGCGGATGAGT

ATGATGTCGATACCGCCAAATACCAAGAAAATGTGCTGGATACGCTGGAT

CGCTTGGGCGTAAGTATCTTGTGGCGTGATAATAATTCGGACTCAAAAGG

CGTGATGGATAAGCTGCCAAAAGCGCAATTTGCCGATTATAAATCCGCGA

CCAACAACGCCATCTGCAACACCAATCCTTATAACGAATGCCGCGATGTC

GGTATGCTCGTTGGCTTAGATGACTTTGTCGCTGCCAATAACGGCAAAGA

TATGCTGATCATGCTGCACCAAATGGGCAATCACGGGCCTGCGTATTTTA

AGCGATATGATGAAAAGTTTGCCAAATTCACGCCAGTGTGTGAAGGTAAT

GAGCTTGCCAAGTGCGAACATCAGTCCTTGATCAATGCTTATGACAATGC

CTTGCTTGCCACCGATGATTTCATCGCTCAAAGTATCCAGTGGCTGCAGA

CGCACAGCAATGCCTATGATGTCTCAATGCTGTATGTCAGCGATCATGGC

GAAAGTCTGGGTGAGAACGGTGTCTATCTACATGGTATGCCAAATGCCTT

TGCACCAAAAGAACAGCGCAGTGTGCCTGCATTTTTCTGGACGGATAAGC

AAACTGGCATCACGCCAATGGCAACCGATACCGTCCTGACCCATGACGCG

ATCACGCCGACATTATTAAAGCTGTTTGATGTCACCGCGGACAAAGTCAA

AGACCGCACCGCATTCATCCGCTGA
and

ATGACATCACATCACTCTTGGTATCGCTATTCTATCAATCCTTTTGTGCT

GATGGGTTTGGTGGCGTTATTTTTGGCAGCGACAGCGAACCTGACATTTT

TTGAAAAAGCGATGGCGGTCTATCCTGTATCGGATAACTTAGGCTTTATC

ATCTCAATGGCGGTGGCGGTGATGGGTGCTATGCTACTGATTGTCGTGCT

GTTATCCTATCGCTATGTGCTAAAGCCTGTCCTGATTTTGCTACTGATTA

TGGGTGCGGTGACGAGCTATTTTACCGATACTTATGGCACGGTCTATGAC

ACCACCATGCTCCAAAATGCCATGCAAACCGACCAAGCCGAGTCTAAGGA

CTTGATGAATTTGGCGTTTTTTGTGCGAATTATCGGGCTTGGCGTGTTGC

CAAGTGTGTTGGTCGCAGTTGCCAAAGTCAATTATCCAACATGGGGCAAA

GGTCTGATTCAGCGTGCGATGACATGGGGTGTCAGCCTTGTGCTGTTGCT

TGTGCCGATTGGACTATTTAGCAGTCAGTATGCGAGTTTCTTTCGGGTGC

ATAAGCCAGTGCGTTTTTATATCAACCCGATTACGCCGATTTATTCGGTG

GGTAAGCTTGCCAGTATCGAGTACAAAAAAGCCACTGCGCCAACAGACAC

CATCTATCATGCCAAAGACGCCGTGCAGACCACCAAGCCGAGCGAGCGTA

AGCCACGCCTAGTGGTGTTCGTCGTCGGTGAGACGGCGCGTGCTGACCAT

GTGCAGTTCAATGGCTATGGCCGTGAGACTTTCCCGCAGCTTGCCAAAGT

-continued

```
TGATGGCTTGGCGAATTTTAGCCAAGTGACATCGTGTGGCACATCGACGG

CGTATTCTGTGCCGTGTATGTTCAGCTATTTGGGTCAAGATGACTATGAT

GTCGATACCGCCAAATACCAAGAAAATGTGCTAGATACGCTTGACCGCTT

GGGTGTGGGTATCTTGTGGCGTGATAATAATTCAGACTCAAAAGGCGTGA

TGGATAAGCTACCTGCCACGCAGTATTTTGATTATAAATCAGCAACCAAC

AATACCATCTGTAACACCAATCCCTATAACGAATGCCGTGATGTCGGTAT

GCTTGTCGGGCTAGATGACTATGTCAGCGCCAATAATGGCAAAGATATGC

TCATCATGCTACACCAAATGGGCAATCATGGGCCGGCGTACTTTAAGCGT

TATGATGAGCAATTTGCCAAATTCACCCCCGTGTGCGAAGGCAACGAGCT

TGCCAAATGCGAACACCAATCACTCATCAATGCCTATGACAATGCGCTAC

TTGCGACTGATGATTTTATCGCCAAAAGCATCGATTGGCTAAAAACGCAT

GAAGCGAACTACGATGTCGCCATGCTCTATGTCAGTGACCACGGCGAGAG

CTTGGGCGAAAATGGTGTCTATCTGCATGGTATGCCAAATGCCTTTGCAC

CAAAAGAACAGCGAGCTGTGCCTGCGTTTTTTGGTCAAATAATACGACA

TTCAAGCCAACTGCCAGCGATACTGTGCTGACGCATGATGCGATTACGCC

AACACTGCTTAAGCTGTTTGATGTCACAGCGGGCAAGGTCAAAGACCGCG

CGGCATTTATCCAGTAA.
```

The DNA control mix may include the following internal control sequence: GAGAGGATGACCAGCCACACTG-GAACTGAGACACGGTCCAGACTCCTACGGGAG GCAGCAGTGGGGAATATTGCACAATGGGCG. A DNA control mix may include a combination of the one or more said group of sequences and the said internal control sequence. [SEQ. ID NOS 290-292]

In one example, the kit includes one primer-probe multiplex mix vial including internal control and one DNA control mix vial. A primer-probe mix may include sequences for detecting TEM-like and SHV-like gene families and internal control.

The primer-probe mix may include primers and/or probes selected from the group consisting of: AGATCAGTTGGGTGCACG, TGCTTAATCAGT-GAGGCACC, /56-FAM/ATGAAGCCA/ZEN/TAC-CAAACGACGAGC/3IABkFQ/, CTGGAGCGAAA-GATCCACTA, ATCGTCCACCATCCACTG, and /5HEX/CCAGATCGG/ZEN/CGACAACGTCACC/3IABkFQ/.

The primer-probe mix may include one or more internal controls selected from the group consisting of: GAGAG-GATGAYCAGCCACAC, CGCCCATTGTSCAATATTCC and 5TYE665/TGAGACACGGTCCAGACTCCTACG/3IAbRQSp. The primer-probe mix may include a combination of the one or more said group of primers and/or probes and the one or more said group of internal controls. The primer-probe mix including internal controls may be a multiplex mix. [SEQ. ID NOS 240-248]

A DNA control mix may include one or more sequences selected from the group consisting of: AGATCAGTTGGGTGCACGAGTGGGTTA-CATCGAACTGGATCTCAACAGCGGTAAG ATCCTT-GAGAGTTTTCGCCCCGAAGAACGTTTTCCAATGAT-GAGCACTTTTAAAGTT CTGCTATGTGGTGCGGTAT-TATCCCGTGTTGACGCCGGGCAAGAGCAACTCGGT C GCCGCATACACTATTCTCAGAATGACTTGGTT-GAGTACTCACCAGTCACAGAAAAG CATCTTACG-GATGGCATGACAGTAAGAGAATTATGCAGTGCTGC-CATAACCATGAG TGATAACACTGCGGCCAACTTACTTCTGACAAC-GATCGGAGGACCGAAGGAGCTA ACCGCTTTTTTGCACAACATGGGGGAT-CATGTAACTCGCCTTGATCGTTGGGAACC GGAGCT-GAATGAAGCCATACCAAACGACGAGCGTGACAC-CACGACGCCTGCAGC AATGGCAACAACGTTGCGCAAACTAT-TAACTGGCGAACTACTTACTCTAGCTTCCC GGCAACAATTAATAGACTGGATGGAGGCGGA-TAAAGTTGCAGGACCACTTCTGCG CTCGGCCCTTCCGGCTGGCTGGTTTATTGCTGA-TAAATCTGGAGCCAGTGAGCGT GGGTCTCGCGGTATCATTGCAGCACTGGGGCCA-GATGGTAAGCCCTCCCGTATCG TAGTTATCTA-CACGACGGGGAGTCAGGCAACTATGGAT-GAACGAAATAGACAGATC GCTGAGATAGGTGCCTCACTGATTAAGCA and CTG-GAGCGAAAGATCCACTATCGCCAGCAG-GATCTGGTGGACTACTCGCCGGTCA GCGAAAAACACCTTGCCGACGG-CATGACGGTCGGCGAACTCTGCGCCGCCGCCA TTACCATGAGCGATAACAGCGCCGC-CAATCTGCTGCTGGCCACCGTCGGCGGCC CCGCAGGATTGACTGCCTTTTTGCGCCA-GATCGGCGACAACGTCACCCGCCTTGA CCGCTGG-GAAACGGAACTGAAT-GAGGCGCTTCCCGGCGACGCCCGCGACACCAC TACCCCGGCCAG-CATGGCCGCGACCCTGCGCAAGCTGCTGACCAGC-CAGCGTCT GAGCGCCCGTTCGCAACGGCAGCTGCTGCAGTG-GATGGTGGACGAT. The DNA control mix may include the following internal control sequence: GAGAG-GATGACCAGCCACACTGGAACTGA-GACACGGTCCAGACTCCTACGGGAG GCAGCAGTGGGGAATATTGCACAATGGGCG. A DNA control mix may include a combination of the one or more said group of sequences and the said internal control sequence. [SEQ. ID NOS 293-295]

The primer-probe multiplex mix may comprise different oligonucleotide sequences. An oligonucleotide sequence may be utilized as a primer. An oligonucleotide sequence may be utilized as a probe. An oligonucleotide sequence may be utilized as an internal control sequence. The oligonucleotide concentration of a primer and/or probe sequence may range from 0.05 μM to 60 μM. For example, the oligonucleotide concentration of a primer and/or probe sequence may range from 3 μM to 8 μM. For example, the oligonucleotide concentration of an internal control sequence may range from 2 μM to 6 μM. For example, the oligonucleotide concentration of an internal control sequence may range from 2 μM to 8 μM. The vial oligonucleotide concentrations may be prepared as a 10× stock solution.

The synthetic gene size of a DNA control sequence may be from about 84 bp to about 533 bp. The concentration of a DNA control sequence may be about 25 ng/μl. The concentration of a DNA control sequence may be from 0.033 ng/μL to about 0.5 ng/μl.

The present teachings provide methods for detection of β-lactamase gene families from a biological sample. Preferably, the sample includes Gram-negative bacteria. The method may include sample processing. The method may include extracting DNA from the sample. The method may include extracting RNA from the sample. The method may include the use of assays of the present teachings. The assays may be included in a kit or kits. The method may include employing the kit of the present teachings for the detection of multiple β-lactamase gene families from a biological sample.

The method may include employing the kit for analysis of nucleic acid contained in a clinical sample. The method may include employing the kit for analysis of DNA extracted from a clinical sample. The method may include employing the kit for analysis of DNA extracted from an overnight bacterial culture of a clinical sample.

The method may include amplifying a targeted DNA sequence by real-time polymerase reaction. The method may include amplifying several targeted DNA sequences by multiplex real-time polymerase reaction. The method may include analyzing the amplified sequences or amplicons. The method may include detecting the presence or absence of β-lactamase genes. The method may include detecting the presence or absence of ampC β-lactamase genes. The method may include identifying up to six β-lactamase gene families. The method may include identifying up to nine β-lactamase gene families. The method may include identifying up to fifteen β-lactamase gene families. The method may include identifying up to twenty β-lactamase gene families. The method may include identifying from about six to about thirty β-lactamase gene families. The method may include analyzing collected data.

Examples of real-time PCR amplification curves obtained on the ABI QS7 Flex-Real-Time System for some of the multiplex mixes described herein are shown in FIGS. 1-9. FIG. 1 depicts an amplification plot of an exemplary mix 1 including ampC gene targets. FIG. 2 depicts an amplification plot of an exemplary mix 2 including ampC gene targets. FIG. 3 depicts an amplification plot of an exemplary mix 1 including β-lactamase gene targets. FIG. 4 depicts an amplification plot of an exemplary mix 2 including β-lactamase gene targets. FIG. 5 depicts an amplification plot of an exemplary mix 3 including β-lactamase gene targets. FIG. 6 depicts an amplification plot of an exemplary internal control mix including MCR gene targets. FIG. 7 depicts an amplification plot of an exemplary mix 1 including OXA gene targets. FIG. 8 depicts an amplification plot of an exemplary mix 2 including OXA gene targets. FIG. 9 depicts an amplification plot of an exemplary internal control mix including SHV-TEM gene targets.

The method may include using one or more oligonucleotide primers that are complementary to at least a portion of the nucleic acid sequence of interest. The method may include annealing several pairs of primers to different target DNA sequences. The method may include annealing primer/probe sequences to bacterial nucleic acid sequences comprising targeted antibiotic resistant gene family variants of β-lactamases. The primer and/or probe sequences may anneal with 100% specificity to the target gene variants. The primer and/or probe sequences may anneal with about 95% specificity to the target gene variants. The primer and/or probe sequences may anneal with about 90% to about 100% specificity to the target gene variants. The primer and/or probe sequences may anneal with about 80% to about 100% specificity to the target gene variants.

The method may include using temperature mediated DNA polymerase. The method may include using fluorescent dyes. The method may include the using sequence specific DNA probes including oligonucleotides labeled with a reporter. The method may include using a microarray.

The method may include using a thermal cycler. For example, the kit of the present teachings may be utilized with the following PCR systems: Streck ZULU RT™ PCR System, Applied Biosystems (ABI) QuantStudio 7 (QS7) Flex Real-Time System, ABI 7500 Real-Time PCR System, QIAGEN Rotor-Gene® Q, and CFX96 Touch™ Real-Time PCR Detection System, Applied Biosystems™ 7500 Fast Dx Real-Time PCR Instrument, Roche LightCycler® 480 I and II, and Cepheid SmartCycler®. It is contemplated that any detection system capable of detecting the multiplex fluorescent signal provided in the kit of the present teachings may be suitable.

The method may include real-time monitoring of qPCR reaction products. The probes may generate a signal when hydrolyzed by the DNA polymerase causing liberation of a detectable fluorescent signal. The real-time monitoring method may employ fluorescence at different wavelengths. The method may include the use of DNA-intercalating fluorescent dyes. The method may include the use of a target specific nucleotide probe labeled with a fluorescent tag at one end. The other end of the hybridization probe may be labeled with a fluorescent quencher. Fluorescent hybridization probes generate a fluorescence signal only when they bind to their target and enable real-time of monitoring of nucleic acid amplification assays.

Surprisingly, some DNA targets detected with these kits, allow for amplification of regions of DNA much larger than the conventional wisdom within the real-time PCR field. For example, most amplicons would traditionally be between 50 to 150 base pairs in size. The present teachings allow for successfully amplified amplicons up to 553 base pairs by real-time PCR.

There may be one or more benefits to detecting larger amplicons. Larger amplicons may, in some cases, provide greater specificity for a specific antibiotic resistance gene family. Detection of larger amplicons may permit detection of an increased number of gene variants within a given resistance gene family. Detection of larger amplicons may also allow confirmation by agarose gel electrophoresis since the molecular sizes of each gene that is detected can be resolved from one another.

The efficiency of detection for each target in a dilution series may be measured for amplicons between 25 base pairs and 2000 base pairs. The efficiency of the PCR for amplicons within this size range may be from 80% to 110%. More specifically, the efficiency of the reactions may be from 90% to 105%. The coefficient of determination may be from 0.98 to 1.1. More specifically, the coefficient of determination may be from 0.99 to 1.0. The limit of detection may be from 0.1 copies to $1 \times 10^{10}$ copies.

Alternate sequences for primer, probes, and DNA controls for β-lactamase gene targets of the present teachings are depicted in Table 2 and Table 3. [SEQ. ID NOS 1-48 and SEQ. ID NOS 49-66]

Primers and/or probes may be degenerate at any nucleotide position. Primers and/or probes may not be degenerate at any nucleotide position. Any suitable fluorophore and/or quencher and nucleic acid sequence combination may be used. For example, a probe may be labeled with a fluorescent tag at one end and a fluorescent quencher at the other end. For example, a probe may be labeled with a fluorescent tag at one end and a fluorescent quencher at the other end. For example, two fluorescent quenchers may be included at one end or within the probe sequence. It is contemplated that the probe sequences of the present teachings may be labeled with any suitable fluorophore and quencher combinations. For example, any fluorophore of the present teachings may be attached to any probe DNA sequence of the present teachings.

TABLE 2

| | Primer/Probe | Sequence |
|---|---|---|
| SEQ ID NO. 1 | MOX F' | AGA CCC TGT TCG AGA TAG |
| SEQ ID NO. 2 | MOX R' | ATG GTG ATG CTG TCA AAG |
| SEQ ID NO. 3 | MOX-FAM | 5'-56-FAM-CGT GAG CAA GAC CCT GAC TG-3'BHQ1 |
| SEQ ID NO. 4 | FOX F' | ACT ATT TCA ACT ATG GGG TT |
| SEQ ID NO. 5 | FOX R' | TTG TCA TCC AGC TCA AAG |
| SEQ ID NO. 6 | FOX-TEX | 5'-Tex615-TGA CCG CAG CAT AGG CAC-3'BHQ_2 |
| SEQ ID NO. 7 | EBC F' | GTG GCG GTG ATT TAT GAG |
| SEQ ID NO. 8 | EBC R' | CGG TGA AGG TTT TAC TTA TAG AA |
| SEQ ID NO. 9 | EBC-HEX | 5'-5HEX/CAGCCGCAC/ZEN/TACTTCACCT/-3'BHQ_1 |
| SEQ ID NO. 10 | DHA F' | TGCGTACGGTTATGAGAACAA |
| SEQ ID NO. 11 | DHA R' | CCCAGCGCAGCATATCTT |
| SEQ ID NO. 12 | DHA-FAM | ATGCGGAATCTTACGGCGTGGAAT |
| SEQ ID NO. 13 | CMY F' | TCC AGC GTT ATT GAT ATG G |
| SEQ ID NO. 14 | CMY R' | CAT CTC CCA GCC TAA TCC |
| SEQ ID NO. 15 | CMY-TEX | 5'TexRd-XN/ACATATCGCCAATACGCCAGT/3IAPRQSp/-3' |
| SEQ ID NO. 16 | ACC F' | GCCGCTGATGCAGAAGAATA |
| SEQ ID NO. 17 | ACC R' | TTT GCC GCT AAC CCA TAG TT |
| SEQ ID NO. 18 | ACC-HEX | 5'-/5HEX/TCA CTG CGA/ZEN/CCG ACA TAC CG/3IABkFQ/-3' |
| SEQ ID NO. 19 | IC F' | GAG AGG ATG ACC AGC CAC AC |
| SEQ ID NO. 20 | IC R' | AGT ACT TTA CAA CCC GAA GGC |
| SEQ ID NO. 21 | IC-TYE | 5'/5TYE665/TGA GAC ACG GTC CAG ACT CCT ACG G/3BHQ_2/-3' |
| SEQ ID NO. 22 | CTX-M-14 F' | 5'-TTGGTGACGTGGCTCAAA-3' |
| SEQ ID NO. 23 | CTX-M-14 R' | 5'-ATATCATTGGTGGTGCCGTAG-3' |
| SEQ ID NO. 24 | CTX-M-14-FAM | 5'-/56-FAM/CGTGGACTG/ZEN/TGGGTGATAAGACCG/3IABkFQ/-3' |
| SEQ ID NO. 25 | CTX-M-15 F' | 5'-GTCACGCTGTTGTTAGGAAGT-3' |
| SEQ ID NO. 26 | CTX-M-15 R' | 5'-TAATCAATGCCACACCCAGTC-3' |
| SEQ ID NO. 27 | CTX-M-15-TEX615 | 5'-/5TEX615/AACTTGCCGAATTAGAGCGGCAGT/3BHQ_2/-3' |
| SEQ ID NO. 28 | OXA48-F' | 5'-AGCAGCAAGGATTTACCAATAATC-3' |
| SEQ ID NO. 29 | OXA48-R' | 5'-CGTCTGTCCATCCCACTTAAA-3' |
| SEQ ID NO. 30 | OXA48-HEX | 5'-/5HEX/TAGCTTGAT/ZEN/CGCCCTCGATTTGGG/3IABkFQ/-3' |
| SEQ ID NO. 31 | CMY F' | 5'-TCCAGCGTTATTGATATGG-3' |
| SEQ ID NO. 32 | CMY R' | 5'-CATCTCCCAGCCTAATCC-3' |
| SEQ ID NO. 33 | CMY-TxR | 5-/5TexRd-XN/ACATATCGCCAATACGCCAGT/3IAbRQSp/-3' |
| SEQ ID NO. 34 | NDM F' | 5'-TTTGATCGTCAGGGATGGC-3' |
| SEQ ID NO. 35 | NDM R' | 5'-CAGGTTGATCTCCTGCTTGAT-3' |
| SEQ ID NO. 36 | NDM-HEX | 5-/5HEX/AGACCGCCC/ZEN/AGATCCTCAACTG/3IABkFQ/-3' |

TABLE 2-continued

| | Primer/Probe | Sequence |
|---|---|---|
| SEQ ID NO. 37 | KPC F' | 5'-CGCTAAACTCGAACAGGACTT-3' |
| SEQ ID NO. 38 | KPC R' | 5'-TAACTTACAGTTGCGCCTGAG-3' |
| SEQ ID NO. 39 | KPC-FAM | 5'-/5TYE665/ATCGGTGTGTACGCGATGGATACC/3BHQ_2/-3' |
| SEQ ID NO. 40 | VIM F' | 5'-CATTCGACCGACAACTTAG-3' |
| SEQ ID NO. 41 | VIM R' | 5'-CGTGCGTGACAACTCAT-3' |
| SEQ ID NO. 42 | VIM-TEX | 5'45TEX615/TGTGCTCTATGGTGGTTGTGCGAT/3BHQ_2/-3' |
| SEQ ID NO. 43 | DHA F' | 5'-TGCGTACGGTTATGAGAACAA-3' |
| SEQ ID NO. 44 | DHA R' | 5'-CCCAGCGCAGCATATCTT-3' |
| SEQ ID NO. 45 | DHA-FAM | 5'-/56-FAM/ATGCGGAAT/ZEN/CTTACGGCGTGAAAT/3IABkFQ-3' |
| SEQ ID NO. 46 | IMP F' | 5'-ACGTAGTGGTTTGGTTACCTG-3' |
| SEQ ID NO. 47 | IMP R' | 5'-AAGCTTCTAAATTTGCGTCACC-3' |
| SEQ ID NO. 48 | IMP-TYE705 | 5'-/5HEX/TTTGTTAAA/ZEN/CCGGACGGTCTTGGT/3IABkFQ/-3' |

TABLE 3

| | DNA Control | Sequence |
|---|---|---|
| SEQ ID NO. 49 | MOX | AACCGGGAGAGCGGGGCCAGCGTCAGCGAGCAGACCCTGTTCGAGATAGGATCCGTGAGCAAGACCCTGACTGCGACCCTGGGGGCCTATGCGGTGGTCAAGGGAGCGATGCAGCTGGATGACAAGGCGAGCCGGCACGCGCCCTGGCTCAAGGGATCCGTCTTTGACAGCATCACCATGGGGGAGCTTGCCACCTACAGC |
| SEQ ID NO. 50 | FOX | GGGGATGGCGGTCGCCGTGCTGAAAGATGGCAAGGCCCACTATTTCAACTATGGGGTTGCCAACCGCGAGAGTGGTCAGCGCGTCAGCGAGCAGACCCTGTTCGAGATTGGCTCGGTCAGCAAGACCCTGACCGCGACCCTCGGTGCCTATGCTGCGGTCAAGGGGGGCTTTGAGCTGGATGACAAGGTGAGCCAGCACGCCCCCTGGCTCAAAGGTTCCGCCTTTGATGGTGTGACCAT |
| SEQ ID NO. 51 | EBC | GGACCGTTACGCCGCTGATGAAAGCGCAGGCCATTCCGGGTATGGCGGTGGCGGTGATTTATGAGGGTCAGCCGCACTACTTCACCTTCGGTAAAGCCGATGTTGCGGCGAACAAACCTGTCACTCCACAAACCTTGTTCGAACTGGGTTCTATAAGTAAAACCTTCACCGGCGTACTCGGTGGCGATGCCATTGCTCGCGGTGAAATATCGCTGGGCGA |
| SEQ ID NO. 52 | DHA | GACTGCACGGATCCTGGCACCGCTGGGGTTATCTCACACCTTTATTACTGTGCCGGAAAGTGCGCAAAGCCAGTATGCGTACGGTTATGAGAACAAAAACCGGTCCGCGTGTCGCCGGGACAGCTTGATGCGGAATCTTACGGCGTGGAATCGCCTCAAAAGATATGCTGCGCTGGGCGGAAATGAATATGGAGCCGTCACGGGCCGGTAATGCGGAT |
| SEQ ID NO. 53 | CMY | GCCTGTACACGTTTCTCCGGGACAACTTGACGCCGAAGCCTATGGCGTGAAATCCAGCGTTATTGATATGGCCCGCTGGGTTCAGGTCAACATGGACGCCAGCCGCGTTCAGGAGAAAACGCTCCAGCAGGGCATTGCGCTTGCGCAGTCTCGCTACTGGCGTATTGGCGATATGTACCAGGGATTAGGCTGGGAGATGCTGAACTGGCCGCTGAAAGCTGATTCGATCATCAACGGTAGCGACAGCAAAGTGGCATTGG |
| SEQ ID NO. 54 | ACC | GAGAGCAAAATTAAAGACACCGTTGATGACCTGATCCAGCCGCTGATGCAGAAGAATAATATTCCCGGTATGTCGGTCGCAGTGACCGTCAACGGTAAAAACTACATTTATAACTATGGGTTAGCGGCAAAACAGCCTCAGCAGCCGGTT |
| SEQ ID NO. 55 | IC | AGCTTGTTGGTGGGGTAACGGCTCACCAAGGCGACGATCCCTAGCTGGTCTGAGAGGATGACCAGCCACACTGGAACTGAGACACGGTCCAGACTCCTACGGGAGGCAGCAGTGGGGAATATTGCACAATGGGCGCAAGCCTGATGCAGCCATGCCGCGTGTATGAAGAAGGCCTTCGGGTTGTAAAGTACTTTCAGCGGGGAGGAAGGGAGTAAAGTTAATACCCTTTGCTCATTGACGTTACCCGCAGAAGAAGCACCGGCTAACTCCG |

TABLE 3-continued

| | DNA Control | Sequence |
|---|---|---|
| SEQ ID NO. 56 | CTX-M-14 | CGTTTCGTCTGGATCGCACTGAACCTACGCTGAATACCGCCATTCCCGGCG<br>ACCCGAGAGACACCACCACGCCGCGGGCGATGGCGCAGACGTTGCGTCA<br>GCTTACGCTGGGTCATGCGCTGGGCGAAACCCAGCGGGCGCAGTTGGTG<br>ACGTGGCTCAAAGGCAATACGACCGGCGCAGCCAGCATTCGGGCCGGCTT<br>ACCGACGTCGTGGACTGTGGGTGATAAGACCGGCAGCGGCGACTACGGC<br>ACCACCAATGATATTGCGGTGATCTGGCCGCAGGGTCGTGCGCCGCTGGT<br>TCTGGTGACCTATTTTACCCAGC |
| SEQ ID NO. 57 | CTX-M-15 | CCGTCACGCTGTTGTTAGGAAGTGTGCCGCTGTATGCGCAAACGGCGGAC<br>GTACAGCAAAAACTTGCCGAATTAGAGCGGCAGTCGGGAGGCAGACTGG<br>GTGTGGCATTGATTAACACAGC |
| SEQ ID NO. 58 | OXA | AATCACAGGGCGTAGTTGTGCTCTGGAATGAGAATAAGCAGCAAGGATTT<br>ACCAATAATCTTAAACGGGCGAACCAAGCATTTTTACCCGCATCTACCTTTA<br>AAATTCCCAATAGCTTGATCGCCCTCGATTTGGGCGTGGTTAAGGATGAAC<br>ACCAAGTCTTTAAGTGGGATGGACAGACGCGCGATATCGCCACTTGGAAT<br>CGCGATCATAATCTAATCACCGCGATGAAATATTCAGTTGTGCCTGTTTAT<br>CAAGAATTTGCCCGCCAAATTGGCGAGGCACGTATGAGCAAGATGCTACA<br>TGCTTTCGATTATGGTAATGAGGACATTTCGGGCAATGTAGACAGTTTCTG<br>GCTCGACGGTGGTATTCGAATTTCGGCCACGGAGCAAATCAGCTTTTTAA<br>GAAAGCTGTATCACAATAAGTTACACGTATCGGAGCGCAGCCAGCGTATT<br>GTCAAACAAGCCATGCTGACCGAAGCCAATGGTGACTAATTATTCGGGCT<br>AAAACTGGATACTCGACTAGAATCGAACCTAAGATTGGCTGGCTGGGT |
| SEQ ID NO. 59 | IC | CGGAGTTAGCCGGTGCTTCTTCTGCGGGTAACGTCAATGAGCAAAGGTAT<br>TAACTTTACTCCCTTCCTCCCCGCTGAAAGTACTTTACAACCCGAAGGCCTT<br>CTTCATACACGCGGCATGGCTGCATCAGGCTTGCGCCCATTGTGCAATATT<br>CCCCACTGCTGCCTCCCGTAGGAGTCTGGACCGTGTCTCAGTTCCAGTGTG<br>GCTGGTCATCCTCTCAGACCAGCTAGGGATCGTCGCCTTGGTGAGCCGTTA<br>CCCCACCAACAAGCT |
| SEQ ID NO. 60 | CMY | GCCTGTACACGTTTCTCCGGGACAACTTGACGCCGAAGCCTATGGCGTGA<br>AATCCAGCGTTATTGATATGGCCCGCTGGGTTCAGGTCAACATGGACGCC<br>AGCCGGCGTTCAGGAGAAAACGCTCCAGCAGGGCATTGCGCTTGCGCAGTC<br>TCGCTACTGGCGTATTGGCGATATGTACCAGGGATTAGGCTGGGAGATGC<br>TGAACTGGCCGCTGAAAGCTGATTCGATCATCAACGGTAGCGACAGCAAA<br>GTGGCATTGG |
| SEQ ID NO. 61 | NDM | GGCGAAAGTCAGGCTGTGTTGCGCCGCAACCATCCCCTCTTGCGGGGCAA<br>GCTGGTTCGACAACGCATTGGCATAAGTCGCAATCCCCGCCGCATGCAGC<br>GCGTCCATACCGCCCATCTTGTCCTGATGCGCGTGAGTCACCACCGCCAGC<br>GCGACCGGCAGGTTGATCTCCTGCTTGATCCAGTTGAGGATCTGGGCGGT<br>CTGGTCATCGGTCCAGGCGGTATCGACCACCAGCACGCGGCCGCCATCCC<br>TGACGATCAAAC |
| SEQ ID NO. 62 | KPC | GTATCGCCGTCTAGTTCTGCTGTCTTGTCTCTCATGGCCGCTGGCTGGCTTT<br>TCTGCCACCGCGCTGACCAACCTCGTCGCGGAACCATTCGCTAAACTCGAA<br>CAGGACTTTGGCGGCTCCATCGGTGTGTACGCGATGGATACCGGCTCAGG<br>CGCAACTGTAAGTTACCGCGCTGAGGAGCGCTTCCCACTGTGCAGCTCATT<br>CAAGG |
| SEQ ID NO. 63 | VIM | CCATTCAGCCAGATCGGCATCGGCCACGTTCCCCGCAGACGTGCGTGACA<br>ACTCATGAATCGCACAACCACCATAGAGCACACTCGCGAGACGGGACGTAC<br>ACAACTAAGTTGTCGGTCGAATGCGCAGCACCAGGATAGAAGAGTTCTAC<br>TGGACCGAAGCGCACTGCGTCCCCGCTCGAGTCCTTCTAGAGAGTGCGTG<br>GGAATCTCGTTCCCCTCTACCTCGGCTAGCCGGCGTGTCGACGGTGATGC<br>GTACGTTGCCACCCCAGCCGCCCGAAGGACATCAACGCCGCC |
| SEQ ID NO. 64 | DHA | GACTGCACGGATCCTGGCACCGCTGGGGTTATCTCACACCTTTATTACTGT<br>GCCGGAAAGTGCGCAAAGCCAGTATGCGTACGGTTATGAGAACAAAAAA<br>CCGGTCCGCGTGTCGCCGGGACAGCTTGATGCGGAATCTTACGGCGTGAA<br>ATCCGCCTCAAAAGATATGCTGCGCTGGGCGGAAATGAATATGGAGCCGT<br>CACGGGCCGGTAATGCGGAT |
| SEQ ID NO. 65 | IC | CGGAGTTAGCCGGTGCTTCTTCTGCGGGTAACGTCAATGAGCAAAGGTAT<br>TAACTTTACTCCCTTCCTCCCCGCTGAAAGTACTTTACAACCCGAAGGCCTT<br>CTTCATACACGCGGCATGGCTGCATCAGGCTTGCGCCCATTGTGCAATATT<br>CCCCACTGCTGCCTCCCGTAGGAGTCTGGACCGTGTCTCAGTTCCAGTGTG<br>GCTGGTCATCCTCTCAGACCAGCTAGGGATCGTCGCCTTGGTGAGCCGTTA<br>CCCCACCAACAAGCT |
| SEQ ID NO. 66 | IMP | GCGGAGTTAGTTATTGGCTAGTTAAAAATAAAATTGAAGTTTTTATCCCG<br>GCCCGGGGCACACTCAAGATAACGTAGTGGTTTGGTTACCTGAAAAGAAA<br>ATTTTATTCGGTGGTTGTTTTGTTAAACCGGACGGTCTTGGTAATTTGGGT<br>GACGCAAATTTAGAAGCTTGGCC |

The sequence listing including SEQ ID NOS 1-295 is hereby incorporated by reference for all purposes.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01, or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the of a range in terms of "at least 'x' parts by weight of the resulting composition" also contemplates a teaching of ranges of same recited amount of "x" in percent by weight of the resulting composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for ail purposes. The term "consisting essentially of to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist of, or consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

---

The invention claimed is:

1. A kit for identification of one or more β-lactamase genes, wherein the one or more β-lactamase genes are selected from the group consisting of: CMY, CTX-M, OXA, IMP, VIM, DHA, KPC, and NDM genes, the kit comprising probes comprising the following sequences: ACGCTAACTCCAGCATTGGTCTGT (SEQ ID NO: 154), AACTTGCCGAATTAGAGCRGCAGT (SEQ ID NO: 157), TATCATTGGTGGTGCCGTAGTCGC (SEQ ID NO: 160), TGAGACACGGTCCAGACTCCTACG (SEQ ID NO: 163), TAGCTTGATCGCCCTCGATTTGGG (SEQ ID NO: 166), TTRTTYGGTGGTTGYTTTRTTAA (SEQ ID NO: 169), CCGGACGGTCTTGGTAATTTGGGT (SEQ ID NO: 172), CCGTACGGTTTAGGCAATTTGGGT (SEQ ID NO: 173), AGCTCTTCTATCCTGGTGCTGCG (SEQ ID NO: 176), TGAGACACGGTCCAGACTCCTACG (SEQ ID NO: 179), AAACCGGGCGATATGCGTCTGTAT (SEQ ID NO: 182), TCGTCGCGGAACCATTCGCTAAA (SEQ ID NO: 185), CATCAGGACAAGATGGGCGGTATG (SEQ ID NO: 188), and TGAGACACGGTCCAGACTCC-TACG (SEQ ID NO: 191), wherein each probe comprises a fluorophore and/or a fluorescent quencher.

2. The kit of claim 1, including an endogenous internal control.

3. The kit of claim 2, wherein the endogenous internal control targets a conserved region in Gram-negative bacteria.

4. The kit of claim 1, further comprising the following primers: TGGCCAGAACTGACAGGCAAA (SEQ ID NO: 152), TTTCTCCTGAACGTGGCTGGC (SEQ ID NO: 153), CCGTCACGCTGTTGTTAGG (SEQ ID NO: 155), GCTGTGTTAATCAATGCCACAC (SEQ ID NO: 156), CGTTTCGTCTGGATCGCAC (SEQ ID NO: 158), GCTGGGTAAAATAGGTCACC (SEQ ID NO: 159), GAGAGGATGAYCAGCCACAC (SEQ ID NO: 161), and CGCCCATTGTSCAATATTCC (SEQ ID NO: 162).

5. The kit of claim 4, further comprising the following primers: AATCACAGGGCGTAGTTGTG (SEQ ID NO: 164), ACCCACCAGCCAATCTTAGG (SEQ ID NO: 165), GCGGAGTTAACTATTGGCTAG (SEQ ID NO: 167), GGCCAAGCTTCTATATTTGCG (SEQ ID NO: 168), GCGGAGTTARYTATTGGCTAG (SEQ ID NO: 170), GGCCAAGCYTCTAWATTTGCG (SEQ ID NO: 171), GGCGGCGTTGATGTCCTTCG (SEQ ID NO: 174), CCATTCAGCCAGATCGGCATC (SEQ ID NO: 175), GAGAGGATGAYCAGCCACAC (SEQ ID NO: 177), and CGCCCATTGTSCAATATTCC (SEQ ID NO: 178).

6. The kit of claim 5, further comprising the following primers: AACTTTCACAGGTGTGCTGGGT (SEQ ID NO: 180), CCGTACGCATACTGGCTTTGC (SEQ ID NO: 181), GTATCGCCGTCTAGTTCTGC (SEQ ID NO: 183), CCTT-GAATGAGCTGCACAGTGG (SEQ ID NO: 184), GTTT-GATCGTCAGGGATGGC (SEQ ID NO: 186), GGCGAAAGTCAGGCTGTG (SEQ ID NO: 187), GAGAGGATGAYCAGCCACAC (SEQ ID NO: 189), and CGCCCATTGTSCAATATTCC (SEQ ID NO: 190).

7. The kit of claim 1, including at least one control DNA mix.

8. The kit of claim 1, including exactly two control DNA mixes.

9. The kit of claim 1, including exactly three control DNA mixes.

10. The kit of claim 1, including a composition containing a tracking dye.

* * * * *

SEQUENCE LISTING

```
Sequence total quantity: 302
SEQ ID NO: 1              moltype = DNA  length = 18
FEATURE                   Location/Qualifiers
misc_feature              1..18
                          note = MOX F'
source                    1..18
                          mol_type = other DNA
                          organism = synthetic construct
SEQUENCE: 1
agaccctgtt cgagatag                                                 18

SEQ ID NO: 2              moltype = DNA  length = 18
FEATURE                   Location/Qualifiers
misc_feature              1..18
                          note = MOX R'
source                    1..18
                          mol_type = other DNA
                          organism = synthetic construct
SEQUENCE: 2
atggtgatgc tgtcaaag                                                 18

SEQ ID NO: 3              moltype = DNA  length = 20
FEATURE                   Location/Qualifiers
misc_feature              1..20
                          note = MOX-FAM
source                    1..20
                          mol_type = other DNA
                          organism = synthetic construct
SEQUENCE: 3
cgtgagcaag accctgactg                                               20

SEQ ID NO: 4              moltype = DNA  length = 20
FEATURE                   Location/Qualifiers
```

```
misc_feature            1..20
                        note = FOX F'
source                  1..20
                        mol_type = other DNA
                        organism = synthetic construct
SEQUENCE: 4
actatttcaa ctatggggtt                                                    20

SEQ ID NO: 5            moltype = DNA  length = 18
FEATURE                 Location/Qualifiers
misc_feature            1..18
                        note = TTG TCA TCC AGC TCA AAG
source                  1..18
                        mol_type = other DNA
                        organism = synthetic construct
SEQUENCE: 5
ttgtcatcca gctcaaag                                                      18

SEQ ID NO: 6            moltype = DNA  length = 18
FEATURE                 Location/Qualifiers
misc_feature            1..18
                        note = FOX-TEX
source                  1..18
                        mol_type = other DNA
                        organism = synthetic construct
SEQUENCE: 6
tgaccgcagc ataggcac                                                      18

SEQ ID NO: 7            moltype = DNA  length = 18
FEATURE                 Location/Qualifiers
misc_feature            1..18
                        note = EBC F'
source                  1..18
                        mol_type = other DNA
                        organism = synthetic construct
SEQUENCE: 7
gtggcggtga tttatgag                                                      18

SEQ ID NO: 8            moltype = DNA  length = 23
FEATURE                 Location/Qualifiers
misc_feature            1..23
                        note = EBC R'
source                  1..23
                        mol_type = other DNA
                        organism = synthetic construct
SEQUENCE: 8
cggtgaaggt tttacttata gaa                                                23

SEQ ID NO: 9            moltype = DNA  length = 19
FEATURE                 Location/Qualifiers
misc_feature            1..19
                        note = EBC-HEX
source                  1..19
                        mol_type = other DNA
                        organism = synthetic construct
SEQUENCE: 9
cagccgcact acttcacct                                                     19

SEQ ID NO: 10           moltype = DNA  length = 21
FEATURE                 Location/Qualifiers
misc_feature            1..21
                        note = DHA F'
source                  1..21
                        mol_type = other DNA
                        organism = synthetic construct
SEQUENCE: 10
tgcgtacggt tatgagaaca a                                                  21

SEQ ID NO: 11           moltype = DNA  length = 18
FEATURE                 Location/Qualifiers
misc_feature            1..18
                        note = DHA R'
source                  1..18
                        mol_type = other DNA
                        organism = synthetic construct
SEQUENCE: 11
cccagcgcag catatctt                                                      18

SEQ ID NO: 12           moltype = DNA  length = 24
```

```
FEATURE                        Location/Qualifiers
misc_feature                   1..24
                               note = DHA-FAM
source                         1..24
                               mol_type = other DNA
                               organism = synthetic construct
SEQUENCE: 12
atgcggaatc ttacggcgtg gaat                                              24

SEQ ID NO: 13                  moltype = DNA   length = 19
FEATURE                        Location/Qualifiers
misc_feature                   1..19
                               note = CMY F'
source                         1..19
                               mol_type = other DNA
                               organism = synthetic construct
SEQUENCE: 13
tccagcgtta ttgatatgg                                                    19

SEQ ID NO: 14                  moltype = DNA   length = 18
FEATURE                        Location/Qualifiers
misc_feature                   1..18
                               note = CMY R'
source                         1..18
                               mol_type = other DNA
                               organism = synthetic construct
SEQUENCE: 14
catctcccag cctaatcc                                                     18

SEQ ID NO: 15                  moltype = DNA   length = 21
FEATURE                        Location/Qualifiers
misc_feature                   1..21
                               note = CMY-TEX
source                         1..21
                               mol_type = other DNA
                               organism = synthetic construct
SEQUENCE: 15
acatatcgcc aatacgccag t                                                 21

SEQ ID NO: 16                  moltype = DNA   length = 20
FEATURE                        Location/Qualifiers
misc_feature                   1..20
                               note = ACC F'
source                         1..20
                               mol_type = other DNA
                               organism = synthetic construct
SEQUENCE: 16
gccgctgatg cagaagaata                                                   20

SEQ ID NO: 17                  moltype = DNA   length = 20
FEATURE                        Location/Qualifiers
misc_feature                   1..20
                               note = ACC R'
source                         1..20
                               mol_type = other DNA
                               organism = synthetic construct
SEQUENCE: 17
tttgccgcta acccatagtt                                                   20

SEQ ID NO: 18                  moltype = DNA   length = 11
FEATURE                        Location/Qualifiers
misc_feature                   1..11
                               note = ACC-HEX
source                         1..11
                               mol_type = other DNA
                               organism = synthetic construct
SEQUENCE: 18
ccgacatacc g                                                            11

SEQ ID NO: 19                  moltype = DNA   length = 20
FEATURE                        Location/Qualifiers
misc_feature                   1..20
                               note = IC F'
source                         1..20
                               mol_type = other DNA
                               organism = synthetic construct
SEQUENCE: 19
gagaggatga ccagccacac                                                   20
```

-continued

```
SEQ ID NO: 20            moltype = DNA  length = 21
FEATURE                  Location/Qualifiers
misc_feature             1..21
                         note = IC R'
source                   1..21
                         mol_type = other DNA
                         organism = synthetic construct
SEQUENCE: 20
agtactttac aacccgaagg c                                              21

SEQ ID NO: 21            moltype = DNA  length = 25
FEATURE                  Location/Qualifiers
misc_feature             1..25
                         note = IC-TYE
source                   1..25
                         mol_type = other DNA
                         organism = synthetic construct
SEQUENCE: 21
tgagacacgg tccagactcc tacgg                                          25

SEQ ID NO: 22            moltype = DNA  length = 18
FEATURE                  Location/Qualifiers
misc_feature             1..18
                         note = CTX-M-14 F'
source                   1..18
                         mol_type = other DNA
                         organism = synthetic construct
SEQUENCE: 22
ttggtgacgt ggctcaaa                                                  18

SEQ ID NO: 23            moltype = DNA  length = 21
FEATURE                  Location/Qualifiers
misc_feature             1..21
                         note = CTX-M-14 R'
source                   1..21
                         mol_type = other DNA
                         organism = synthetic construct
SEQUENCE: 23
atatcattgg tggtgccgta g                                              21

SEQ ID NO: 24            moltype = DNA  length = 24
FEATURE                  Location/Qualifiers
misc_feature             1..24
                         note = CTX-M-14-FAM
source                   1..24
                         mol_type = other DNA
                         organism = synthetic construct
SEQUENCE: 24
cgtggactgt gggtgataag accg                                           24

SEQ ID NO: 25            moltype = DNA  length = 21
FEATURE                  Location/Qualifiers
misc_feature             1..21
                         note = CTX-M-15 F'
source                   1..21
                         mol_type = other DNA
                         organism = synthetic construct
SEQUENCE: 25
gtcacgctgt tgttaggaag t                                              21

SEQ ID NO: 26            moltype = DNA  length = 21
FEATURE                  Location/Qualifiers
misc_feature             1..21
                         note = CTX-M-15 R'
source                   1..21
                         mol_type = other DNA
                         organism = synthetic construct
SEQUENCE: 26
taatcaatgc cacacccagt c                                              21

SEQ ID NO: 27            moltype = DNA  length = 24
FEATURE                  Location/Qualifiers
misc_feature             1..24
                         note = CTX-M-15-TEX615
source                   1..24
                         mol_type = other DNA
                         organism = synthetic construct
SEQUENCE: 27
aacttgccga attagagcgg cagt                                           24
```

| | | |
|---|---|---|
| SEQ ID NO: 28 | moltype = DNA   length = 24 | |
| FEATURE | Location/Qualifiers | |
| misc_feature | 1..24 | |
| | note = OXA48-F' | |
| source | 1..24 | |
| | mol_type = other DNA | |
| | organism = synthetic construct | |
| SEQUENCE: 28 | | |
| agcagcaagg atttaccaat aatc | | 24 |
| | | |
| SEQ ID NO: 29 | moltype = DNA   length = 21 | |
| FEATURE | Location/Qualifiers | |
| misc_feature | 1..21 | |
| | note = OXA48-R' | |
| source | 1..21 | |
| | mol_type = other DNA | |
| | organism = synthetic construct | |
| SEQUENCE: 29 | | |
| cgtctgtcca tcccacttaa a | | 21 |
| | | |
| SEQ ID NO: 30 | moltype = DNA   length = 24 | |
| FEATURE | Location/Qualifiers | |
| misc_feature | 1..24 | |
| | note = OXA48-HEX | |
| source | 1..24 | |
| | mol_type = other DNA | |
| | organism = synthetic construct | |
| SEQUENCE: 30 | | |
| tagcttgatc gccctcgatt tggg | | 24 |
| | | |
| SEQ ID NO: 31 | moltype = DNA   length = 19 | |
| FEATURE | Location/Qualifiers | |
| misc_feature | 1..19 | |
| | note = CMY F' | |
| source | 1..19 | |
| | mol_type = other DNA | |
| | organism = synthetic construct | |
| SEQUENCE: 31 | | |
| tccagcgtta ttgatatgg | | 19 |
| | | |
| SEQ ID NO: 32 | moltype = DNA   length = 18 | |
| FEATURE | Location/Qualifiers | |
| misc_feature | 1..18 | |
| | note = CMY R' | |
| source | 1..18 | |
| | mol_type = other DNA | |
| | organism = synthetic construct | |
| SEQUENCE: 32 | | |
| catctcccag cctaatcc | | 18 |
| | | |
| SEQ ID NO: 33 | moltype = DNA   length = 21 | |
| FEATURE | Location/Qualifiers | |
| misc_feature | 1..21 | |
| | note = CMY-TxR | |
| source | 1..21 | |
| | mol_type = other DNA | |
| | organism = synthetic construct | |
| SEQUENCE: 33 | | |
| acatatcgcc aatacgccag t | | 21 |
| | | |
| SEQ ID NO: 34 | moltype = DNA   length = 19 | |
| FEATURE | Location/Qualifiers | |
| misc_feature | 1..19 | |
| | note = NDM F' | |
| source | 1..19 | |
| | mol_type = other DNA | |
| | organism = synthetic construct | |
| SEQUENCE: 34 | | |
| tttgatcgtc agggatggc | | 19 |
| | | |
| SEQ ID NO: 35 | moltype = DNA   length = 21 | |
| FEATURE | Location/Qualifiers | |
| misc_feature | 1..21 | |
| | note = NDM R' | |
| source | 1..21 | |
| | mol_type = other DNA | |
| | organism = synthetic construct | |
| SEQUENCE: 35 | | |

```
caggttgatc tcctgcttga t                                              21

SEQ ID NO: 36          moltype = DNA   length = 22
FEATURE                Location/Qualifiers
misc_feature           1..22
                       note = NDM-HEX
source                 1..22
                       mol_type = other DNA
                       organism = synthetic construct
SEQUENCE: 36
agaccgccca gatcctcaac tg                                             22

SEQ ID NO: 37          moltype = DNA   length = 21
FEATURE                Location/Qualifiers
misc_feature           1..21
                       note = KPC F'
source                 1..21
                       mol_type = other DNA
                       organism = synthetic construct
SEQUENCE: 37
cgctaaactc gaacaggact t                                              21

SEQ ID NO: 38          moltype = DNA   length = 21
FEATURE                Location/Qualifiers
misc_feature           1..21
                       note = KPC R'
source                 1..21
                       mol_type = other DNA
                       organism = synthetic construct
SEQUENCE: 38
taacttacag ttgcgcctga g                                              21

SEQ ID NO: 39          moltype = DNA   length = 24
FEATURE                Location/Qualifiers
misc_feature           1..24
                       note = KPC-FAM
source                 1..24
                       mol_type = other DNA
                       organism = synthetic construct
SEQUENCE: 39
atcggtgtgt acgcgatgga tacc                                           24

SEQ ID NO: 40          moltype = DNA   length = 19
FEATURE                Location/Qualifiers
misc_feature           1..19
                       note = VIM F'
source                 1..19
                       mol_type = other DNA
                       organism = synthetic construct
SEQUENCE: 40
cattcgaccg acaacttag                                                 19

SEQ ID NO: 41          moltype = DNA   length = 17
FEATURE                Location/Qualifiers
misc_feature           1..17
                       note = VIM R'
source                 1..17
                       mol_type = other DNA
                       organism = synthetic construct
SEQUENCE: 41
cgtgcgtgac aactcat                                                   17

SEQ ID NO: 42          moltype = DNA   length = 24
FEATURE                Location/Qualifiers
misc_feature           1..24
                       note = VIM-TEX
source                 1..24
                       mol_type = other DNA
                       organism = synthetic construct
SEQUENCE: 42
tgtgctctat ggtggttgtg cgat                                           24

SEQ ID NO: 43          moltype = DNA   length = 21
FEATURE                Location/Qualifiers
misc_feature           1..21
                       note = DHA F'
source                 1..21
                       mol_type = other DNA
                       organism = synthetic construct
```

-continued

```
SEQUENCE: 43
tgcgtacggt tatgagaaca a                                              21

SEQ ID NO: 44            moltype = DNA  length = 18
FEATURE                  Location/Qualifiers
misc_feature             1..18
                         note = DHA R'
source                   1..18
                         mol_type = other DNA
                         organism = synthetic construct
SEQUENCE: 44
cccagcgcag catatctt                                                  18

SEQ ID NO: 45            moltype = DNA  length = 24
FEATURE                  Location/Qualifiers
misc_feature             1..24
                         note = DHA-FAM
source                   1..24
                         mol_type = other DNA
                         organism = synthetic construct
SEQUENCE: 45
atgcggaatc ttacggcgtg aaat                                           24

SEQ ID NO: 46            moltype = DNA  length = 21
FEATURE                  Location/Qualifiers
misc_feature             1..21
                         note = IMP F'
source                   1..21
                         mol_type = other DNA
                         organism = synthetic construct
SEQUENCE: 46
acgtagtggt ttggttacct g                                              21

SEQ ID NO: 47            moltype = DNA  length = 22
FEATURE                  Location/Qualifiers
misc_feature             1..22
                         note = IMP R'
source                   1..22
                         mol_type = other DNA
                         organism = synthetic construct
SEQUENCE: 47
aagcttctaa atttgcgtca cc                                             22

SEQ ID NO: 48            moltype = DNA  length = 24
FEATURE                  Location/Qualifiers
misc_feature             1..24
                         note = IMP-TYE705
source                   1..24
                         mol_type = other DNA
                         organism = synthetic construct
SEQUENCE: 48
tttgttaaac cggacggtct tggt                                           24

SEQ ID NO: 49            moltype = DNA  length = 201
FEATURE                  Location/Qualifiers
misc_feature             1..201
                         note = MOX
source                   1..201
                         mol_type = other DNA
                         organism = synthetic construct
SEQUENCE: 49
aaccgggaga gcggggccag cgtcagcgag cagaccctgt tcgagatagg atccgtgagc    60
aagaccctga ctgcgaccct gggggcctat gcggtggtca agggagcgat gcagctggat   120
gacaaggcga gccggcacgc gccctggctc aagggatccg tctttgacag catcaccatg   180
ggggagcttg ccacctacag c                                             201

SEQ ID NO: 50            moltype = DNA  length = 240
FEATURE                  Location/Qualifiers
misc_feature             1..240
                         note = FOX
source                   1..240
                         mol_type = other DNA
                         organism = synthetic construct
SEQUENCE: 50
ggggatggcg gtcgccgtgc tgaaagatgg caaggcccac tatttcaact atggggttgc    60
caaccgcgag agtggtcagc gcgtcagcga gcagaccctg ttcgagattg gctcggtcag   120
caagaccctg accgcgaccc tcggtgccta tgctgcggtc aagggggct ttgagctgga   180
tgacaaggtg agccagcacg ccccctggct caaaggttcc gcctttgatg gtgtgaccat   240
```

| SEQ ID NO: 51 | moltype = DNA  length = 220 |
|---|---|
| FEATURE | Location/Qualifiers |
| misc_feature | 1..220 |
| | note = EBC |
| source | 1..220 |
| | mol_type = other DNA |
| | organism = synthetic construct |

SEQUENCE: 51
```
ggaccgttac gccgctgatg aaagcgcagg ccattccggg tatggcggtg gcggtgattt    60
atgagggtca gccgcactac ttcaccttcg gtaaagccga tgttgcggcg aacaaacctg   120
tcactccaca aaccttgttc gaactgggtt ctataagtaa aaccttcacc ggcgtactcg   180
gtggcgatgc cattgctcgc ggtgaaatat cgctgggcga                         220
```

| SEQ ID NO: 52 | moltype = DNA  length = 220 |
|---|---|
| FEATURE | Location/Qualifiers |
| misc_feature | 1..220 |
| | note = DHA |
| source | 1..220 |
| | mol_type = other DNA |
| | organism = synthetic construct |

SEQUENCE: 52
```
gactgcacgg atcctggcac cgctggggtt atctcacacc tttattactg tgccggaaag    60
tgcgcaaagc cagtatgcgt acggttatga gaacaaaaaa ccggtccgcg tgtcgccggg   120
acagcttgat gcggaatctt acggcgtgga atccgcctca aaagatatgc tgcgctgggc   180
ggaaatgaat atggagccgt cacgggccgg taatgcggat                         220
```

| SEQ ID NO: 53 | moltype = DNA  length = 260 |
|---|---|
| FEATURE | Location/Qualifiers |
| misc_feature | 1..260 |
| | note = CMY |
| source | 1..260 |
| | mol_type = other DNA |
| | organism = synthetic construct |

SEQUENCE: 53
```
gcctgtacac gtttctccgg gacaacttga cgccgaagcc tatggcgtga atccagcgt    60
tattgatatg gcccgctggg ttcaggtcaa catggacgcc agccgcgttc aggagaaaac   120
gctccagcag ggcattgcgc ttgcgcagtc tcgctactgg cgtattggcg atatgtacca   180
gggattaggc tgggagatgc tgaactggcc gctgaaagct gattcgatca tcaacggtag   240
cgacagcaaa gtggcattgg                                              260
```

| SEQ ID NO: 54 | moltype = DNA  length = 150 |
|---|---|
| FEATURE | Location/Qualifiers |
| misc_feature | 1..150 |
| | note = ACC |
| source | 1..150 |
| | mol_type = other DNA |
| | organism = synthetic construct |

SEQUENCE: 54
```
gagagcaaaa ttaaagacac cgttgatgac ctgatccagc cgctgatgca aagaataat    60
attcccggta tgtcggtcgc agtgaccgtc aacggtaaaa actacatttta taactatggg   120
ttagcggcaa aacagcctca gcagccggtt                                    150
```

| SEQ ID NO: 55 | moltype = DNA  length = 270 |
|---|---|
| FEATURE | Location/Qualifiers |
| misc_feature | 1..270 |
| | note = IC |
| source | 1..270 |
| | mol_type = other DNA |
| | organism = synthetic construct |

SEQUENCE: 55
```
agcttgttgg tggggtaacg gctcaccaag gcgacgatcc ctagctggtc tgagaggatg    60
accagccaca ctggaactga gacacggtcc agactcctac gggaggcagc agtggggaat   120
attgcacaat gggcgcaagc ctgatgcagc catgccgcgt gtatgaagaa ggccttcggg   180
ttgtaaagta ctttcagcgg ggaggaaggg agtaaagtta atacctttgc tcattgacgt   240
tacccgcaga agaagcaccg gctaactccg                                    270
```

| SEQ ID NO: 56 | moltype = DNA  length = 321 |
|---|---|
| FEATURE | Location/Qualifiers |
| misc_feature | 1..321 |
| | note = CTX-M-14 |
| source | 1..321 |
| | mol_type = other DNA |
| | organism = synthetic construct |

SEQUENCE: 56
```
cgtttcgtct ggatcgcact gaacctacgc tgaataccgc cattcccggc gacccgagag    60
acaccaccac gccgcgggcg atggcgcaga cgttgcgtca gcttacgctg gtcatgcgc   120
tgggcgaaac ccagcgggcg cagttggtga cgtggctcaa aggcaatacg accgcgcag   180
ccagcattcg gcgcggctta ccgacgtcgt ggactgtggg tgataagacc ggcagcgcg   240
actacggcac caccaatgat attgcggtga ctctggcgca gggtcgtgcg ccgctggttc   300
```

```
tggtgaccta ttttacccag c                                              321

SEQ ID NO: 57           moltype = DNA   length = 121
FEATURE                 Location/Qualifiers
misc_feature            1..121
                        note = CTX-M-15
source                  1..121
                        mol_type = other DNA
                        organism = synthetic construct
SEQUENCE: 57
ccgtcacgct gttgttagga agtgtgccgc tgtatgcgca aacggcggac gtacagcaaa    60
aacttgccga attagagcgg cagtcgggag gcagactggg tgtggcattg attaacacag   120
c                                                                   121

SEQ ID NO: 58           moltype = DNA   length = 553
FEATURE                 Location/Qualifiers
misc_feature            1..553
                        note = OXA
source                  1..553
                        mol_type = other DNA
                        organism = synthetic construct
SEQUENCE: 58
aatcacaggg cgtagttgtg ctctggaatg agaataagca gcaaggattt accaataatc    60
ttaaacgggc gaaccaagca ttttttacccg catctacctt taaaattccc aatagcttga   120
tcgccctcga tttgggcgtg gttaaggatg aacaccaagt ctttaagtgg gatggacaga   180
cgcgcgatat cgccacttgg aatcgcgatc ataatctaat caccgcgatg aatattcag   240
ttgtgcctgt ttatcaagaa tttgcccgcc aaattggcga ggcacgtatg agcaagatgc   300
tacatgcttt cgattatggt aatgaggaca tttcgggcaa tgtagacagt ttctggctcg   360
acggtggtat tcgaatttcg gccacggagc aaatcagctt tttaagaaag ctgtatcaca   420
ataagttaca cgtatcggag cgcagccagc gtattgtcaa acaagccatg ctgaccgaag   480
ccaatggtga ctaattattc gggctaaaac tggatactcg actagaatcg aacctaagat   540
tggctggctg ggt                                                      553

SEQ ID NO: 59           moltype = DNA   length = 270
FEATURE                 Location/Qualifiers
misc_feature            1..270
                        note = IC
source                  1..270
                        mol_type = other DNA
                        organism = synthetic construct
SEQUENCE: 59
cggagttagc cggtgcttct tctgcgggta acgtcaatga gcaaaggtat taactttact    60
cccttcctcc ccgctgaaag tactttacaa cccgaaggtc ttcttcatac acgcgtgtc   120
gctgcatcag gcttgcgccc attgtgcaat attcccccact gctgcctccc gtaggagtct   180
ggaccgtgtc tcagttccag tgtggctggt catcctctca gaccagctag ggatcgtcgc   240
cttggtgagc cgttaccccca ccaacaagct                                   270

SEQ ID NO: 60           moltype = DNA   length = 260
FEATURE                 Location/Qualifiers
misc_feature            1..260
                        note = CMY
source                  1..260
                        mol_type = other DNA
                        organism = synthetic construct
SEQUENCE: 60
gcctgtacac gtttctccgg gacaacttga cgccgaagcc tatggcgtga atccagcgt    60
tattgatatg gcccgctggg ttcaggtcaa catggacgcc agccgcgttc aggagaaaac   120
gctccagcag ggcattgcgc ttgcgcagtc tcgctactgg cgtattggcg atatgtacca   180
gggattaggc tgggagatgc tgaactggcc gctgaaagct gattcgatca tcaacggtag   240
cgacagcaaa gtggcattgg                                               260

SEQ ID NO: 61           moltype = DNA   length = 263
FEATURE                 Location/Qualifiers
misc_feature            1..263
                        note = NDM
source                  1..263
                        mol_type = other DNA
                        organism = synthetic construct
SEQUENCE: 61
ggcgaaagtc aggctgtgtt gcgccgcaac catcccctct tgcggggcaa gctggttcga    60
caacgcattg gcataagtcg caatccccgc cgcatgcagc gcgtccatac cgccatctt   120
gtcctgatgc gcgtgagtca ccaccgccag cgcgaccggc aggttgatct cctgcttgat   180
ccagttgagg atctgggcgg tctggtcatc ggtccaggcg gtatcgacca ccagcacgcg   240
gccgccatcc ctgacgatca aac                                           263

SEQ ID NO: 62           moltype = DNA   length = 209
FEATURE                 Location/Qualifiers
misc_feature            1..209
                        note = KPC
```

```
source                  1..209
                        mol_type = other DNA
                        organism = synthetic construct
SEQUENCE: 62
gtatcgccgt ctagttctgc tgtcttgtct ctcatggccg ctggctggct tttctgccac    60
cgcgctgacc aacctcgtcg cggaaccatt cgctaaactc gaacaggact ttggcggctc   120
catcggtgtg tacgcgatgg ataccggctc aggcgcaact gtaagttacc gcgctgagga   180
gcgcttccca ctgtgcagct cattcaagg                                     209

SEQ ID NO: 63           moltype = DNA  length = 292
FEATURE                 Location/Qualifiers
misc_feature            1..292
                        note = VIM
source                  1..292
                        mol_type = other DNA
                        organism = synthetic construct
SEQUENCE: 63
ccattcagcc agatcggcat cggccacgtt ccccgcagac gtgcgtgaca actcatgaat    60
cgcacaacca ccatagagca cactcgcaga cgggacgtac acaactaagt tgtcggtcga   120
atgcgcagca ccaggataga agagttctac tggaccgaag cgcactgcgt ccccgctcga   180
gtccttctag agagtgcgtg ggaatctcgt tcccctctac ctcggctagc cggcgtgtcg   240
acggtgatgc gtacgttgcc accccagccg cccgaaggac atcaacgccg cc           292

SEQ ID NO: 64           moltype = DNA  length = 220
FEATURE                 Location/Qualifiers
misc_feature            1..220
                        note = DHA
source                  1..220
                        mol_type = other DNA
                        organism = synthetic construct
SEQUENCE: 64
gactgcacgg atcctggcac cgctggggtt atctcacacc tttattactg tgccggaaag    60
tgcgcaaagc cagtatgcgt acggttatga gaacaaaaaa ccggtccgcg tgtcgccggg   120
acagcttgat gcgcgaatctt acggcgtgaa atccgcctca aaagatatgc tgcgctgggc   180
ggaaatgaat atggagccgt cacgggccgg taatgcggat                          220

SEQ ID NO: 65           moltype = DNA  length = 270
FEATURE                 Location/Qualifiers
misc_feature            1..270
                        note = IC
source                  1..270
                        mol_type = other DNA
                        organism = synthetic construct
SEQUENCE: 65
cggagttagc cggtgcttct tctgcgggta acgtcaatga gcaaaggtat taactttact    60
ccccttcctcc ccgctgaaag tactttacaa cccgaaggcc ttcttcatac acgcggcatg   120
gctgcatcag gcttgcgccc attgtgcaat attcccccact gctgcctccc gtaggagtct   180
ggaccgtgtc tcagttccag tgtggctggt catcctctca gaccagctag ggatcgtcgc   240
cttggtgagc cgttaccccca ccaacaagct                                    270

SEQ ID NO: 66           moltype = DNA  length = 177
FEATURE                 Location/Qualifiers
misc_feature            1..177
                        note = IMP
source                  1..177
                        mol_type = other DNA
                        organism = synthetic construct
SEQUENCE: 66
gcggagttag ttattggcta gttaaaaata aaattgaagt ttttttatccc ggcccggggc    60
acactcaaga taacgtagtg gtttggttac ctgaaaagaa aattttattc ggtggttgtt   120
ttgttaaacc ggacggtctt grvgtaattt gggtgacgca aatttagaag cttggcc       177

SEQ ID NO: 67           moltype = DNA  length = 21
FEATURE                 Location/Qualifiers
misc_feature            1..21
                        note = PRIMER/PROBE
source                  1..21
                        mol_type = other DNA
                        organism = synthetic construct
SEQUENCE: 67
tggccagaac tgacaggcaa a                                              21

SEQ ID NO: 68           moltype = DNA  length = 21
FEATURE                 Location/Qualifiers
misc_feature            1..21
                        note = PRIMER/PROBE
source                  1..21
                        mol_type = other DNA
                        organism = synthetic construct
```

```
SEQUENCE: 68
tttctcctga acgtggctgg c                                              21

SEQ ID NO: 69          moltype = DNA  length = 24
FEATURE                Location/Qualifiers
misc_feature           1..24
                       note = PRIMER/PROBE
source                 1..24
                       mol_type = other DNA
                       organism = synthetic construct
SEQUENCE: 69
acgctaactc cagcattggt ctgt                                           24

SEQ ID NO: 70          moltype = DNA  length = 19
FEATURE                Location/Qualifiers
misc_feature           1..19
                       note = PRIMER/PROBE
source                 1..19
                       mol_type = other DNA
                       organism = synthetic construct
SEQUENCE: 70
ccgtcacgct gttgttagg                                                 19

SEQ ID NO: 71          moltype = DNA  length = 22
FEATURE                Location/Qualifiers
misc_feature           1..22
                       note = PRIMER/PROBE
source                 1..22
                       mol_type = other DNA
                       organism = synthetic construct
SEQUENCE: 71
gctgtgttaa tcaatgccac ac                                             22

SEQ ID NO: 72          moltype = DNA  length = 24
FEATURE                Location/Qualifiers
misc_feature           1..24
                       note = PRIMER/PROBE
source                 1..24
                       mol_type = other DNA
                       organism = synthetic construct
SEQUENCE: 72
aacttgccga attagagcrg cagt                                           24

SEQ ID NO: 73          moltype = DNA  length = 19
FEATURE                Location/Qualifiers
misc_feature           1..19
                       note = PRIMER/PROBE
source                 1..19
                       mol_type = other DNA
                       organism = synthetic construct
SEQUENCE: 73
cgtttcgtct ggatcgcac                                                 19

SEQ ID NO: 74          moltype = DNA  length = 20
FEATURE                Location/Qualifiers
misc_feature           1..20
                       note = PRIMER/PROBE
source                 1..20
                       mol_type = other DNA
                       organism = synthetic construct
SEQUENCE: 74
gctgggtaaa ataggtcacc                                                20

SEQ ID NO: 75          moltype = DNA  length = 24
FEATURE                Location/Qualifiers
misc_feature           1..24
                       note = PRIMER/PROBE
source                 1..24
                       mol_type = other DNA
                       organism = synthetic construct
SEQUENCE: 75
tatcattggt ggtgccgtag tcgc                                           24

SEQ ID NO: 76          moltype = DNA  length = 20
FEATURE                Location/Qualifiers
misc_feature           1..20
                       note = PRIMER/PROBE
source                 1..20
                       mol_type = other DNA
```

```
                        organism = synthetic construct
SEQUENCE: 76
gagaggatga ycagccacac                                           20

SEQ ID NO: 77           moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 77
cgcccattgt scaatattcc                                           20

SEQ ID NO: 78           moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 78
tgagacacgg tccagactcc tacg                                      24

SEQ ID NO: 79           moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 79
aatcacaggg cgtagttgtg                                           20

SEQ ID NO: 80           moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 80
acccaccagc caatcttagg                                           20

SEQ ID NO: 81           moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 81
tagcttgatc gccctcgatt tggg                                      24

SEQ ID NO: 82           moltype = DNA   length = 21
FEATURE                 Location/Qualifiers
misc_feature            1..21
                        note = PRIMER/PROBE
source                  1..21
                        mol_type = other DNA
                        organism = synthetic construct
SEQUENCE: 82
gcggagttaa ctattggcta g                                         21

SEQ ID NO: 83           moltype = DNA   length = 21
FEATURE                 Location/Qualifiers
misc_feature            1..21
                        note = PRIMER/PROBE
source                  1..21
                        mol_type = other DNA
                        organism = synthetic construct
SEQUENCE: 83
ggccaagctt ctatatttgc g                                         21

SEQ ID NO: 84           moltype = DNA   length = 23
FEATURE                 Location/Qualifiers
misc_feature            1..23
                        note = PRIMER/PROBE
source                  1..23
```

```
                            mol_type = other DNA
                            organism = synthetic construct
SEQUENCE: 84
ttrtttyggtg gttgytttrt taa                                          23

SEQ ID NO: 85               moltype = DNA  length = 21
FEATURE                     Location/Qualifiers
misc_feature                1..21
                            note = PRIMER/PROBE
source                      1..21
                            mol_type = other DNA
                            organism = synthetic construct
SEQUENCE: 85
gcggagttar ytattggcta g                                             21

SEQ ID NO: 86               moltype = DNA  length = 21
FEATURE                     Location/Qualifiers
misc_feature                1..21
                            note = PRIMER/PROBE
source                      1..21
                            mol_type = other DNA
                            organism = synthetic construct
SEQUENCE: 86
ggccaagcyt ctawatttgc g                                             21

SEQ ID NO: 87               moltype = DNA  length = 24
FEATURE                     Location/Qualifiers
misc_feature                1..24
                            note = PRIMER/PROBE
source                      1..24
                            mol_type = other DNA
                            organism = synthetic construct
SEQUENCE: 87
ccggacggtc ttggtaattt gggt                                          24

SEQ ID NO: 88               moltype = DNA  length = 24
FEATURE                     Location/Qualifiers
misc_feature                1..24
                            note = PRIMER/PROBE
source                      1..24
                            mol_type = other DNA
                            organism = synthetic construct
SEQUENCE: 88
ccgtacggtt taggcaattt gggt                                          24

SEQ ID NO: 89               moltype = DNA  length = 20
FEATURE                     Location/Qualifiers
misc_feature                1..20
                            note = PRIMER/PROBE
source                      1..20
                            mol_type = other DNA
                            organism = synthetic construct
SEQUENCE: 89
ggcggcgttg atgtccttcg                                               20

SEQ ID NO: 90               moltype = DNA  length = 21
FEATURE                     Location/Qualifiers
misc_feature                1..21
                            note = PRIMER/PROBE
source                      1..21
                            mol_type = other DNA
                            organism = synthetic construct
SEQUENCE: 90
ccattcagcc agatcggcat c                                             21

SEQ ID NO: 91               moltype = DNA  length = 23
FEATURE                     Location/Qualifiers
misc_feature                1..23
                            note = PRIMER/PROBE
source                      1..23
                            mol_type = other DNA
                            organism = synthetic construct
SEQUENCE: 91
agctcttcta tcctggtgct gcg                                           23

SEQ ID NO: 92               moltype = DNA  length = 22
FEATURE                     Location/Qualifiers
misc_feature                1..22
                            note = PRIMER/PROBE
```

```
source                          1..22
                                mol_type = other DNA
                                organism = synthetic construct
SEQUENCE: 92
aactttcaca ggtgtgctgg gt                                                22

SEQ ID NO: 93                   moltype = DNA  length = 21
FEATURE                         Location/Qualifiers
misc_feature                    1..21
                                note = PRIMER/PROBE
source                          1..21
                                mol_type = other DNA
                                organism = synthetic construct
SEQUENCE: 93
ccgtacgcat actggctttg c                                                 21

SEQ ID NO: 94                   moltype = DNA  length = 24
FEATURE                         Location/Qualifiers
misc_feature                    1..24
                                note = PRIMER/PROBE
source                          1..24
                                mol_type = other DNA
                                organism = synthetic construct
SEQUENCE: 94
aaaccgggcg atatgcgtct gtat                                              24

SEQ ID NO: 95                   moltype = DNA  length = 20
FEATURE                         Location/Qualifiers
misc_feature                    1..20
                                note = PRIMER/PROBE
source                          1..20
                                mol_type = other DNA
                                organism = synthetic construct
SEQUENCE: 95
gtatcgccgt ctagttctgc                                                   20

SEQ ID NO: 96                   moltype = DNA  length = 22
FEATURE                         Location/Qualifiers
misc_feature                    1..22
                                note = PRIMER/PROBE
source                          1..22
                                mol_type = other DNA
                                organism = synthetic construct
SEQUENCE: 96
ccttgaatga gctgcacagt gg                                                22

SEQ ID NO: 97                   moltype = DNA  length = 23
FEATURE                         Location/Qualifiers
misc_feature                    1..23
                                note = PRIMER/PROBE
source                          1..23
                                mol_type = other DNA
                                organism = synthetic construct
SEQUENCE: 97
tcgtcgcgga accattcgct aaa                                               23

SEQ ID NO: 98                   moltype = DNA  length = 20
FEATURE                         Location/Qualifiers
misc_feature                    1..20
                                note = PRIMER/PROBE
source                          1..20
                                mol_type = other DNA
                                organism = synthetic construct
SEQUENCE: 98
gtttgatcgt cagggatggc                                                   20

SEQ ID NO: 99                   moltype = DNA  length = 18
FEATURE                         Location/Qualifiers
misc_feature                    1..18
                                note = PRIMER/PROBE
source                          1..18
                                mol_type = other DNA
                                organism = synthetic construct
SEQUENCE: 99
ggcgaaagtc aggctgtg                                                     18

SEQ ID NO: 100                  moltype = DNA  length = 24
FEATURE                         Location/Qualifiers
misc_feature                    1..24
```

```
                    note = PRIMER/PROBE
source              1..24
                    mol_type = other DNA
                    organism = synthetic construct
SEQUENCE: 100
catcaggaca agatgggcgg tatg                                              24

SEQ ID NO: 101      moltype = DNA   length = 21
FEATURE             Location/Qualifiers
misc_feature        1..21
                    note = PRIMER/PROBE
source              1..21
                    mol_type = other DNA
                    organism = synthetic construct
SEQUENCE: 101
gctgctcaag gagcacagga t                                                 21

SEQ ID NO: 102      moltype = DNA   length = 22
FEATURE             Location/Qualifiers
misc_feature        1..22
                    note = PRIMER/PROBE
source              1..22
                    mol_type = other DNA
                    organism = synthetic construct
SEQUENCE: 102
cacattgaca taggtgtggt gc                                                22

SEQ ID NO: 103      moltype = DNA   length = 24
FEATURE             Location/Qualifiers
misc_feature        1..24
                    note = PRIMER/PROBE
source              1..24
                    mol_type = other DNA
                    organism = synthetic construct
SEQUENCE: 103
aggatggcaa ggcccactat ttca                                              24

SEQ ID NO: 104      moltype = DNA   length = 21
FEATURE             Location/Qualifiers
misc_feature        1..21
                    note = PRIMER/PROBES
source              1..21
                    mol_type = other DNA
                    organism = synthetic construct
SEQUENCE: 104
aacagcctca gcagccggtt a                                                 21

SEQ ID NO: 105      moltype = DNA   length = 21
FEATURE             Location/Qualifiers
misc_feature        1..21
                    note = PRIMER/PROBE
source              1..21
                    mol_type = other DNA
                    organism = synthetic construct
SEQUENCE: 105
ttcgccgcaa tcatccctag c                                                 21

SEQ ID NO: 106      moltype = DNA   length = 24
FEATURE             Location/Qualifiers
misc_feature        1..24
                    note = PRIMER/PROBE
source              1..24
                    mol_type = other DNA
                    organism = synthetic construct
SEQUENCE: 106
agccattacg ttccagagtt gcgt                                              24

SEQ ID NO: 107      moltype = DNA   length = 21
FEATURE             Location/Qualifiers
misc_feature        1..21
                    note = PRIMER/PROBE
source              1..21
                    mol_type = other DNA
                    organism = synthetic construct
SEQUENCE: 107
gccgaggctt acgggatcaa g                                                 21

SEQ ID NO: 108      moltype = DNA   length = 21
FEATURE             Location/Qualifiers
```

```
misc_feature              1..21
                          note = PRIMER/PROBE
source                    1..21
                          mol_type = other DNA
                          organism = synthetic construct
SEQUENCE: 108
caaagcgcgt aaccggattg g                                              21

SEQ ID NO: 109            moltype = DNA  length = 24
FEATURE                   Location/Qualifiers
misc_feature              1..24
                          note = PRIMER/PROBE
source                    1..24
                          mol_type = other DNA
                          organism = synthetic construct
SEQUENCE: 109
tctgctgaag tttrycgagg cmaa                                           24

SEQ ID NO: 110            moltype = DNA  length = 22
FEATURE                   Location/Qualifiers
misc_feature              1..22
                          note = PRIMER/PROBE
source                    1..22
                          mol_type = other DNA
                          organism = synthetic construct
SEQUENCE: 110
aactttcaca ggtgtgctgg gt                                             22

SEQ ID NO: 111            moltype = DNA  length = 21
FEATURE                   Location/Qualifiers
misc_feature              1..21
                          note = PRIMER/PROBE
source                    1..21
                          mol_type = other DNA
                          organism = synthetic construct
SEQUENCE: 111
ccgtacgcat actggctttg c                                              21

SEQ ID NO: 112            moltype = DNA  length = 24
FEATURE                   Location/Qualifiers
misc_feature              1..24
                          note = PRIMER/PROBE
source                    1..24
                          mol_type = other DNA
                          organism = synthetic construct
SEQUENCE: 112
aaaccgggcg atatgcgtct gtat                                           24

SEQ ID NO: 113            moltype = DNA  length = 29
FEATURE                   Location/Qualifiers
misc_feature              1..29
                          note = PRIMER/PROBE
source                    1..29
                          mol_type = other DNA
                          organism = synthetic construct
SEQUENCE: 113
ctgggttcta taagtaaaac cttcaccgg                                      29

SEQ ID NO: 114            moltype = DNA  length = 21
FEATURE                   Location/Qualifiers
misc_feature              1..21
                          note = PRIMER/PROBE
source                    1..21
                          mol_type = other DNA
                          organism = synthetic construct
SEQUENCE: 114
cttccactgc ggctgccagt t                                              21

SEQ ID NO: 115            moltype = DNA  length = 23
FEATURE                   Location/Qualifiers
misc_feature              1..23
                          note = PRIMER/PROBE
source                    1..23
                          mol_type = other DNA
                          organism = synthetic construct
SEQUENCE: 115
gatgccattg cycgsggtga aat                                            23

SEQ ID NO: 116            moltype = DNA  length = 23
```

```
FEATURE                 Location/Qualifiers
misc_feature            1..23
                        note = PRIMER/PROBE
source                  1..23
                        mol_type = other DNA
                        organism = synthetic construct
SEQUENCE: 116
ccgaagccta tggcgtgaaa tcc                                         23

SEQ ID NO: 117          moltype = DNA   length = 19
FEATURE                 Location/Qualifiers
misc_feature            1..19
                        note = PRIMER/PROBE
source                  1..19
                        mol_type = other DNA
                        organism = synthetic construct
SEQUENCE: 117
gcaatgccct gctggagcg                                              19

SEQ ID NO: 118          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 118
atgttggcct gaacccagcg                                             20

SEQ ID NO: 119          moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 119
agcacataca gaatatgtcc ctgc                                        24

SEQ ID NO: 120          moltype = DNA   length = 25
FEATURE                 Location/Qualifiers
misc_feature            1..25
                        note = PRIMER/PROBE
source                  1..25
                        mol_type = other DNA
                        organism = synthetic construct
SEQUENCE: 120
acctgttaac caacctactt gaggg                                       25

SEQ ID NO: 121          moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 121
ttgcaagacg gactggctta gacc                                        24

SEQ ID NO: 122          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 122
cctgatcgga ttggagaacc                                             20

SEQ ID NO: 123          moltype = DNA   length = 23
FEATURE                 Location/Qualifiers
misc_feature            1..23
                        note = PRIMER/PROBE
source                  1..23
                        mol_type = other DNA
                        organism = synthetic construct
SEQUENCE: 123
ctacctcttg aataggcgta acc                                         23
```

```
SEQ ID NO: 124            moltype = DNA   length = 24
FEATURE                   Location/Qualifiers
misc_feature              1..24
                          note = PRIMER/PROBE
source                    1..24
                          mol_type = other DNA
                          organism = synthetic construct
SEQUENCE: 124
acgtcgcgca agttcctgat agac                                          24

SEQ ID NO: 125            moltype = DNA   length = 25
FEATURE                   Location/Qualifiers
misc_feature              1..25
                          note = PRIMER/PROBE
source                    1..25
                          mol_type = other DNA
                          organism = synthetic construct
SEQUENCE: 125
tagtgactgc taatccaaat cacag                                         25

SEQ ID NO: 126            moltype = DNA   length = 25
FEATURE                   Location/Qualifiers
misc_feature              1..25
                          note = PRIMER/PROBE
source                    1..25
                          mol_type = other DNA
                          organism = synthetic construct
SEQUENCE: 126
gcacgagcaa gatcattacc atagc                                         25

SEQ ID NO: 127            moltype = DNA   length = 27
FEATURE                   Location/Qualifiers
misc_feature              1..27
                          note = PRIMER/PROBE
source                    1..27
                          mol_type = other DNA
                          organism = synthetic construct
SEQUENCE: 127
agttatccaa caaggccaaa ctcaaca                                       27

SEQ ID NO: 128            moltype = DNA   length = 20
FEATURE                   Location/Qualifiers
misc_feature              1..20
                          note = PRIMER/PROBE
source                    1..20
                          mol_type = other DNA
                          organism = synthetic construct
SEQUENCE: 128
aatcacaggg cgtagttgtg                                               20

SEQ ID NO: 129            moltype = DNA   length = 20
FEATURE                   Location/Qualifiers
misc_feature              1..20
                          note = PRIMER/PROBE
source                    1..20
                          mol_type = other DNA
                          organism = synthetic construct
SEQUENCE: 129
acccaccagc caatcttagg                                               20

SEQ ID NO: 130            moltype = DNA   length = 24
FEATURE                   Location/Qualifiers
misc_feature              1..24
                          note = PRIMER/PROBE
source                    1..24
                          mol_type = other DNA
                          organism = synthetic construct
SEQUENCE: 130
tagcttgatc gccctcgatt tggg                                          24

SEQ ID NO: 131            moltype = DNA   length = 18
FEATURE                   Location/Qualifiers
misc_feature              1..18
                          note = PRIMER/PROBE
source                    1..18
                          mol_type = other DNA
                          organism = synthetic construct
SEQUENCE: 131
gtgggatgga aagccacg                                                 18
```

```
SEQ ID NO: 132          moltype = DNA   length = 18
FEATURE                 Location/Qualifiers
misc_feature            1..18
                        note = PRIMER/PROBE
source                  1..18
                        mol_type = other DNA
                        organism = synthetic construct
SEQUENCE: 132
cacttgcggg tctacagc                                                     18

SEQ ID NO: 133          moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 133
ttactttggg cgaagccatg caag                                              24

SEQ ID NO: 134          moltype = DNA   length = 21
FEATURE                 Location/Qualifiers
misc_feature            1..21
                        note = PRIMER/PROBE
source                  1..21
                        mol_type = other DNA
                        organism = synthetic construct
SEQUENCE: 134
cacctatggt aatgctcttg c                                                 21

SEQ ID NO: 135          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 135
ctggaactgc tgacaatgcc                                                   20

SEQ ID NO: 136          moltype = DNA   length = 30
FEATURE                 Location/Qualifiers
misc_feature            1..30
                        note = PRIMER/PROBE
source                  1..30
                        mol_type = other DNA
                        organism = synthetic construct
SEQUENCE: 136
tgggagaaag atatgacttt aggtgaggca                                        30

SEQ ID NO: 137          moltype = DNA   length = 18
FEATURE                 Location/Qualifiers
misc_feature            1..18
                        note = PRIMER/PROBES
source                  1..18
                        mol_type = other DNA
                        organism = synthetic construct
SEQUENCE: 137
ccgtgtatgt tcagctat                                                     18

SEQ ID NO: 138          moltype = DNA   length = 18
FEATURE                 Location/Qualifiers
misc_feature            1..18
                        note = PRIMER/PROBE
source                  1..18
                        mol_type = other DNA
                        organism = synthetic construct
SEQUENCE: 138
cttatccatc acgccttt                                                     18

SEQ ID NO: 139          moltype = DNA   length = 26
FEATURE                 Location/Qualifiers
misc_feature            1..26
                        note = PRIMER/PROBES
source                  1..26
                        mol_type = other DNA
                        organism = synthetic construct
SEQUENCE: 139
```

```
tatgatgtcg ataccgccaa atacca                                            26

SEQ ID NO: 140         moltype = DNA   length = 18
FEATURE                Location/Qualifiers
misc_feature           1..18
                       note = PRIMER/PROBE
source                 1..18
                       mol_type = other DNA
                       organism = synthetic construct
SEQUENCE: 140
ctgtatgtca gcgatcat                                                     18

SEQ ID NO: 141         moltype = DNA   length = 19
FEATURE                Location/Qualifiers
misc_feature           1..19
                       note = PRIMER/PROBE
source                 1..19
                       mol_type = other DNA
                       organism = synthetic construct
SEQUENCE: 141
gatgccagtt tgcttatcc                                                    19

SEQ ID NO: 142         moltype = DNA   length = 25
FEATURE                Location/Qualifiers
misc_feature           1..25
                       note = PRIMER/PROBE
source                 1..25
                       mol_type = other DNA
                       organism = synthetic construct
SEQUENCE: 142
aagtctgggt gagaacggtg tctat                                             25

SEQ ID NO: 143         moltype = DNA   length = 19
FEATURE                Location/Qualifiers
misc_feature           1..19
                       note = PRIMER/PROBE
source                 1..19
                       mol_type = other DNA
                       organism = synthetic construct
SEQUENCE: 143
cagtcagtat gcgagtttc                                                    19

SEQ ID NO: 144         moltype = DNA   length = 18
FEATURE                Location/Qualifiers
misc_feature           1..18
                       note = PRIMER/PROBE
source                 1..18
                       mol_type = other DNA
                       organism = synthetic construct
SEQUENCE: 144
aaaattcgcc aagccatc                                                     18

SEQ ID NO: 145         moltype = DNA   length = 25
FEATURE                Location/Qualifiers
misc_feature           1..25
                       note = PRIMER/PROBE
source                 1..25
                       mol_type = other DNA
                       organism = synthetic construct
SEQUENCE: 145
tgcataagcc agtgcgtttt tatat                                             25

SEQ ID NO: 146         moltype = DNA   length = 18
FEATURE                Location/Qualifiers
misc_feature           1..18
                       note = PRIMER/PROBE
source                 1..18
                       mol_type = other DNA
                       organism = synthetic construct
SEQUENCE: 146
agatcagttg ggtgcacg                                                     18

SEQ ID NO: 147         moltype = DNA   length = 20
FEATURE                Location/Qualifiers
misc_feature           1..20
                       note = PRIMER/PROBE
source                 1..20
                       mol_type = other DNA
                       organism = synthetic construct
```

```
SEQUENCE: 147
tgcttaatca gtgaggcacc                                                    20

SEQ ID NO: 148        moltype = DNA  length = 24
FEATURE               Location/Qualifiers
misc_feature          1..24
                      note = PRIMER/PROBE
source                1..24
                      mol_type = other DNA
                      organism = synthetic construct
SEQUENCE: 148
atgaagccat accaaacgac gagc                                               24

SEQ ID NO: 149        moltype = DNA  length = 20
FEATURE               Location/Qualifiers
misc_feature          1..20
                      note = PRIMER/PROBE
source                1..20
                      mol_type = other DNA
                      organism = synthetic construct
SEQUENCE: 149
ctggagcgaa agatccacta                                                    20

SEQ ID NO: 150        moltype = DNA  length = 18
FEATURE               Location/Qualifiers
misc_feature          1..18
                      note = PRIMER/PROBE
source                1..18
                      mol_type = other DNA
                      organism = synthetic construct
SEQUENCE: 150
atcgtccacc atccactg                                                      18

SEQ ID NO: 151        moltype = DNA  length = 22
FEATURE               Location/Qualifiers
misc_feature          1..22
                      note = PRIMER/PROBE
source                1..22
                      mol_type = other DNA
                      organism = synthetic construct
SEQUENCE: 151
ccagatcggc gacaacgtca cc                                                 22

SEQ ID NO: 152        moltype = DNA  length = 21
FEATURE               Location/Qualifiers
misc_feature          1..21
                      note = PRIMER/PROBE
source                1..21
                      mol_type = other DNA
                      organism = synthetic construct
SEQUENCE: 152
tggccagaac tgacaggcaa a                                                  21

SEQ ID NO: 153        moltype = DNA  length = 21
FEATURE               Location/Qualifiers
misc_feature          1..21
                      note = PRIMER/PROBE
source                1..21
                      mol_type = other DNA
                      organism = synthetic construct
SEQUENCE: 153
tttctcctga acgtggctgg c                                                  21

SEQ ID NO: 154        moltype = DNA  length = 24
FEATURE               Location/Qualifiers
misc_feature          1..24
                      note = PRIMER/PROBE
source                1..24
                      mol_type = other DNA
                      organism = synthetic construct
SEQUENCE: 154
acgctaactc cagcattggt ctgt                                               24

SEQ ID NO: 155        moltype = DNA  length = 19
FEATURE               Location/Qualifiers
misc_feature          1..19
                      note = PRIMER/PROBE
source                1..19
                      mol_type = other DNA
```

```
                                    organism = synthetic construct
SEQUENCE: 155
ccgtcacgct gttgttagg                                                           19

SEQ ID NO: 156          moltype = DNA   length = 22
FEATURE                 Location/Qualifiers
misc_feature            1..22
                        note = PRIMER/PROBE
source                  1..22
                        mol_type = other DNA
                        organism = synthetic construct
SEQUENCE: 156
gctgtgttaa tcaatgccac ac                                                       22

SEQ ID NO: 157          moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 157
aacttgccga attagagcrg cagt                                                     24

SEQ ID NO: 158          moltype = DNA   length = 19
FEATURE                 Location/Qualifiers
misc_feature            1..19
                        note = PRIMER/PROBE
source                  1..19
                        mol_type = other DNA
                        organism = synthetic construct
SEQUENCE: 158
cgtttcgtct ggatcgcac                                                           19

SEQ ID NO: 159          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 159
gctgggtaaa ataggtcacc                                                          20

SEQ ID NO: 160          moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 160
tatcattggt ggtgccgtag tcgc                                                     24

SEQ ID NO: 161          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 161
gagaggatga ycagccacac                                                          20

SEQ ID NO: 162          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 162
cgcccattgt scaatattcc                                                          20

SEQ ID NO: 163          moltype = DNA   length = 24
FEATURE                 Location/Qualifiers
misc_feature            1..24
                        note = PRIMER/PROBE
source                  1..24
```

```
                        mol_type = other DNA
                        organism = synthetic construct
SEQUENCE: 163
tgagacacgg tccagactcc tacg                                              24

SEQ ID NO: 164          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 164
aatcacaggg cgtagttgtg                                                   20

SEQ ID NO: 165          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 165
acccaccagc caatcttagg                                                   20

SEQ ID NO: 166          moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 166
tagcttgatc gccctcgatt tggg                                              24

SEQ ID NO: 167          moltype = DNA   length = 21
FEATURE                 Location/Qualifiers
misc_feature            1..21
                        note = PRIMER/PROBE
source                  1..21
                        mol_type = other DNA
                        organism = synthetic construct
SEQUENCE: 167
gcggagttaa ctattggcta g                                                 21

SEQ ID NO: 168          moltype = DNA   length = 21
FEATURE                 Location/Qualifiers
misc_feature            1..21
                        note = PRIMER/PROBE
source                  1..21
                        mol_type = other DNA
                        organism = synthetic construct
SEQUENCE: 168
ggccaagctt ctatatttgc g                                                 21

SEQ ID NO: 169          moltype = DNA   length = 23
FEATURE                 Location/Qualifiers
misc_feature            1..23
                        note = PRIMER/PROBE
source                  1..23
                        mol_type = other DNA
                        organism = synthetic construct
SEQUENCE: 169
ttrttyggtg gttgytttrt taa                                               23

SEQ ID NO: 170          moltype = DNA   length = 21
FEATURE                 Location/Qualifiers
misc_feature            1..21
                        note = PRIMER/PROBE
source                  1..21
                        mol_type = other DNA
                        organism = synthetic construct
SEQUENCE: 170
gcggagttar ytattggcta g                                                 21

SEQ ID NO: 171          moltype = DNA   length = 21
FEATURE                 Location/Qualifiers
misc_feature            1..21
                        note = PRIMER/PROBE
```

```
source                     1..21
                           mol_type = other DNA
                           organism = synthetic construct
SEQUENCE: 171
ggccaagcyt ctawatttgc g                                              21

SEQ ID NO: 172             moltype = DNA   length = 24
FEATURE                    Location/Qualifiers
misc_feature               1..24
                           note = PRIMER/PROBE
source                     1..24
                           mol_type = other DNA
                           organism = synthetic construct
SEQUENCE: 172
ccggacggtc ttggtaattt gggt                                           24

SEQ ID NO: 173             moltype = DNA   length = 24
FEATURE                    Location/Qualifiers
misc_feature               1..24
                           note = PRIMER/PROBE
source                     1..24
                           mol_type = other DNA
                           organism = synthetic construct
SEQUENCE: 173
ccgtacggtt taggcaattt gggt                                           24

SEQ ID NO: 174             moltype = DNA   length = 20
FEATURE                    Location/Qualifiers
misc_feature               1..20
                           note = PRIMER/PROBE
source                     1..20
                           mol_type = other DNA
                           organism = synthetic construct
SEQUENCE: 174
ggcggcgttg atgtccttcg                                                20

SEQ ID NO: 175             moltype = DNA   length = 21
FEATURE                    Location/Qualifiers
misc_feature               1..21
                           note = PRIMER/PROBE
source                     1..21
                           mol_type = other DNA
                           organism = synthetic construct
SEQUENCE: 175
ccattcagcc agatcggcat c                                              21

SEQ ID NO: 176             moltype = DNA   length = 23
FEATURE                    Location/Qualifiers
misc_feature               1..23
                           note = PRIMER/PROBE
source                     1..23
                           mol_type = other DNA
                           organism = synthetic construct
SEQUENCE: 176
agctcttcta tcctggtgct gcg                                            23

SEQ ID NO: 177             moltype = DNA   length = 20
FEATURE                    Location/Qualifiers
misc_feature               1..20
                           note = PRIMER/PROBE
source                     1..20
                           mol_type = other DNA
                           organism = synthetic construct
SEQUENCE: 177
gagaggatga ycagccacac                                                20

SEQ ID NO: 178             moltype = DNA   length = 20
FEATURE                    Location/Qualifiers
misc_feature               1..20
                           note = PRIMER/PROBE
source                     1..20
                           mol_type = other DNA
                           organism = synthetic construct
SEQUENCE: 178
cgcccattgt scaatattcc                                                20

SEQ ID NO: 179             moltype = DNA   length = 24
FEATURE                    Location/Qualifiers
misc_feature               1..24
```

```
                        note = PRIMER/PROBE
source                  1..24
                        mol_type = other DNA
                        organism = synthetic construct
SEQUENCE: 179
tgagacacgg tccagactcc tacg                                           24

SEQ ID NO: 180          moltype = DNA   length = 22
FEATURE                 Location/Qualifiers
misc_feature            1..22
                        note = PRIMER/PROBE
source                  1..22
                        mol_type = other DNA
                        organism = synthetic construct
SEQUENCE: 180
aactttcaca ggtgtgctgg gt                                             22

SEQ ID NO: 181          moltype = DNA   length = 21
FEATURE                 Location/Qualifiers
misc_feature            1..21
                        note = PRIMER/PROBE
source                  1..21
                        mol_type = other DNA
                        organism = synthetic construct
SEQUENCE: 181
ccgtacgcat actggctttg c                                              21

SEQ ID NO: 182          moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 182
aaaccgggcg atatgcgtct gtat                                           24

SEQ ID NO: 183          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 183
gtatcgccgt ctagttctgc                                                20

SEQ ID NO: 184          moltype = DNA   length = 22
FEATURE                 Location/Qualifiers
misc_feature            1..22
                        note = PRIMER/PROBE
source                  1..22
                        mol_type = other DNA
                        organism = synthetic construct
SEQUENCE: 184
ccttgaatga gctgcacagt gg                                             22

SEQ ID NO: 185          moltype = DNA   length = 23
FEATURE                 Location/Qualifiers
misc_feature            1..23
                        note = PRIMER/PROBE
source                  1..23
                        mol_type = other DNA
                        organism = synthetic construct
SEQUENCE: 185
tcgtcgcgga accattcgct aaa                                            23

SEQ ID NO: 186          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 186
gtttgatcgt cagggatggc                                                20

SEQ ID NO: 187          moltype = DNA   length = 18
FEATURE                 Location/Qualifiers
```

```
misc_feature              1..18
                          note = PRIMER/PROBE
source                    1..18
                          mol_type = other DNA
                          organism = synthetic construct
SEQUENCE: 187
ggcgaaagtc aggctgtg                                                       18

SEQ ID NO: 188            moltype = DNA  length = 24
FEATURE                   Location/Qualifiers
misc_feature              1..24
                          note = PRIMER/PROBE
source                    1..24
                          mol_type = other DNA
                          organism = synthetic construct
SEQUENCE: 188
catcaggaca agatgggcgg tatg                                                24

SEQ ID NO: 189            moltype = DNA  length = 20
FEATURE                   Location/Qualifiers
misc_feature              1..20
                          note = PRIMER/PROBE
source                    1..20
                          mol_type = other DNA
                          organism = synthetic construct
SEQUENCE: 189
gagaggatga ycagccacac                                                     20

SEQ ID NO: 190            moltype = DNA  length = 20
FEATURE                   Location/Qualifiers
misc_feature              1..20
                          note = PRIMER/PROBE
source                    1..20
                          mol_type = other DNA
                          organism = synthetic construct
SEQUENCE: 190
cgcccattgt scaatattcc                                                     20

SEQ ID NO: 191            moltype = DNA  length = 24
FEATURE                   Location/Qualifiers
misc_feature              1..24
                          note = PRIMER/PROBE
source                    1..24
                          mol_type = other DNA
                          organism = synthetic construct
SEQUENCE: 191
tgagacacgg tccagactcc tacg                                                24

SEQ ID NO: 192            moltype = DNA  length = 21
FEATURE                   Location/Qualifiers
misc_feature              1..21
                          note = PRIMER/PROBE
source                    1..21
                          mol_type = other DNA
                          organism = synthetic construct
SEQUENCE: 192
gctgctcaag gagcacagga t                                                   21

SEQ ID NO: 193            moltype = DNA  length = 22
FEATURE                   Location/Qualifiers
misc_feature              1..22
                          note = PRIMER/PROBE
source                    1..22
                          mol_type = other DNA
                          organism = synthetic construct
SEQUENCE: 193
cacattgaca taggtgtggt gc                                                  22

SEQ ID NO: 194            moltype = DNA  length = 24
FEATURE                   Location/Qualifiers
misc_feature              1..24
                          note = PRIMER/PROBE
source                    1..24
                          mol_type = other DNA
                          organism = synthetic construct
SEQUENCE: 194
aggatggcaa ggcccactat ttca                                                24

SEQ ID NO: 195            moltype = DNA  length = 21
```

```
FEATURE                 Location/Qualifiers
misc_feature            1..21
                        note = PRIMER/PROBE
source                  1..21
                        mol_type = other DNA
                        organism = synthetic construct
SEQUENCE: 195
aacagcctca gcagccggtt a                                           21

SEQ ID NO: 196          moltype = DNA  length = 21
FEATURE                 Location/Qualifiers
misc_feature            1..21
                        note = PRIMER/PROBE
source                  1..21
                        mol_type = other DNA
                        organism = synthetic construct
SEQUENCE: 196
ttcgccgcaa tcatccctag c                                           21

SEQ ID NO: 197          moltype = DNA  length = 24
FEATURE                 Location/Qualifiers
misc_feature            1..24
                        note = PRIMER/PROBE
source                  1..24
                        mol_type = other DNA
                        organism = synthetic construct
SEQUENCE: 197
agccattacg ttccagagtt gcgt                                        24

SEQ ID NO: 198          moltype = DNA  length = 21
FEATURE                 Location/Qualifiers
misc_feature            1..21
                        note = PRIMER/PROBE
source                  1..21
                        mol_type = other DNA
                        organism = synthetic construct
SEQUENCE: 198
gccgaggctt acgggatcaa g                                           21

SEQ ID NO: 199          moltype = DNA  length = 21
FEATURE                 Location/Qualifiers
misc_feature            1..21
                        note = PRIMER/PROBE
source                  1..21
                        mol_type = other DNA
                        organism = synthetic construct
SEQUENCE: 199
caaagcgcgt aaccggattg g                                           21

SEQ ID NO: 200          moltype = DNA  length = 24
FEATURE                 Location/Qualifiers
misc_feature            1..24
                        note = PRIMER/PROBE
source                  1..24
                        mol_type = other DNA
                        organism = synthetic construct
SEQUENCE: 200
tctgctgaag tttrycgagg cmaa                                        24

SEQ ID NO: 201          moltype = DNA  length = 20
FEATURE                 Location/Qualifiers
misc_feature            1..20
                        note = PRIMER/PROBE
source                  1..20
                        mol_type = other DNA
                        organism = synthetic construct
SEQUENCE: 201
gagaggatga ycagccacac                                             20

SEQ ID NO: 202          moltype = DNA  length = 20
FEATURE                 Location/Qualifiers
misc_feature            1..20
                        note = PRIMER/PROBE
source                  1..20
                        mol_type = other DNA
                        organism = synthetic construct
SEQUENCE: 202
cgcccattgt scaatattcc                                             20
```

```
SEQ ID NO: 203          moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 203
tgagacacgg tccagactcc tacg                                          24

SEQ ID NO: 204          moltype = DNA   length = 22
FEATURE                 Location/Qualifiers
misc_feature            1..22
                        note = PRIMER/PROBE
source                  1..22
                        mol_type = other DNA
                        organism = synthetic construct
SEQUENCE: 204
aactttcaca ggtgtgctgg gt                                            22

SEQ ID NO: 205          moltype = DNA   length = 21
FEATURE                 Location/Qualifiers
misc_feature            1..21
                        note = PRIMER/PROBE
source                  1..21
                        mol_type = other DNA
                        organism = synthetic construct
SEQUENCE: 205
ccgtacgcat actggctttg c                                             21

SEQ ID NO: 206          moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 206
aaaccgggcg atatgcgtct gtat                                          24

SEQ ID NO: 207          moltype = DNA   length = 29
FEATURE                 Location/Qualifiers
misc_feature            1..29
                        note = PRIMER/PROBE
source                  1..29
                        mol_type = other DNA
                        organism = synthetic construct
SEQUENCE: 207
ctgggttcta taagtaaaac cttcaccgg                                     29

SEQ ID NO: 208          moltype = DNA   length = 21
FEATURE                 Location/Qualifiers
misc_feature            1..21
                        note = PRIMER/PROBE
source                  1..21
                        mol_type = other DNA
                        organism = synthetic construct
SEQUENCE: 208
cttccactgc ggctgccagt t                                             21

SEQ ID NO: 209          moltype = DNA   length = 23
FEATURE                 Location/Qualifiers
misc_feature            1..23
                        note = PRIMER/PROBE
source                  1..23
                        mol_type = other DNA
                        organism = synthetic construct
SEQUENCE: 209
gatgccattg cycgsggtga aat                                           23

SEQ ID NO: 210          moltype = DNA   length = 23
FEATURE                 Location/Qualifiers
misc_feature            1..23
                        note = PRIMER/PROBE
source                  1..23
                        mol_type = other DNA
                        organism = synthetic construct
SEQUENCE: 210
ccgaagccta tggcgtgaaa tcc                                           23
```

```
SEQ ID NO: 211            moltype = DNA   length = 19
FEATURE                   Location/Qualifiers
misc_feature              1..19
                          note = PRIMER/PROBE
source                    1..19
                          mol_type = other DNA
                          organism = synthetic construct
SEQUENCE: 211
gcaatgccct gctggagcg                                                   19

SEQ ID NO: 212            moltype = DNA   length = 20
FEATURE                   Location/Qualifiers
misc_feature              1..20
                          note = PRIMER/PROBE
source                    1..20
                          mol_type = other DNA
                          organism = synthetic construct
SEQUENCE: 212
atgttggcct gaacccagcg                                                  20

SEQ ID NO: 213            moltype = DNA   length = 20
FEATURE                   Location/Qualifiers
misc_feature              1..20
                          note = PRIMER/PROBE
source                    1..20
                          mol_type = other DNA
                          organism = synthetic construct
SEQUENCE: 213
gagaggatga ycagccacac                                                  20

SEQ ID NO: 214            moltype = DNA   length = 20
FEATURE                   Location/Qualifiers
misc_feature              1..20
                          note = PRIMER/PROBE
source                    1..20
                          mol_type = other DNA
                          organism = synthetic construct
SEQUENCE: 214
cgcccattgt scaatattcc                                                  20

SEQ ID NO: 215            moltype = DNA   length = 24
FEATURE                   Location/Qualifiers
misc_feature              1..24
                          note = PRIMER/PROBE
source                    1..24
                          mol_type = other DNA
                          organism = synthetic construct
SEQUENCE: 215
tgagacacgg tccagactcc tacg                                             24

SEQ ID NO: 216            moltype = DNA   length = 24
FEATURE                   Location/Qualifiers
misc_feature              1..24
                          note = PRIMER/PROBE
source                    1..24
                          mol_type = other DNA
                          organism = synthetic construct
SEQUENCE: 216
agcacataca gaatatgtcc ctgc                                             24

SEQ ID NO: 217            moltype = DNA   length = 25
FEATURE                   Location/Qualifiers
misc_feature              1..25
                          note = PRIMER/PROBE
source                    1..25
                          mol_type = other DNA
                          organism = synthetic construct
SEQUENCE: 217
acctgttaac caacctactt gaggg                                            25

SEQ ID NO: 218            moltype = DNA   length = 24
FEATURE                   Location/Qualifiers
misc_feature              1..24
                          note = PRIMER/PROBE
source                    1..24
                          mol_type = other DNA
                          organism = synthetic construct
SEQUENCE: 218
```

```
ttgcaagacg gactggctta gacc                                              24

SEQ ID NO: 219         moltype = DNA   length = 20
FEATURE                Location/Qualifiers
misc_feature           1..20
                       note = PRIMER/PROBE
source                 1..20
                       mol_type = other DNA
                       organism = synthetic construct
SEQUENCE: 219
cctgatcgga ttggagaacc                                                   20

SEQ ID NO: 220         moltype = DNA   length = 23
FEATURE                Location/Qualifiers
misc_feature           1..23
                       note = PRIMER/PROBE
source                 1..23
                       mol_type = other DNA
                       organism = synthetic construct
SEQUENCE: 220
ctacctcttg aataggcgta acc                                               23

SEQ ID NO: 221         moltype = DNA   length = 24
FEATURE                Location/Qualifiers
misc_feature           1..24
                       note = PRIMER/PROBE
source                 1..24
                       mol_type = other DNA
                       organism = synthetic construct
SEQUENCE: 221
acgtcgcgca agttcctgat agac                                              24

SEQ ID NO: 222         moltype = DNA   length = 25
FEATURE                Location/Qualifiers
misc_feature           1..25
                       note = PRIMER/PROBE
source                 1..25
                       mol_type = other DNA
                       organism = synthetic construct
SEQUENCE: 222
tagtgactgc taatccaaat cacag                                             25

SEQ ID NO: 223         moltype = DNA   length = 25
FEATURE                Location/Qualifiers
misc_feature           1..25
                       note = PRIMER/PROBE
source                 1..25
                       mol_type = other DNA
                       organism = synthetic construct
SEQUENCE: 223
gcacgagcaa gatcattacc atagc                                             25

SEQ ID NO: 224         moltype = DNA   length = 27
FEATURE                Location/Qualifiers
misc_feature           1..27
                       note = PRIMER/PROBE
source                 1..27
                       mol_type = other DNA
                       organism = synthetic construct
SEQUENCE: 224
agttatccaa caaggccaaa ctcaaca                                           27

SEQ ID NO: 225         moltype = DNA   length = 20
FEATURE                Location/Qualifiers
misc_feature           1..20
                       note = PRIMER/PROBE
source                 1..20
                       mol_type = other DNA
                       organism = synthetic construct
SEQUENCE: 225
gagaggatga ycagccacac                                                   20

SEQ ID NO: 226         moltype = DNA   length = 20
FEATURE                Location/Qualifiers
misc_feature           1..20
                       note = PRIMER/PROBE
source                 1..20
                       mol_type = other DNA
                       organism = synthetic construct
```

```
SEQUENCE: 226
cgcccattgt scaatattcc                                                   20

SEQ ID NO: 227          moltype = DNA  length = 24
FEATURE                 Location/Qualifiers
misc_feature            1..24
                        note = PRIMER/PROBE
source                  1..24
                        mol_type = other DNA
                        organism = synthetic construct
SEQUENCE: 227
tgagacacgg tccagactcc tacg                                              24

SEQ ID NO: 228          moltype = DNA  length = 20
FEATURE                 Location/Qualifiers
misc_feature            1..20
                        note = PRIMER/PROBE
source                  1..20
                        mol_type = other DNA
                        organism = synthetic construct
SEQUENCE: 228
aatcacaggg cgtagttgtg                                                   20

SEQ ID NO: 229          moltype = DNA  length = 20
FEATURE                 Location/Qualifiers
misc_feature            1..20
                        note = PRIMER/PROBE
source                  1..20
                        mol_type = other DNA
                        organism = synthetic construct
SEQUENCE: 229
acccaccagc caatcttagg                                                   20

SEQ ID NO: 230          moltype = DNA  length = 24
FEATURE                 Location/Qualifiers
misc_feature            1..24
                        note = PRIMER/PROBE
source                  1..24
                        mol_type = other DNA
                        organism = synthetic construct
SEQUENCE: 230
tagcttgatc gccctcgatt tggg                                              24

SEQ ID NO: 231          moltype = DNA  length = 18
FEATURE                 Location/Qualifiers
misc_feature            1..18
                        note = PRIMER/PROBE
source                  1..18
                        mol_type = other DNA
                        organism = synthetic construct
SEQUENCE: 231
gtgggatgga aagccacg                                                     18

SEQ ID NO: 232          moltype = DNA  length = 18
FEATURE                 Location/Qualifiers
misc_feature            1..18
                        note = PRIMER/PROBE
source                  1..18
                        mol_type = other DNA
                        organism = synthetic construct
SEQUENCE: 232
cacttgcggg tctacagc                                                     18

SEQ ID NO: 233          moltype = DNA  length = 24
FEATURE                 Location/Qualifiers
misc_feature            1..24
                        note = PRIMER/PROBE
source                  1..24
                        mol_type = other DNA
                        organism = synthetic construct
SEQUENCE: 233
ttactttggg cgaagccatg caag                                              24

SEQ ID NO: 234          moltype = DNA  length = 21
FEATURE                 Location/Qualifiers
misc_feature            1..21
                        note = PRIMER/PROBE
source                  1..21
                        mol_type = other DNA
```

```
                        organism = synthetic construct
SEQUENCE: 234
cacctatggt aatgctcttg c                                              21

SEQ ID NO: 235          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 235
ctggaactgc tgacaatgcc                                                20

SEQ ID NO: 236          moltype = DNA   length = 30
FEATURE                 Location/Qualifiers
misc_feature            1..30
                        note = PRIMER/PROBE
source                  1..30
                        mol_type = other DNA
                        organism = synthetic construct
SEQUENCE: 236
tgggagaaag atatgacttt aggtgaggca                                     30

SEQ ID NO: 237          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 237
gagaggatga ycagccacac                                                20

SEQ ID NO: 238          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 238
cgcccattgt scaatattcc                                                20

SEQ ID NO: 239          moltype = DNA   length = 24
FEATURE                 Location/Qualifiers
misc_feature            1..24
                        note = PRIMER/PROBE
source                  1..24
                        mol_type = other DNA
                        organism = synthetic construct
SEQUENCE: 239
tgagacacgg tccagactcc tacg                                           24

SEQ ID NO: 240          moltype = DNA   length = 18
FEATURE                 Location/Qualifiers
misc_feature            1..18
                        note = PRIMER/PROBE
source                  1..18
                        mol_type = other DNA
                        organism = synthetic construct
SEQUENCE: 240
agatcagttg ggtgcacg                                                  18

SEQ ID NO: 241          moltype = DNA   length = 20
FEATURE                 Location/Qualifiers
misc_feature            1..20
                        note = PRIMER/PROBE
source                  1..20
                        mol_type = other DNA
                        organism = synthetic construct
SEQUENCE: 241
tgcttaatca gtgaggcacc                                                20

SEQ ID NO: 242          moltype = DNA   length = 24
FEATURE                 Location/Qualifiers
misc_feature            1..24
                        note = PRIMER/PROBE
source                  1..24
```

```
                            mol_type = other DNA
                            organism = synthetic construct
SEQUENCE: 242
atgaagccat accaaacgac gagc                                              24

SEQ ID NO: 243              moltype = DNA   length = 20
FEATURE                     Location/Qualifiers
misc_feature                1..20
                            note = PRIMER/PROBE
source                      1..20
                            mol_type = other DNA
                            organism = synthetic construct
SEQUENCE: 243
ctggagcgaa agatccacta                                                   20

SEQ ID NO: 244              moltype = DNA   length = 18
FEATURE                     Location/Qualifiers
misc_feature                1..18
                            note = PRIMER/PROBE
source                      1..18
                            mol_type = other DNA
                            organism = synthetic construct
SEQUENCE: 244
atcgtccacc atccactg                                                     18

SEQ ID NO: 245              moltype = DNA   length = 22
FEATURE                     Location/Qualifiers
misc_feature                1..22
                            note = PRIMER/PROBE
source                      1..22
                            mol_type = other DNA
                            organism = synthetic construct
SEQUENCE: 245
ccagatcggc gacaacgtca cc                                                22

SEQ ID NO: 246              moltype = DNA   length = 20
FEATURE                     Location/Qualifiers
misc_feature                1..20
                            note = PRIMER/PROBE
source                      1..20
                            mol_type = other DNA
                            organism = synthetic construct
SEQUENCE: 246
gagaggatga ycagccacac                                                   20

SEQ ID NO: 247              moltype = DNA   length = 20
FEATURE                     Location/Qualifiers
misc_feature                1..20
                            note = PRIMER/PROBE
source                      1..20
                            mol_type = other DNA
                            organism = synthetic construct
SEQUENCE: 247
cgcccattgt scaatattcc                                                   20

SEQ ID NO: 248              moltype = DNA   length = 24
FEATURE                     Location/Qualifiers
misc_feature                1..24
                            note = PRIMER/PROBE
source                      1..24
                            mol_type = other DNA
                            organism = synthetic construct
SEQUENCE: 248
tgagacacgg tccagactcc tacg                                              24

SEQ ID NO: 249              moltype = DNA   length = 18
FEATURE                     Location/Qualifiers
misc_feature                1..18
                            note = PRIMER/PROBE
source                      1..18
                            mol_type = other DNA
                            organism = synthetic construct
SEQUENCE: 249
ccgtgtatgt tcagctat                                                     18

SEQ ID NO: 250              moltype = DNA   length = 18
FEATURE                     Location/Qualifiers
misc_feature                1..18
                            note = PRIMER/PROBE
```

```
source                  1..18
                        mol_type = other DNA
                        organism = synthetic construct
SEQUENCE: 250
cttatccatc acgccttt                                                       18

SEQ ID NO: 251          moltype = DNA   length = 26
FEATURE                 Location/Qualifiers
misc_feature            1..26
                        note = PRIMER/PROBE
source                  1..26
                        mol_type = other DNA
                        organism = synthetic construct
SEQUENCE: 251
tatgatgtcg ataccgccaa atacca                                              26

SEQ ID NO: 252          moltype = DNA   length = 18
FEATURE                 Location/Qualifiers
misc_feature            1..18
                        note = PRIMER/PROBE
source                  1..18
                        mol_type = other DNA
                        organism = synthetic construct
SEQUENCE: 252
ctgtatgtca gcgatcat                                                       18

SEQ ID NO: 253          moltype = DNA   length = 19
FEATURE                 Location/Qualifiers
misc_feature            1..19
                        note = PRIMER/PROBE
source                  1..19
                        mol_type = other DNA
                        organism = synthetic construct
SEQUENCE: 253
gatgccagtt tgcttatcc                                                      19

SEQ ID NO: 254          moltype = DNA   length = 25
FEATURE                 Location/Qualifiers
misc_feature            1..25
                        note = PRIMER/PROBE
source                  1..25
                        mol_type = other DNA
                        organism = synthetic construct
SEQUENCE: 254
aagtctgggt gagaacggtg tctat                                               25

SEQ ID NO: 255          moltype = DNA   length = 19
FEATURE                 Location/Qualifiers
misc_feature            1..19
                        note = PRIMER/PROBE
source                  1..19
                        mol_type = other DNA
                        organism = synthetic construct
SEQUENCE: 255
cagtcagtat gcgagtttc                                                      19

SEQ ID NO: 256          moltype = DNA   length = 18
FEATURE                 Location/Qualifiers
misc_feature            1..18
                        note = PRIMER/PROBE
source                  1..18
                        mol_type = other DNA
                        organism = synthetic construct
SEQUENCE: 256
aaaattcgcc aagccatc                                                       18

SEQ ID NO: 257          moltype = DNA   length = 25
FEATURE                 Location/Qualifiers
misc_feature            1..25
                        note = PRIMER/PROBE
source                  1..25
                        mol_type = other DNA
                        organism = synthetic construct
SEQUENCE: 257
tgcataagcc agtgcgtttt tatat                                               25

SEQ ID NO: 258          moltype = DNA   length = 20
FEATURE                 Location/Qualifiers
misc_feature            1..20
```

| | |
|---|---|
| | note = PRIMER/PROBE |
| source | 1..20 |
| | mol_type = other DNA |
| | organism = synthetic construct |

SEQUENCE: 258
gagaggatga ycagccacac                                           20

| SEQ ID NO: 259 | moltype = DNA  length = 20 |
|---|---|
| FEATURE | Location/Qualifiers |
| misc_feature | 1..20 |
| | note = PRIMER/PROBE |
| source | 1..20 |
| | mol_type = other DNA |
| | organism = synthetic construct |

SEQUENCE: 259
cgcccattgt scaatattcc                                           20

| SEQ ID NO: 260 | moltype = DNA  length = 24 |
|---|---|
| FEATURE | Location/Qualifiers |
| misc_feature | 1..24 |
| | note = PRIMER/PROBE |
| source | 1..24 |
| | mol_type = other DNA |
| | organism = synthetic construct |

SEQUENCE: 260
tgagacacgg tccagactcc tacg                                      24

| SEQ ID NO: 261 | moltype = DNA  length = 462 |
|---|---|
| FEATURE | Location/Qualifiers |
| misc_feature | 1..462 |
| | note = CONTROL MIX |
| source | 1..462 |
| | mol_type = other DNA |
| | organism = synthetic construct |

SEQUENCE: 261
tggccagaac tgacaggcaa acagtggcag ggtatccgcc tgctgcactt agccacctat   60
acggcaggcg gcctaccgct gcagatcccc gatgacgtta gggataaagc cgcattactg  120
cattttatc aaaactggca gccgcaatgg actccgggcg ctaagcgact ttacgctaac   180
tccagcattg gtctgtttgg cgcgctggcg gtgaaaccct caggaatgag ttacgaagag  240
gcaatgacca gacgcgtcct gcaaccatta aaactggcgc atacctggat tacggttccg  300
cagaacgaac aaaaagatta tgcctggggc tatcgcgaag ggaagcccgt acacgtttct  360
ccgggacaac ttgacgccga agcctatggc gtgaaatcca gcgttattga tatggcccgc  420
tgggttcagg ccaacatgga tgccagccac gttcaggaga aa                    462

| SEQ ID NO: 262 | moltype = DNA  length = 121 |
|---|---|
| FEATURE | Location/Qualifiers |
| misc_feature | 1..121 |
| | note = CONTROL MIX |
| source | 1..121 |
| | mol_type = other DNA |
| | organism = synthetic construct |

SEQUENCE: 262
ccgtcacgct gttgttagga agtgtgccgc tgtatgcgca acggcggac gtacagcaaa    60
aacttgccga attagagcgg cagtcgggag gcagactggg tgtggcattg attaacacag  120
c                                                                 121

| SEQ ID NO: 263 | moltype = DNA  length = 321 |
|---|---|
| FEATURE | Location/Qualifiers |
| misc_feature | 1..321 |
| | note = CONTROL MIX |
| source | 1..321 |
| | mol_type = other DNA |
| | organism = synthetic construct |

SEQUENCE: 263
cgtttcgtct ggatcgcact gaacctacgc tgaataccgc cattcccggc gacccgagag    60
acaccaccac gccgcgggcg atggcgcaga cgttgcgtca gcttacgctg ggtcatgcgc  120
tgggcgaaac ccagcgggcg cagttggtga cgtggctcaa aggcaatacg accggcgcag  180
ccagcattcg ggccggctta ccgacgtcgt ggactgtggg tgataagacc ggcagcggcg  240
actacggcac caccaatgat attgcggtga tctggccgca gggtcgtgcg ccgctggttc  300
tggtgaccta ttttacccag c                                           321

| SEQ ID NO: 264 | moltype = DNA  length = 84 |
|---|---|
| FEATURE | Location/Qualifiers |
| misc_feature | 1..84 |
| | note = CONTROL MIX |
| source | 1..84 |
| | mol_type = other DNA |
| | organism = synthetic construct |

SEQUENCE: 264

```
gagaggatga ccagccacac tggaactgag acacggtcca gactcctacg ggaggcagca    60
gtggggaata ttgcacaatg ggcg                                          84

SEQ ID NO: 265          moltype = DNA   length = 553
FEATURE                 Location/Qualifiers
misc_feature            1..553
                        note = CONTROL MIX
source                  1..553
                        mol_type = other DNA
                        organism = synthetic construct
SEQUENCE: 265
aatcacaggg cgtagttgtg ctctggaatg agaataagca gcaaggattt accaataatc    60
ttaaacgggc gaaccaagca tttttacccg catctacctt taaaattccc aatagcttga   120
tcgccctcga tttgggcgtg gttaaggatg aacaccaagt ctttaagtgg gatgacaga    180
cgcgcgatat cgccacttgg aatcgcgatc ataatctaat caccgcgatg aaatattcag   240
ttgtgcctgt ttatcaagaa tttgcccgcc aaattggcga ggcacgtatg agcaagatgc   300
tacatgcttt cgattatggt aatgaggaca tttcgggcaa tgtagacagt ttctggctcg   360
acggtggtat tcgaatttcg gccacggagc aaatcagctt tttaagaaag ctgtatcaca   420
ataagttaca cgtatcggag cgcagcagc gtattgtcaa acaagccatg ctgaccgaag    480
ccaatggtga ctatattatt cgggctaaaa ctggatactc gactagaatc gaacctaaga   540
ttggctggtg ggt                                                      553

SEQ ID NO: 266          moltype = DNA   length = 175
FEATURE                 Location/Qualifiers
misc_feature            1..175
                        note = CONTROL MIX
source                  1..175
                        mol_type = other DNA
                        organism = synthetic construct
SEQUENCE: 266
gcggagttag ttattggcta gttaaaaata aaattgaagt ttttatccc ggcccggggc     60
acactcaaga taacgtagtg gtttggttac ctgaaaagaa aatttattc ggtggttgtt   120
ttgttaaacc ggacggtctt ggtaatttgg gtgacgcaaa tttagaagct tggcc         175

SEQ ID NO: 267          moltype = DNA   length = 297
FEATURE                 Location/Qualifiers
misc_feature            1..297
                        note = CONTROL MIX
source                  1..297
                        mol_type = other DNA
                        organism = synthetic construct
SEQUENCE: 267
ggcggcgttg atgtccttcg ggcggctggg gtggcaacgt acgcatcacc gtcgacacgc    60
cggctagccg aggtagaggg gaacgagatt cccacgcact ctctagaagg actctcatcg   120
agcggggacg cagtgcgctt cggtccagta gaactcttct atcctggtgc tgcgcattcg   180
accgacaact tagttgtgta cgtcccgtct gcgagtgtgc tctatggtgg ttgtgcgatt   240
catgagttgt cacgcacgtc tgcggggaac gtggccgatg ccgatctggc tgaatgg      297

SEQ ID NO: 268          moltype = DNA   length = 84
FEATURE                 Location/Qualifiers
misc_feature            1..84
                        note = CONTROL MIX
source                  1..84
                        mol_type = other DNA
                        organism = synthetic construct
SEQUENCE: 268
gagaggatga ccagccacac tggaactgag acacggtcca gactcctacg ggaggcagca    60
gtggggaata ttgcacaatg ggcg                                          84

SEQ ID NO: 269          moltype = DNA   length = 405
FEATURE                 Location/Qualifiers
misc_feature            1..405
                        note = CONTROL MIX
source                  1..405
                        mol_type = other DNA
                        organism = synthetic construct
SEQUENCE: 269
aactttcaca ggtgtgctgg gtgcggtttc tgtggcgaaa aaagagatgg cgctgaatga    60
tccggcggca aaataccagc cggagctggc tctgccgcag tggaagggga tcacattgct   120
ggatctggct acctataccg caggcggact gccgttacag gtgccggatg cggtaaaaag   180
ccgtgcggat ctgctgaatt tctatcagca gtggcagccg tcccgaaac cgggcgatat    240
gcgtctgtat gcaaacagca gtatcggcct gtttggtgct ctgaccgcaa acgcggcggg   300
gatgccgtat gagcagttgc tgactgcacg gatcctggca ccgctggggt tatctcacac   360
ctttattact gtgccggaaa gtgcgcaaag ccagtatgcg tacgg                   405

SEQ ID NO: 270          moltype = DNA   length = 209
FEATURE                 Location/Qualifiers
misc_feature            1..209
                        note = CONTROL MIX
```

```
source                  1..209
                        mol_type = other DNA
                        organism = synthetic construct
SEQUENCE: 270
gtatcgccgt ctagttctgc tgtcttgtct ctcatggccg ctggctggct tttctgccac    60
cgcgctgacc aacctcgtcg cggaaccatt cgctaaactc gaacaggact ttggcggctc   120
catcggtgtg tacgcgatgg ataccggctc aggcgcaact gtaagttacc gcgctgagga   180
gcgcttccca ctgtgcagct cattcaagg                                     209

SEQ ID NO: 271          moltype = DNA   length = 263
FEATURE                 Location/Qualifiers
misc_feature            1..263
                        note = CONTROL MIX
source                  1..263
                        mol_type = other DNA
                        organism = synthetic construct
SEQUENCE: 271
gtttgatcgt cagggatggc ggccgcgtgc tggtggtcga taccgcctgg accgatgacc    60
agaccgccca gatcctcaac tggatcaagc aggagatcaa cctgccggtc gcgctggcgg   120
tggtgactca cgcgcatcag gacaagatgg gcggtatgga cgcgctgcat gcggcgggga   180
ttgcgactta tgccaatgcg ttgtcgaacc agcttgcccc gcaagagggg atggttgcgg   240
cgcaacacag cctgactttc gcc                                           263

SEQ ID NO: 272          moltype = DNA   length = 84
FEATURE                 Location/Qualifiers
misc_feature            1..84
                        note = CONTROL MIX
source                  1..84
                        mol_type = other DNA
                        organism = synthetic construct
SEQUENCE: 272
gagaggatga ccagccacac tggaactgag acacggtcca gactcctacg ggaggcagca    60
gtggggaata ttgcacaatg ggcg                                           84

SEQ ID NO: 273          moltype = DNA   length = 520
FEATURE                 Location/Qualifiers
misc_feature            1..520
                        note = CONTROL MIX
source                  1..520
                        mol_type = other DNA
                        organism = synthetic construct
SEQUENCE: 273
gctgctcaag gagcacagga tcccgggcat ggcggtggcc gtgctcaagg atggcaaggc    60
ccactatttc aattacgggg tggccaaccg ggagagcggg gccagcgtca gcgagcagac   120
cctgttcgag ataggatccg tgagcaagac cctgactgcg accctggggg cctatgcggt   180
ggtcaaggga gcgatgcagc tggatgacaa ggcgagccgg cacgcgccct ggctcaaggg   240
atccgtcttt gacagcatca ccatggggga gcttgccacc tacagcgccg gaggcctgcc   300
actgcaattc cccgaggagg tggattcatc cgagaagatg cgcgcctact accgccagtg   360
ggccctgtc tattcgccgg gctcccatcg ccagtactcc aacccagca tagggctgtt   420
cggccacctg gcggcgagca gcctgaagca gccatttgcc cagttgatgg agcagaccct   480
gctgcccggg ctcggcatgc accacaccta tgtcaatgtg                         520

SEQ ID NO: 274          moltype = DNA   length = 346
FEATURE                 Location/Qualifiers
misc_feature            1..346
                        note = CONTROL MIX
source                  1..346
                        mol_type = other DNA
                        organism = synthetic construct
SEQUENCE: 274
aacagcctca gcagccggtt acggaaaata cgttatttga agtgggttcg ctgagtaaaa    60
cgtttgctgc caccttggcg tcctatgcgc aggtgagcgg taagctgtct ttggatcaaa   120
gcgttagcca ttacgttcca gagttgcgtg cagcagctt tgaccacgtt agcgtactca   180
atgtgggcac gcataccca ggcctacagc tatttagcg aagatatt aaaaatacca   240
cacagctgat ggcttatcta aaagcatgga aacctgccga tgcggctgga acccatcgcg   300
tttattccaa tatcggtact ggtttgctag ggatgattgc ggcgaa               346

SEQ ID NO: 275          moltype = DNA   length = 247
FEATURE                 Location/Qualifiers
misc_feature            1..247
                        note = CONTROL MIX
source                  1..247
                        mol_type = other DNA
                        organism = synthetic construct
SEQUENCE: 275
gccgaggctt acgggatcaa gaccggctcg gcggatctgc tgaagtttac cgaggccaac    60
atggggtatc agggagatgc cgcgctaaaa acgcggatcg cgctgaccca taccggtttc   120
tactcggtgg gagacatgac tcaggggctg ggttgggaga gctacgccta tccgttgacc   180
gagcaggcgc tgctggcggg caactccccg gcggtgagct ccaggccaa tccggttacg   240
```

```
cgctttg                                                                    247

SEQ ID NO: 276            moltype = DNA   length = 84
FEATURE                   Location/Qualifiers
misc_feature              1..84
                          note = CONTROL MIX
source                    1..84
                          mol_type = other DNA
                          organism = synthetic construct
SEQUENCE: 276
gagaggatga ccagccacac tggaactgag acacggtcca gactcctacg ggaggcagca          60
gtggggaata ttgcacaatg ggcg                                                 84

SEQ ID NO: 277            moltype = DNA   length = 405
FEATURE                   Location/Qualifiers
misc_feature              1..405
                          note = CONTROL MIX
source                    1..405
                          mol_type = other DNA
                          organism = synthetic construct
SEQUENCE: 277
aactttcaca ggtgtgctgg gtgcggtttc tgtggcgaaa aaagagatgg cgctgaatga          60
tccggcggca aaataccagc cggagctggc tctgccgcag tggaagggga tcacattgct         120
ggatctggct acctataccg caggcggact gccgttacag gtgccggatg cggtaaaaag         180
ccgtgcggat ctgctgaatt tctatcagca gtggcagccg tcccggaaac cgggcgtatat        240
gcgtctgtat gcaaacagca gtatcggcct gtttggtgcc ctgaccgcaa acgcggcggg         300
gatgccgtat gagcagttgc tgactgcacg gatcctggca ccgtcgggt tatctcacac          360
ctttattact gtgccggaaa gtgcgcaaag ccagtatgcg tacgg                         405

SEQ ID NO: 278            moltype = DNA   length = 302
FEATURE                   Location/Qualifiers
misc_feature              1..302
                          note = CONTROL MIX
source                    1..302
                          mol_type = other DNA
                          organism = synthetic construct
SEQUENCE: 278
tcggtaaagc cgatgttgcg gcgaacaaac ccgtcacccc gcaaaccctg tttgagctgg          60
gctctataag taaaaccttc accggcgtac tgggcggcga tgccattgcc cggggtgaaa         120
tagcgctggg cgatccggta gcaaaatact ggcctgagct cacggggcaag cagtggcagg        180
gcattgcat gctggatctg gcaacctata ccgcaggcgg tctgccgtta caggtgccgg          240
atgaggtcac ggataccgcc tctctgctgc gcttttatca aaactggcag ccgcagtgga         300
ag                                                                        302

SEQ ID NO: 279            moltype = DNA   length = 106
FEATURE                   Location/Qualifiers
misc_feature              1..106
                          note = CONTROL MIX
source                    1..106
                          mol_type = other DNA
                          organism = synthetic construct
SEQUENCE: 279
ccgaagccta tggcgtgaaa tccagcgtta ttgatatggc ccgctgggtt caggccaaca          60
tggatgccag ccacgttcag gagaaaacgc tccagcaggg cattgc                       106

SEQ ID NO: 280            moltype = DNA   length = 84
FEATURE                   Location/Qualifiers
misc_feature              1..84
                          note = CONTROL MIX
source                    1..84
                          mol_type = other DNA
                          organism = synthetic construct
SEQUENCE: 280
gagaggatga ccagccacac tggaactgag acacggtcca gactcctacg ggaggcagca          60
gtggggaata ttgcacaatg ggcg                                                 84

SEQ ID NO: 281            moltype = DNA   length = 487
FEATURE                   Location/Qualifiers
misc_feature              1..487
                          note = CONTROL MIX
source                    1..487
                          mol_type = other DNA
                          organism = synthetic construct
SEQUENCE: 281
agcacataca gaatatgtcc ctgcatcaac atttaagatg ctaaatgcct taattggact          60
agaaaatcat aaagctacaa caactgagat tttcaaatgg gacggtaaaa agagatctta        120
tcccatgtgg gaaaaagata tgactttagg tgatgccatg gcactttcag cagttcctgt        180
atatcaagaa cttgcaagac ggactggctt agacctaatg caaaaagaag ttaaacgggt        240
tggttttgt aatatgaaca ttggaacaca gttgataac ttctggttgg ttgcccct            300
```

```
caagattaca ccaatacaag aggttaattt tgccgatgat tttgcaaata atcgattacc    360
ctttaaatta gagactcaag aagaagttaa aaaaatgctt ctgattaaag aattcaatgg    420
tagtaaaatt tatgcaaaaa gcggctgggg aatggatgta accccctcaag taggttggtt   480
aacaggt                                                              487

SEQ ID NO: 282          moltype = DNA   length = 278
FEATURE                 Location/Qualifiers
misc_feature            1..278
                        note = CONTROL MIX
source                  1..278
                        mol_type = other DNA
                        organism = synthetic construct
SEQUENCE: 282
cctgatcgga ttggagaacc agaaaacgga tattaatgaa atatttaaat ggaagggcga    60
gaaaaggtca tttaccgctt gggaaaaaga catgacacta ggagaagcca tgaagctttc    120
tgcagtccca gtctatcagg aacttgcgcg acgtatcggt cttgatctca tgcaaaaaga    180
agtaaaacgt attggtttcg gtaatgctga aattggacag caggttgata atttctggtt    240
ggtaggacca ttaaaggtta cgcctattca agaggtag                            278

SEQ ID NO: 283          moltype = DNA   length = 151
FEATURE                 Location/Qualifiers
misc_feature            1..151
                        note = CONTROL MIX
source                  1..151
                        mol_type = other DNA
                        organism = synthetic construct
SEQUENCE: 283
tagtgactgc taatccaaat cacagcgctt caaaatctga tgaaaaagca gagaaaatta    60
aaaatttatt taacgaagta cacactacgg gtgttttagt tatccaacaa ggccaaactc    120
aacaaagcta tggtaatgat cttgctcgtg c                                   151

SEQ ID NO: 284          moltype = DNA   length = 84
FEATURE                 Location/Qualifiers
misc_feature            1..84
                        note = CONTROL MIX
source                  1..84
                        mol_type = other DNA
                        organism = synthetic construct
SEQUENCE: 284
gagaggatga ccagccacac tggaactgag acacggtcca gactcctacg ggaggcagca    60
gtggggaata ttgcacaatg ggcg                                           84

SEQ ID NO: 285          moltype = DNA   length = 553
FEATURE                 Location/Qualifiers
misc_feature            1..553
                        note = CONTROL MIX
source                  1..553
                        mol_type = other DNA
                        organism = synthetic construct
SEQUENCE: 285
aatcacaggg cgtagttgtg ctctggaatg agaataagca gcaaggattt accaataatc    60
ttaaacgggc gaaccaagca ttttttaccccg catctacctt taaaattccc aatagcttga   120
tcgccctcga tttgggcgtg gttaaggatg aacaccaagt ctttaagtgg gatggacaga    180
cgcgcgatat cgccacttgg aatcgcgatc ataatctaat caccgcgatg aaatattcag    240
ttgtgcctgt ttatcaagaa tttgcccgcc aaattggcga ggcacgtatg agcaagatgc    300
tacatgcttt cgattatggt aatgaggaca tttcgggcaa tgtagacagt ttctggctcg    360
acgtggtat tcgaatttcg gccacggagc aaatcagctt tttaagaaag ctgtatcaca    420
ataagttaca cgtatcggag cgcagccagc gtattgtcaa acaagccatg ctgaccgaag    480
ccaatggtga ctatattatt cgggctaaaa ctggatactc gactagaatc gaacctaaga    540
ttggctggtg ggt                                                       553

SEQ ID NO: 286          moltype = DNA   length = 376
FEATURE                 Location/Qualifiers
misc_feature            1..376
                        note = CONTROL MIX
source                  1..376
                        mol_type = other DNA
                        organism = synthetic construct
SEQUENCE: 286
gtgggatgga aagccacgtt tttttaaagc atgggacaaa gatttacttt tgggcgaagc    60
catgcaagca tctacagtgc ctgtatatca agaattggca cgtcgtattg gtccaagctt    120
aatgcaaagt gaattgcaac gtattggtta tgcaatatg caaataggca cggaagttga    180
tcaatttttgg ttgaaagggc ctttgacaat tacacctata caagaagtaa agtttgtgta    240
tgatttagcc caagggcaat tgccttttaa acctgaagtt cagcaacaag tgaaagagat    300
gttgtatgta gagcgcagag gggagaatcg tctatatgct aaaaagtggct ggggaatggc    360
tgtagacccg caagtg                                                    376

SEQ ID NO: 287          moltype = DNA   length = 376
FEATURE                 Location/Qualifiers
``` misc_feature            1..376
                        note = CONTROL MIX
source                  1..376
                        mol_type = other DNA
                        organism = synthetic construct
SEQUENCE: 287
cacttgcggg tctacagcca ttccccagcc acttttagca tatagacgat tctcccctct    60
gcgctctaca tacaacatct cttttcacttg ttgctgaact tcaggtttaa aaggcaattg   120
cccttgggct aaatcataca caaactttac ttcttgtata ggtgtaattg tcaaaggccc   180
tttcaaccaa aattgatcaa cttccgtgcc tatttgcata ttgccataac caatacgttg   240
caattcactt tgcattaagc ttggaccaat acgacgtgcc aattcttgat atacaggcac   300
tgtagatgct tgcatggctt cgcccaaagt aaaatctttg tcccatgctt taaaaaaacg   360
tggctttcca tcccac                                                    376

SEQ ID NO: 288          moltype = DNA   length = 203
FEATURE                 Location/Qualifiers
misc_feature            1..203
                        note = CONTROL MIX
source                  1..203
                        mol_type = other DNA
                        organism = synthetic construct
SEQUENCE: 288
cacctatggt aatgctcttg cacgagcaaa taaagaatat gtccctgcat caacatttaa    60
gatgctaaat gctttaatcg ggctagaaaa tcataaagca acaacaaatg agatttttcaa  120
atgggatggt aaaaaaagaa cttatcctat gtgggagaaa gatatgactt taggtgaggc   180
aatggcattg tcagcagttc cag                                            203

SEQ ID NO: 289          moltype = DNA   length = 84
FEATURE                 Location/Qualifiers
misc_feature            1..84
                        note = CONTROL MIX
source                  1..84
                        mol_type = other DNA
                        organism = synthetic construct
SEQUENCE: 289
gagaggatga ccagccacac tggaactgag acacggtcca gactcctacg ggaggcagca    60
gtggggaata ttgcacaatg ggcg                                           84

SEQ ID NO: 290          moltype = DNA   length = 1625
FEATURE                 Location/Qualifiers
misc_feature            1..1625
                        note = CONTROL MIX
source                  1..1625
                        mol_type = other DNA
                        organism = synthetic construct
SEQUENCE: 290
atgatgcagc atacttctgt gtggtaccga cgctcggtca gtccgtttgt tcttgtggga    60
gtgttgccgt tttcttgacc gcgaccgcca atcttacctt ttttgataaa atcagccaaa   120
cctatcccat cgcggacaat ctcggctttg tgctgacgat cgctgtcgtg ctctttggcg   180
cgatgctact gatcaccacg ctgttatcat cgtatcgcta tgtgctaaag cctgtgttga   240
ttttgctatt aatcatgggc gcggtgacca gttattttac tgacacttat ggcacggtct   300
atgatacgac catgctccaa aatgccctac agaccgacca agccgagacc aaggatctat   360
taaacgcagc gtttatcatg cgtatcattg gtttgggtgt gctaccaagt ttgcttgtgg   420
cttttgttaa ggtggattat ccgacttggg gcaagggttt gatgcgccga ttgggcttga   480
tcgtgcaaag tcttgcgctg attttactgc ctgtggtgc gttcagcagt cattatgcca   540
gtttctttcg cgtgcataag ccgctgcgta gctatgtcaa tccgatcatg ccaatctact   600
cggtgggtaa gcttgccagt attgagtata aaaaagccag tgcgccaaaa gataccattt   660
atcacgccaa agacgcggta caagcaacca agcctgatat gcgtaagcca cgcctagtgg   720
tgttcgtcgt cggtgagacg gcacgcgccg atcatgtcag cttcaatggc tatgagcgcg   780
atactttccc acagcttgcc aagatcgatg gcgtgaccaa ttttagcgat gtcacatcgt   840
gcggcacatc gacggcgtat tctgtgccgt gtatgttcag ctatcgggc gcggatgagt   900
atgatgtcga taccgccaaa taccaagaaa atgtgctgga tacgctggat cgcttgggcg   960
taagtatctt gtggcgtgat aataattcgg actcaaaagg cgtgatggat aagctgccaa  1020
aagcgcaatt tgccgattat aaatccgcga ccaacaacgc catctgcac accaatcctt  1080
ataacgaatg ccgcgatgtc ggtatgctcg ttggcttaga tgactttgtc gctgccaata  1140
acggcaaaga tatgctgatc atgctgcacc aaatgggcaa tcacgggcct gcgtattta   1200
agcgatatga tgaaaagttt gccaaattca cgccagtgtg tgaaggtaat gagcttgcca  1260
agtgcgaaca tcagtccttg atcaatgctt atgacaatgc cttgcttgcc accgatgatt  1320
tcatcgctca aagtatccag tggctgcaga cgcacagcaa tgcctatgat gtctcaatgc  1380
tgtatgtcag cgatcatggc gaaagtctgg gtgagaacgg tgtctatcta catggtatgc  1440
caaatgcctt tgcaccaaaa gaacagcgca gtgtgcctgc attttctgg acggataagc  1500
aaactggcat cacgccaatg gcaaccgata ccgtcctgac ccatgacgcg atcacgccga  1560
cattattaaa gctgtttgat gtcaccgcgg acaaagtcaa agaccgcacc gcattcatcc  1620
gctga                                                               1625

SEQ ID NO: 291          moltype = DNA   length = 1617
FEATURE                 Location/Qualifiers
misc_feature            1..1617
                        note = CONTROL MIX

| | | |
|---|---|---|
| source | 1..1617 | |
| | mol_type = other DNA | |
| | organism = synthetic construct | |

SEQUENCE: 291

```
atgacatcac atcactcttg gtatcgctat tctatcaatc cttttgtgct gatgggtttg    60
gtggcgttat ttttggcagc gacagcgaac ctgacatttt ttgaaaaagc gatggcggtc   120
tatcctgtat cggataactt aggctttatc atctcaatgg cggtggcggt gatgggtgct   180
atgctactga ttgtcgtgct gttatccgtat cgctatgtgc taaagcctgt cctgattttg   240
ctactgatta tgggtgcggt gacgagctat tttaccgata cttatggcac ggtctatgac   300
accaccatgc tccaaaatgc catgcaaacc gaccaagccg agtctaagga cttgatgaat   360
ttggcgtttt ttgtgcgaat tatcgggctt ggcgtgttgc caagtgtgtt ggtcgcagtt   420
gccaaagtca attatccaac atggggcaaa ggtctgattc agcgtgcgat gacatggggt   480
gtcagccttg tgctgttgct tgtgccgatt ggactattta gcagtcagta tgcgagtttc   540
tttcgggtgc ataagccagt gcgtttttat atcaacccga ttacgccgat ttattcggtg   600
ggtaagcttg ccagtatcga gtacaaaaaa gccactgcgc aacagacac catctatcat    660
gccaaagacg ccgtgcagac caccaagccg agcgagcgta agccacgcct agtggtgttc   720
gtcgtcggtg agacggcgcg tgctgaccat gtgcagttca atggctatgg ccgtgagact   780
ttcccgcagc ttgccaaagt tgatggcttg gcgaatttta gccaagtgac atcgtgtggc   840
acatcgacgg cgtattctgt gccgtgtatg ttcagctatt tgggtcaaga tgactatgat   900
gtcgataccg ccaaatacca agaaaatgtg ctagatacgc ttgaccgctt gggtgtgggt   960
atcttgtggc gtgataataa ttcagactca aaaggcgtga tggataagct acctgccacg  1020
cagtattttg attataaatc agcaaccaac aataccatcg gtaacaccaa tccctataac  1080
gaatgccgtg atgtcggtat gcttgtcggg ctagatgact atgtcagcgc caataatggc  1140
aaagatatgc tcatcatgct acaccaaatg ggcaatcatg ggccggcgta ctttaagcgt  1200
tatgatgagc aatttgccaa attcacccccc gtgtgcgaag caacgagct tgccaaatgc  1260
gaacaccaat cactcatcaa tgcctatgac aatgcgctac ttgcgactga tgattttatc  1320
gccaaaagca tcgattggct aaaaaacgcat gaagcgaact acgatgtcgc catgctctat  1380
gtcagtgacc acgcgagag cttgggcgaa aatggtgtct atctgcatgg tatgccaaat  1440
gcctttgcac caaaagaaca gcgagctgtg cctgcgtttt tttggtcaaa taatacgaca  1500
ttcaagccaa ctgccagcga tactgtgctg acgcatgatg cgattacgcc aacactgctt  1560
aagctgtttg atgtcacagc gggcaaggtc aaagaccgcg cggcatttat ccagtaa    1617
```

| | | |
|---|---|---|
| SEQ ID NO: 292 | moltype = DNA  length = 84 | |
| FEATURE | Location/Qualifiers | |
| misc_feature | 1..84 | |
| | note = CONTROL MIX | |
| source | 1..84 | |
| | mol_type = other DNA | |
| | organism = synthetic construct | |

SEQUENCE: 292

```
gagaggatga ccagccacac tggaactgag acacggtcca gactcctacg ggaggcagca    60
gtggggaata ttgcacaatg ggcg                                           84
```

| | | |
|---|---|---|
| SEQ ID NO: 293 | moltype = DNA  length = 750 | |
| FEATURE | Location/Qualifiers | |
| misc_feature | 1..750 | |
| | note = CONTROL MIX | |
| source | 1..750 | |
| | mol_type = other DNA | |
| | organism = synthetic construct | |

SEQUENCE: 293

```
agatcagttg ggtgcacgag tgggttacat cgaactggat ctcaacacgcg gtaagatcct    60
tgagagtttt cgccccgaag aacgttttcc aatgatgagc acttttaaag ttctgctatg   120
tggtgcggta ttatcccgtg ttgacgccgg gcaagagcaa ctcggtcgcc gcatacacta   180
ttctcagaat gacttggttg agtactcacc agtcacagaa agcatcctta cggatggcat   240
gacagtaaga gaattatgca gtgctgccat aaccatgagt gataacactg cggccaactt   300
acttctgaca acgatcggag gaccgaagga gctaaccgct tttttgcaca catgggggga   360
tcatgtaact cgccttgatc gttgggaacc ggagctgaat gaagccatac caaacgacga   420
gcgtgacacc acgacgcctg cagcaatggc aacaacttg cgcaaactat taactggcga   480
actacttact ctagcttccc ggcaacaatt aatagactgg atggaggcgg ataaagttgc   540
aggaccactt ctgcgctcgg cccttccggc tggctggttt attgctgata atctggagc   600
cagtgagcgt gggtctcgcg gtatcattgc agcactgggg ccagatggta gccctcccg   660
tatcgtagtt atctacacga cggggagtca ggcaactatg gatgaacgaa atagacagat   720
cgctgagata ggtgcctcac tgattaagca                                    750
```

| | | |
|---|---|---|
| SEQ ID NO: 294 | moltype = DNA  length = 372 | |
| FEATURE | Location/Qualifiers | |
| misc_feature | 1..372 | |
| | note = CONTROL MIX | |
| source | 1..372 | |
| | mol_type = other DNA | |
| | organism = synthetic construct | |

SEQUENCE: 294

```
ctggagcgaa agatccacta tcgccagcag gatctggtgg actactcgcc ggtcagcgaa    60
aaacaccttg ccgacggcat gacggtcggc gaactctgcg ccgccgccat taccatgagc   120
gataacagcg ccgccaatct gctgctggcc accgtcggcg ccccgcagg attgactgcc   180
tttttgcgcc agatcggcga caacgtcacc cgccttgacc gctgggaaac ggaactgaat   240
gaggcgcttc ccgcgacgc ccgcgacacc actacccgg ccagcatggc cgcgaccctg   300
cgcaagctgc tgaccagcca gcgtctgagc gcccgttcgc aacggcagct gctgcagtgg   360
```

```
atggtggacg at                                                              372

SEQ ID NO: 295          moltype = DNA  length = 84
FEATURE                 Location/Qualifiers
misc_feature            1..84
                        note = CONTROL MIX
source                  1..84
                        mol_type = other DNA
                        organism = synthetic construct
SEQUENCE: 295
gagaggatga ccagccacac tggaactgag acacggtcca gactcctacg ggaggcagca            60
gtggggaata ttgcacaatg ggcg                                                  84

SEQ ID NO: 296          moltype = DNA  length = 24
FEATURE                 Location/Qualifiers
misc_feature            1..24
                        note = Synthetic
misc_feature            1
                        note = 6-FAM
misc_feature            9
                        note = ZEN
misc_feature            24
                        note = IABkFQ
source                  1..24
                        mol_type = other DNA
                        organism = synthetic construct
SEQUENCE: 296
aggatggcaa ggcccactat ttca                                                  24

SEQ ID NO: 297          moltype = DNA  length = 24
FEATURE                 Location/Qualifiers
misc_feature            1..24
                        note = Synthetic
misc_feature            1
                        note = HEX
misc_feature            9
                        note = ZEN
misc_feature            24
                        note = IABkFQ
source                  1..24
                        mol_type = other DNA
                        organism = synthetic construct
SEQUENCE: 297
agccattacg ttccagagtt gcgt                                                  24

SEQ ID NO: 298          moltype = DNA  length = 24
FEATURE                 Location/Qualifiers
misc_feature            1..24
                        note = Synthetic
misc_feature            1
                        note = TEX615
misc_feature            24
                        note = 3IAbRQSp
source                  1..24
                        mol_type = other DNA
                        organism = synthetic construct
SEQUENCE: 298
tctgctgaag tttrycgagg cmaa                                                  24

SEQ ID NO: 299          moltype = DNA  length = 24
FEATURE                 Location/Qualifiers
misc_feature            1..24
                        note = Synthetic
misc_feature            1
                        note = TYE665
misc_feature            24
                        note = IAbRQSp
source                  1..24
                        mol_type = other DNA
                        organism = synthetic construct
SEQUENCE: 299
tgagacacgg tccagactcc tacg                                                  24

SEQ ID NO: 300          moltype = DNA  length = 24
FEATURE                 Location/Qualifiers
misc_feature            1..24
                        note = Synthetic
misc_feature            1
                        note = 6-FAM
```

```
misc_feature         9
                     note = ZEN
misc_feature         24
                     note = IABkFQ
source               1..24
                     mol_type = other DNA
                     organism = synthetic construct
SEQUENCE: 300
aaacgggcg atatgcgtct gtat                                    24

SEQ ID NO: 301       moltype = DNA  length = 23
FEATURE              Location/Qualifiers
misc_feature         1..23
                     note = Synthetic
misc_feature         1
                     note = HEX
misc_feature         9
                     note = ZEN
misc_feature         23
                     note = IABkFQ
source               1..23
                     mol_type = other DNA
                     organism = synthetic construct
SEQUENCE: 301
gatgccattg cycgsggtga aat                                    23

SEQ ID NO: 302       moltype = DNA  length = 20
FEATURE              Location/Qualifiers
misc_feature         1..20
                     note = Synthetic
misc_feature         1
                     note = TEX615
misc_feature         20
                     note = IAbRQSp
source               1..20
                     mol_type = other DNA
                     organism = synthetic construct
SEQUENCE: 302
atgttggcct gaacccagcg                                        20
```